US008802688B2

(12) United States Patent
Dow et al.

(10) Patent No.: US 8,802,688 B2
(45) Date of Patent: *Aug. 12, 2014

(54) SUBSTITUTED ACETYL-COA CARBOXYLASE INHIBITORS

(75) Inventors: Robert Lee Dow, Groton, CT (US); David James Edmonds, Pawcatuck, CT (US); David Andrew Griffith, Old Saybrook, CT (US); James Alfred Southers, Jr., Norwich, CT (US)

(73) Assignee: Pfizer Inc., New York, NY (US)

( * ) Notice: Subject to any disclaimer, the term of this patent is extended or adjusted under 35 U.S.C. 154(b) by 235 days.

This patent is subject to a terminal disclaimer.

(21) Appl. No.: 13/452,839

(22) Filed: Apr. 21, 2012

(65) Prior Publication Data
US 2012/0270893 A1    Oct. 25, 2012

Related U.S. Application Data

(60) Provisional application No. 61/478,240, filed on Apr. 22, 2011.

(51) Int. Cl.
*A61K 31/438* (2006.01)
*C07D 217/12* (2006.01)
*C07D 231/54* (2006.01)
*C07D 471/10* (2006.01)
*C07D 519/00* (2006.01)

(52) U.S. Cl.
CPC ............ *C07D 519/00* (2013.01); *C07D 471/10* (2013.01)
USPC ............................................ 514/278; 546/17

(58) Field of Classification Search
USPC ............................................ 546/17; 514/278
See application file for complete search history.

(56) References Cited

U.S. PATENT DOCUMENTS

| 8,288,405 B2 * | 10/2012 | Bagley et al. ................ 514/278 |
| 8,507,681 B2 * | 8/2013 | Bagley et al. ................ 546/17 |
| 2008/0171761 A1 | 7/2008 | Iino et al. |
| 2009/0253725 A1 | 10/2009 | Chang et al. |
| 2009/0270435 A1 | 10/2009 | Corbett et al. |
| 2010/0009982 A1 | 1/2010 | Anderson et al. |
| 2011/0028390 A1 | 2/2011 | Corbett et al. |
| 2011/0111046 A1 | 5/2011 | Bagley et al. |

FOREIGN PATENT DOCUMENTS

| EP | 1911753 | 4/2008 |
| EP | 2123652 | 11/2009 |
| JP | 2005119987 | 5/2005 |
| WO | 2004092179 | 10/2001 |
| WO | 03072197 | 9/2003 |
| WO | 2004/002986 | 1/2004 |
| WO | 2005113069 | 12/2005 |
| WO | 2007011809 | 1/2007 |
| WO | 2007011811 | 1/2007 |
| WO | 2007/061676 | 5/2007 |
| WO | 2007095603 | 8/2007 |
| WO | 2008065508 | 6/2008 |
| WO | 2008088689 | 7/2008 |
| WO | 2008102749 | 8/2008 |
| WO | 2008125945 | 10/2008 |
| WO | 2009144554 | 12/2009 |
| WO | 2009144555 | 12/2009 |
| WO | 2010002010 | 1/2010 |
| WO | 2011058473 | 5/2011 |
| WO | 2011058474 | 5/2011 |
| WO | 2012042433 | 4/2012 |

OTHER PUBLICATIONS

Bagley, et al., "Synthesis of 7-oxo-dihydrospiro[indazole-5,4'-piperidine] Acetyl-CoA Carboxylase Inhibitors", The Journal of Organic Chemistry, vol. 77(3), pp. 1497-1506 (2012).

OTHER PUBLICATIONS

Savage, et al., "Reversal of diet-induced hepatic steatosis and hepatic insulin resistance by antisense oligonucleotide inhibitors of acetyl-CoA carboxylases 1 and 2", The Journal of Clinical Investigation, vol. 116(3), pp. 817-824 (2006).

(Continued)

*Primary Examiner* — Rita Desai
(74) *Attorney, Agent, or Firm* — James T. Wasicak

(57) ABSTRACT

The invention provides a compound of Formula (I)

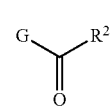

Formula (I)

or a pharmaceutically acceptable salt thereof; wherein G is

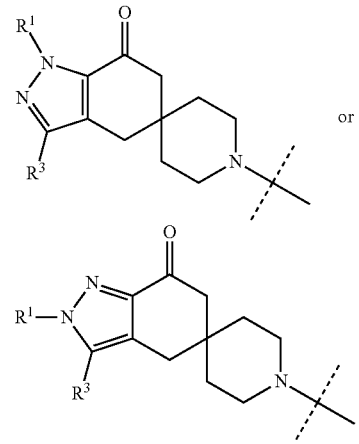

$R^1$, $R^2$ and $R^3$ are as described herein; pharmaceutical compositions thereof; and the use thereof in treating diseases, conditions or disorders modulated by the inhibition of an acetyl-CoA carboxylase enzyme(s) in an animal.

16 Claims, No Drawings

(56) References Cited

OTHER PUBLICATIONS

Oh, et al., "Glucose and fat metabolism in adipose tissue of acetyl-CoA carboxylase 2 knockout mice", PNAS, vol. 102(5), pp. 1384-1389 (2005).

Abu-Elheiga, et al., "Acetyl-CoA carboxylase 2 mutant mice are protected against obesity and diabetes induced by high-fat/high-carbohydrates diets", PNAS, vol. 100(18), pp. 10207-10212 (2003).

Choi, et al., "Continuous fat oxidation in acetyl-CoA carboxylase 2 knockout mice increases total energy expenditure, reduces fat mass, and improves insulin sensitivity", PNAS, vol. 104(42), pp. 16480-16485 (2007).

Database WPI Week 200537, Derwent Publications Ltd. No. 2005-359210 (XP002471702).

* cited by examiner

SUBSTITUTED ACETYL-COA CARBOXYLASE INHIBITORS

This application claims the benefit of U.S. Provisional Application No. 61/478,240, filed Apr. 22, 2011, hereby incorporated by reference.

FIELD OF THE INVENTION

This invention relates to substituted pyrazolospiroketone compounds that act as inhibitors of an acetyl-CoA carboxylase(s) and their use in treating diseases, conditions or disorders modulated by the inhibition of acetyl-CoA carboxylase enzyme(s).

BACKGROUND OF THE INVENTION

Acetyl-CoA carboxylases (ACC) are a family of enzymes found in most species and are associated with fatty acid synthesis and metabolism through catalyzing the production of malonyl-CoA from acetyl-CoA. In mammals, two isoforms of the ACC enzyme have been identified. ACC1, which is expressed at high levels in lipogenic tissues, such as fat and the liver, controls the first committed step in the biosynthesis of long-chain fatty acids. If acetyl-CoA is not carboxylated to form malonyl-CoA, it is metabolized through the Krebs cycle. ACC2, a minor component of hepatic ACC but the predominant isoform in heart and skeletal muscle, catalyzes the production of malonyl-CoA at the cytosolic surface of mitochondria, and regulates how much fatty acid is utilized in β-oxidation by inhibiting carnitine palmitoyl transferase. Thus, by increasing fatty acid utilization and by preventing increases in de novo fatty acid synthesis, chronic administration of an ACC inhibitor (ACC-1) may also deplete liver and adipose tissue triglyceride (TG) stores in obese subjects consuming a high or low-fat diet, leading to selective loss of body fat.

Studies conducted by Abu-Etheiga, et al., suggest that ACC2 plays an essential role in controlling fatty acid oxidation and, as such it would provide a target in therapy against obesity and obesity-related diseases, such as type-2 diabetes. See, Abu-Etheiga, L., et al., "Acetyl-CoA carboxylase 2 mutant mice are protected against obesity and diabetes induced by high-fat/high-carbohydrate diets" *PNAS*, 100(18) 10207-10212 (2003). See also, Choi, C. S., et al., "Continuous fat oxidation in acetyl-CoA carboxylase 2 knockout mice increases total energy expenditure, reduces fat mass, and improves insulin sensitivity" *PNAS*, 104(42) 16480-16485 (2007).

It is becoming increasingly clear that hepatic lipid accumulation causes hepatic insulin resistance and contributes to the pathogenesis of type 2 diabetes. Salvage, et al., demonstrated that ACC1 and ACC2 are both involved in regulating fat oxidation in hepatocytes while ACC1, the dominant isoform in rat liver, is the sole regulator of fatty acid synthesis. Furthermore, in their model, combined reduction of both isoforms is required to significantly lower hepatic malonyl-CoA levels, increase fat oxidation in the fed state, reduce lipid accumulation, and improve insulin action in vivo. Thus, showing that hepatic ACC1 and ACC2 inhibitors may be useful in the treatment of nonalcoholic fatty liver disease (NAFLD) and hepatic insulin resistance. See, Savage, D. B., et al., "Reversal of diet-induced hepatic steatosis and hepatic insulin resistance by antisense oligonucleotide inhibitors of acetyl-CoA carboxylases 1 and 2" *J Clin Invest* doi: 10.1172/JCI27300. See also, Oh, W., et al., "Glucose and fat metabolism in adipose tissue of acetyl-CoA carboxylase 2 knockout mice" *PNAS*, 102(5) 1384-1389 (2005).

Consequently, there is a need for medicaments containing ACC1 and/or ACC2 inhibitors to treat obesity and obesity-related diseases (such as, NAFLD and type-2 diabetes) by inhibiting fatty acid synthesis and by increasing fatty acid oxidation.

SUMMARY OF THE INVENTION

A first embodiment of the present invention relates to compounds having the structure of Formula A compound of Formula (I)

Formula (I)

or a pharmaceutically acceptable salt thereof; wherein
G is

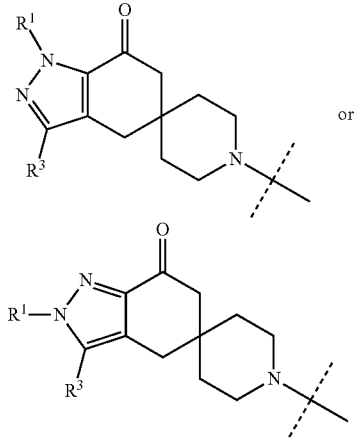

$R^1$ is a $(C_1-C_6)$alkyl or $(C_3-C_7)$ cylcoalkyl; $R^2$ is indolyl, indazolyl, pyrrolopyridinyl, pyrazolopyridinyl, quinolinyl or benzoimidazolyl; wherein each $R^2$ group is optionally substituted with one to two substituents independently selected from a cyano, -L-C(O)$NR^4R^5$, -L-$NR^4R^5$, $(C_1-C_3)$alkyl, $(C_1-C_3)$alkoxy and halo; $R^3$ is hydrogen or $(C_1-C_3)$alkyl; L is a direct bond or —X$(C_1-C_3)$alkylene; X is a direct bond, O or S; $R^4$ and $R^5$ are each independently hydrogen, $(C_1-C_3)$alkyl, $(C_3-C_7)$cycloalkyl or four to seven membered heterocyclyl wherein said $(C_1-C_3)$alkyl, $(C_3-C_7)$cycloalkyl or four to seven membered heterocyclyl is optionally substituted with one to three fluoro or $(C_1-C_3)$alkoxy.

A second embodiment of the present invention is the compound of the first embodiment or a pharmaceutically acceptable salt thereof wherein $R^2$ is indolyl, indazolyl, pyrrolopyridinyl, pyrazolopyridinyl, quinolinyl or benzoimidazolyl substituted with a cyano, -L-C(O)$NR^4R$ or -L-$NR^4R^5$.

A third embodiment of the present invention is the compound of the second embodiment or a pharmaceutically acceptable salt thereof wherein $R^2$ is indolyl, indazolyl, pyrrolopyridinyl, pyrazolopyridinyl, quinolinyl or benzoimidazolyl substituted with a -L-C(O)$NR^4R^5$ or -L-$NR^4R^5$; and L is a direct bond.

A fourth embodiment of the present invention is the compound of the first embodiment wherein R¹ is isopropyl, t-butyl or bicycle[1.1.1]pentanyl; or a pharmaceutically acceptable salt thereof. A fifth embodiment of the present invention is the compound of any of the preceding embodiments wherein R³ is hydrogen; or a pharmaceutically acceptable salt thereof.

Another embodiment of the present invention is the a compound of the first embodiment wherein G is

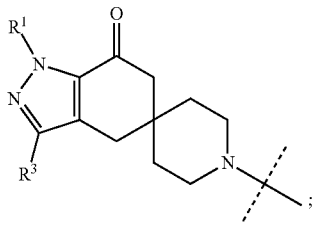

or a pharmaceutically acceptable salt thereof.

Another embodiment of the present invention is the compound of the first embodiment wherein G is

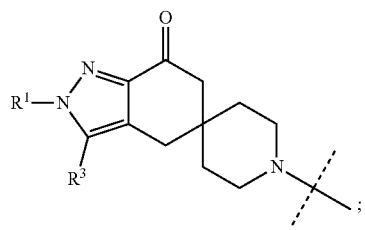

or a pharmaceutically acceptable salt thereof.

Another embodiment of the present invention is the compound wherein R² is

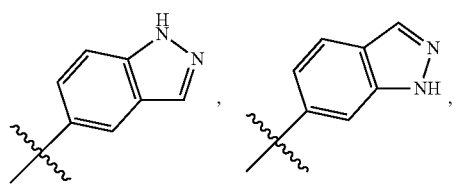

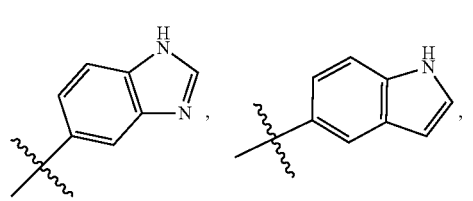

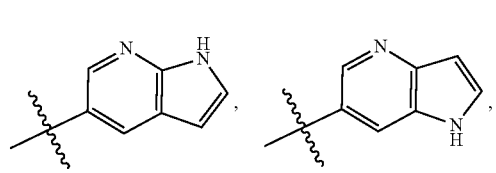

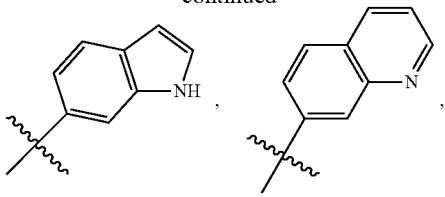

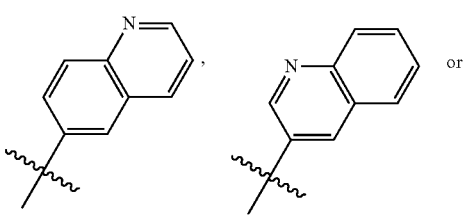

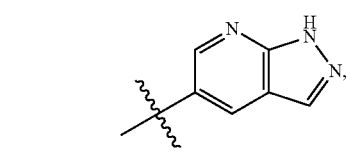

wherein each R² is substituted with a cyano, -L-C(O)NR⁴R⁵, -L-NR⁴R⁵; or a pharmaceutically acceptable salt thereof.

Yet another embodiment of the present invention is the compound or the preceding embodiment wherein R² is substituted with a cyano, —C(O)NH₂, —C(O)NHCH₃, —C(O)NHCH₂CH₃, —C(O)CH₂CF₃, —OCH₂C(O)NH₂; —NH₂, —NHCH₃ or —NHC(CH₃)₃; or a pharmaceutically acceptable salt thereof.

Another embodiment of the present invention is the compound wherein G is

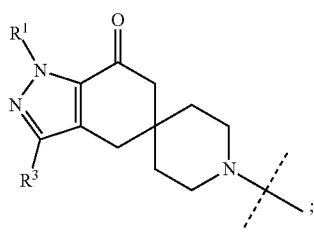

R¹ is a (C₁-C₆)alkyl or (C₃-C₇) cylcoalkyl; R² is indolyl, indazolyl, pyrrolopyridinyl, pyrazolopyridinyl, quinolinyl or benzoimidazolyl; wherein each R² group is optionally substituted with one to two substituents independently selected from a cyano, -L-C(O)NR⁴R⁵, -L-NR⁴R⁵, (C₁-C₃)alkyl, (C₁-C₃)alkoxy and halo; R³ is hydrogen or (C₁-C₃)alkyl; L is a direct bond or —X(C₁-C₃)alkylene; X is a direct bond, O or S; and R⁴ and R⁵ are each independently hydrogen, (C₁-C₃) alkyl, (C₃-C₇)cycloalkyl or four to seven membered heterocyclyl wherein said (C₁-C₃)alkyl, (C₃-C₇)cycloalkyl or four to seven membered heterocyclyl is optionally substituted with one to three fluoro or (C₁-C₃)alkoxy; or a pharmaceutically acceptable salt thereof.

Another embodiment of the present invention is the compound wherein G is

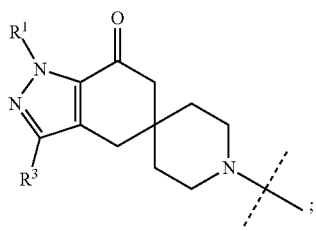

$R^1$ is a $(C_1$-$C_6)$alkyl or $(C_3$-$C_7)$ cylcoalkyl; $R^2$ is indolyl, indazolyl, pyrrolopyridinyl, pyrazolopyridinyl, quinolinyl or benzoimidazolyl; wherein each $R^2$ group is optionally substituted with one to two substituents independently selected from a cyano, -L-C(O)NR$^4$R$^5$, -L-NR$^4$R$^5$, $(C_1$-$C_3)$alkyl, $(C_1$-$C_3)$alkoxy and halo; $R^3$ is hydrogen; L is a direct bond or —X$(C_1$-$C_3)$alkylene; X is a direct bond, O or S; and $R^4$ and $R^5$ are each independently hydrogen, $(C_1$-$C_3)$alkyl, $(C_3$-$C_7)$cycloalkyl or four to seven membered heterocyclyl wherein said $(C_1$-$C_3)$alkyl, $(C_3$-$C_7)$cycloalkyl or four to seven membered heterocyclyl is optionally substituted with one to three fluoro or $(C_1$-$C_3)$alkoxy; or a pharmaceutically acceptable salt thereof.

Another embodiment of the present invention is the compound wherein G is

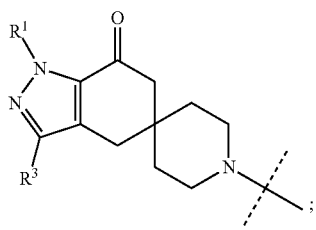

$R^1$ is $(C_1$-$C_6)$alkyl; $R^2$ is

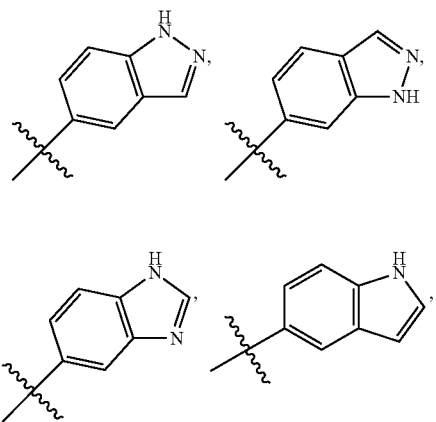

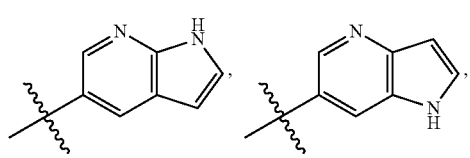

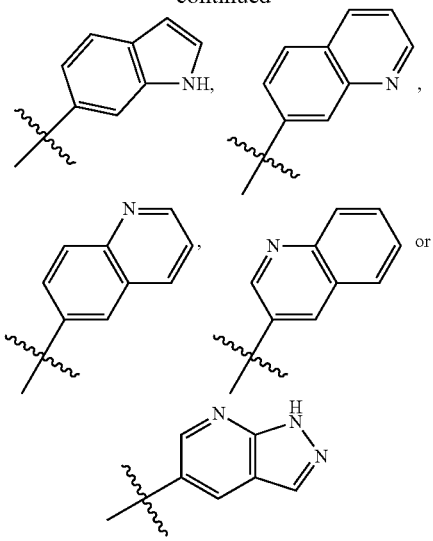

wherein each $R^2$ is substituted with one substituent that is -L-C(O)NR$^4$R$^5$, -L-NR$^4$R$^5$, or $(C_1$-$C_3)$alkoxy; $R^3$ is hydrogen; L is a direct bond or —X$(C_1$-$C_3)$alkylene; X is a direct bond, O or S; and $R^4$ and $R^5$ are each independently hydrogen or $(C_1$-$C_3)$alkyl; or a pharmaceutically acceptable salt thereof.

Another embodiment of the present invention is the compound wherein G is

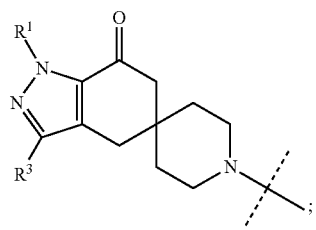

$R^1$ is $(C_1$-$C_6)$alkyl; $R^2$ is

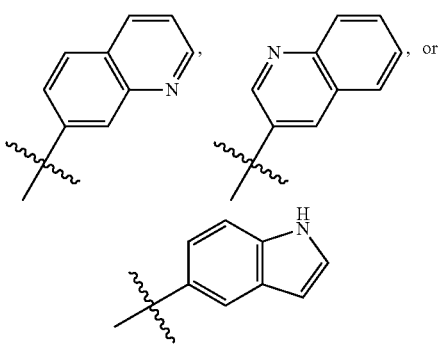

wherein each $R^2$ is substituted with one substituent that is -L-C(O)NR$^4$R$^5$, -L-NR$^4$R$^5$, or $(C_1$-$C_3)$alkoxy; L is a direct bond; and $R^4$ and $R^5$ are hydrogen; or a pharmaceutically acceptable salt thereof.

Another embodiment of the present invention is the compound wherein G is

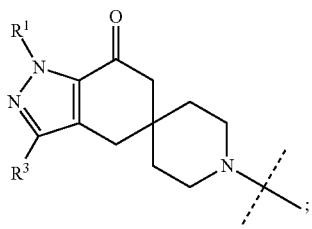

$R^1$ is $(C_1-C_6)$alkyl; $R^2$ is

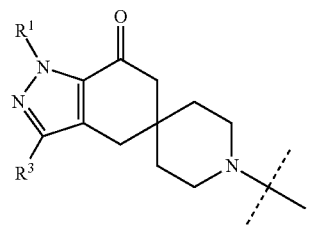

wherein $R^1$ is a $(C_1-C_6)$alkyl; $R^2$ is

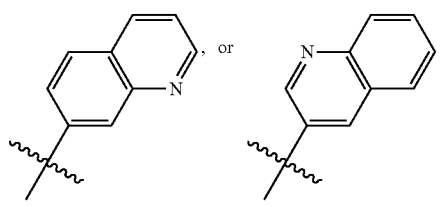

wherein each $R^2$ is substituted with one substituent that is -L-NR$^4$R$^5$ or $(C_1-C_3)$alkoxy; L is a direct bond; and $R^4$ and $R^5$ are hydrogen; or a pharmaceutically acceptable salt thereof.

Another embodiment of the present invention is the compound of the first embodiment wherein G is substituted with one substituent selected from $(C_1-C_3)$alkoxy; and $R^3$ is hydrogen.

Another embodiment of the present invention is the compound of the first embodiment wherein G is

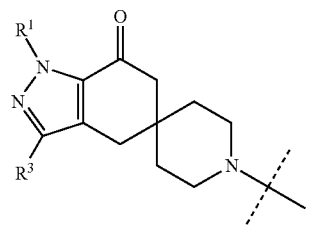

wherein $R^1$ is a $(C_1-C_6)$alkyl; $R^2$ is

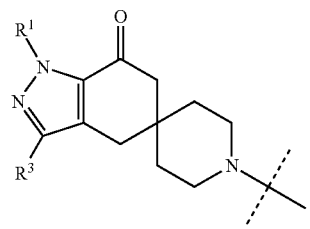

wherein $R^1$ is a $(C_1-C_6)$alkyl; $R^2$ is

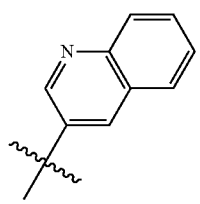 [SMILES: *c1cnc2ccccc2c1]

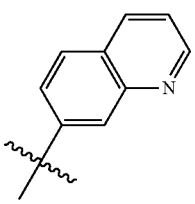 [SMILES: *c1ccc2cccnc2c1]

optionally substituted with one to two substituents independently selected from a cyano, -L-C(O)NR$^4$R$^5$, -L-NR$^4$R$^5$, $(C_1-C_3)$alkyl, $(C_1-C_3)$alkoxy and halo; $R^3$ is hydrogen or $(C_1-C_3)$alkyl; L is a direct bond; and $R^4$ and $R^5$ are each independently hydrogen or $(C_1-C_3)$alkyl.

Another embodiment of the present invention is the compound of the first embodiment wherein G is optionally substituted with one to two substituents independently selected from a cyano, -L-C(O)NR$^4$R$^5$, -L-NR$^4$R$^5$, $(C_1-C_3)$alkyl, $(C_1-C_3)$alkoxy and halo; $R^3$ is hydrogen or $(C_1-C_3)$alkyl; L is a direct bond; and $R^4$ and $R^5$ are each independently hydrogen or $(C_1-C_3)$alkyl.

Another embodiment of the present invention is the compound of the first embodiment wherein G is

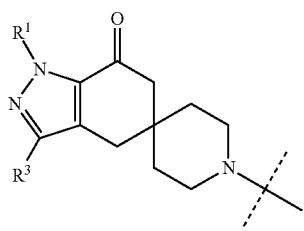

wherein $R^1$ is a $(C_1-C_6)$alkyl; $R^2$ is

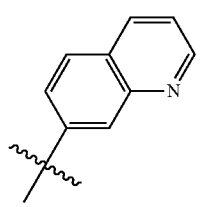 [SMILES: *c1ccc2cccnc2c1]

substituted with one substituent selected from -L-NR$^4$R$^5$; $R^3$ is hydrogen; L is a direct bond; and $R^4$ and $R^5$ are each hydrogen.

Another embodiment of the present invention is the compound of the first embodiment wherein G is

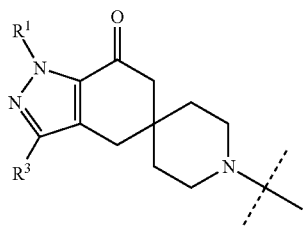

wherein $R^1$ is a $(C_1-C_6)$alkyl; $R^2$ is

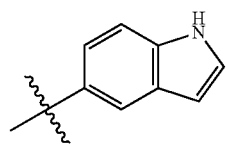 [SMILES: *c1ccc2[nH]ccc2c1]

optionally substituted with one to two substituents independently selected from a cyano, -L-C(O)NR$^4$R$^5$, -L-NR$^4$R$^5$, $(C_1-C_3)$alkyl, $(C_1-C_3)$alkoxy and halo; $R^3$ is hydrogen or $(C_1-C_3)$alkyl; L is a direct bond; and $R^4$ and $R^5$ are each independently hydrogen or $(C_1-C_3)$alkyl.

Another embodiment of the present invention is the compound of the first embodiment wherein G is

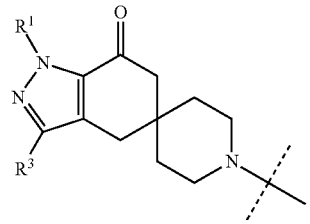

wherein $R^1$ is a $(C_1-C_6)$alkyl; $R^2$ is

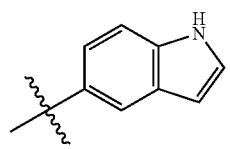 [SMILES: *c1ccc2[nH]ccc2c1]

substituted with one substituent selected from -L-C(O) NR$^4$R$^5$; $R^3$ is hydrogen; L is a direct bond; and $R^4$ and $R^5$ are each hydrogen.

Another embodiment of the present invention is the compound of structure

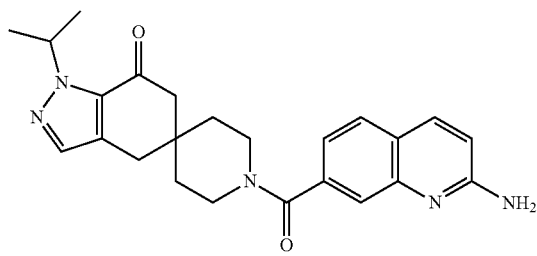 [SMILES: CC(C)n1ncc2c1C(=O)CC1(CCN(C(=O)c3ccc4ccc(N)nc4c3)CC1)C2]

or a pharmaceutically acceptable salt thereof.

Another embodiment of the present invention is the compound of structure

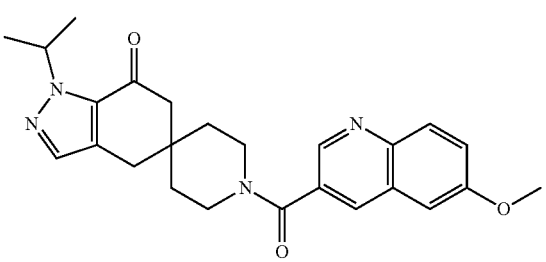 [SMILES: COc1ccc2ncc(C(=O)N3CCC4(CC3)CC(=O)c3c(cnn3C(C)C)C4)cc2c1]

or a pharmaceutically acceptable salt thereof.

Another embodiment of the present invention is the compound of structure

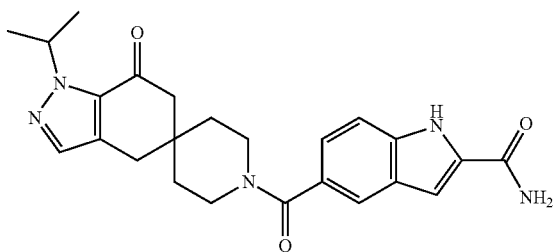

or a pharmaceutically acceptable salt thereof.

Another embodiment of the present invention is a compound selected from the group consisting of 6-[(1-isopropyl-7-oxo-1,4,6,7-tetrahydro-1'H-spiro[indazole-5,4'-piperidin]-1'-yl)carbonyl]-1H-indole-3-carboxamide; 5-[(1-isopropyl-7-oxo-1,4,6,7-tetrahydro-1'H-spiro[indazole-5,4'-piperidin]-1'-yl)carbonyl]-1H-indazole-3-carboxamide; 6-[(1-isopropyl-7-oxo-1,4,6,7-tetrahydro-1'H-spiro[indazole-5,4'-piperidin]-1'-yl)carbonyl]-1H-pyrrolo[3,2-b]pyridine-3-carboxamide; 6-[(1-isopropyl-7-oxo-1,4,6,7-tetrahydro-1'H-spiro[indazole-5,4'-piperidin]-1'-yl)carbonyl]-1H-indazole-3-carboxamide; 5-[(1-isopropyl-7-oxo-1,4,6,7-tetrahydro-1'H-spiro[indazole-5,4'-piperidin]-1'-yl)carbonyl]-1H-pyrrolo[2,3-b]pyridine-3-carboxamide; 5-[(1-isopropyl-7-oxo-1,4,6,7-tetrahydro-1'H-spiro[indazole-5,4'-piperidin]-1'-yl)carbonyl]-1H-indole-2-carboxamide; 5-[(1-isopropyl-7-oxo-1,4,6,7-tetrahydro-1'H-spiro[indazole-5,4'-piperidin]-1'-yl)carbonyl]-1H-indole-3-carboxamide; 1'-[(2-amino-1H-benzimidazol-5-yl)carbonyl]-1-isopropyl-1,4-dihydrospiro[indazole-5,4'-piperidin]-7(6H)-one; 5-[(1-isopropyl-7-oxo-1,4,6,7-tetrahydro-1'H-spiro[indazole-5,4'-piperidin]-1'-yl)carbonyl]-N-methyl-1H-indazole-3-carboxamide; N-ethyl-5-[(1-isopropyl-7-oxo-1,4,6,7-tetrahydro-1'H-spiro[indazole-5,4'-piperidin]-1'-yl)carbonyl]-1H-indazole-3-carboxamide; 5-[(1-isopropyl-7-oxo-1,4,6,7-tetrahydro-1'H-spiro[indazole-5,4'-piperidin]-1'-yl)carbonyl]-N-(2,2,2-trifluoroethyl)-1H-indazole-3-carboxamide; 6-[(1-isopropyl-7-oxo-1,4,6,7-tetrahydro-1'H-spiro[indazole-5,4'-piperidin]-1'-yl)carbonyl]-1H-indole-2-carboxamide; 5-[(1-isopropyl-7-oxo-1,4,6,7-tetrahydro-1'H-spiro[indazole-5,4'-piperidin]-1'-yl)carbonyl]-1H-pyrazolo[3,4-b]pyridine-3-carboxamide; 5-[(1-isopropyl-7-oxo-1,4,6,7-tetrahydro-1'H-spiro[indazole-5,4'-piperidin]-1'-yl)carbonyl]-1H-pyrrolo[2,3-b]pyridine-2-carboxamide; 1-isopropyl-1'-{[2-(methylamino)-1H-benzimidazol-5-yl]carbonyl}-1,4-dihydrospiro[indazole-5,4'-piperidin]-7(6H)-one; 5-[(1-isopropyl-7-oxo-1,4,6,7-tetrahydro-1'H-spiro[indazole-5,4'-piperidin]-1'-yl)carbonyl]-1H-benzimidazole-2-carboxamide; 5-[(1-tert-butyl-7-oxo-1,4,6,7-tetrahydro-1'H-spiro[indazole-5,4'-piperidin]-1'-yl)carbonyl]-1H-indazole-3-carboxamide; 5-[(1-tert-butyl-7-oxo-1,4,6,7-tetrahydro-1'H-spiro[indazole-5,4'-piperidin]-1'-yl)carbonyl]-1H-pyrrolo[2,3-b]pyridine-3-carboxamide; 6-[(2-tert-butyl-7-oxo-2,4,6,7-tetrahydro-1'H-spiro[indazole-5,4'-piperidin]-1'-yl)carbonyl]-1H-indole-3-carboxamide; 6-[(2-tert-butyl-7-oxo-2,4,6,7-tetrahydro-1'H-spiro[indazole-5,4'-piperidin]-1'-yl)carbonyl]-1H-indazole-3-carboxamide; 5-[(2-tert-butyl-7-oxo-2,4,6,7-tetrahydro-1'H-spiro[indazole-5,4'-piperidin]-1'-yl)carbonyl]-1H-pyrrolo[2,3-b]pyridine-3-carboxamide; 5-[(2-tert-butyl-7-oxo-2,4,6,7-tetrahydro-1'H-spiro[indazole-5,4'-piperidin]-1'-yl)carbonyl]-1H-indazole-3-carboxamide; 5-[(2-tert-butyl-7-oxo-2,4,6,7-tetrahydro-1'H-spiro[indazole-5,4'-piperidin]-1'-yl)carbonyl]-1H-indole-2-carboxamide; 5-[(2-tert-butyl-7-oxo-2,4,6,7-tetrahydro-1'H-spiro[indazole-5,4'-piperidin]-1'-yl)carbonyl]-1H-indole-3-carboxamide; 6-[(2-tert-butyl-7-oxo-2,4,6,7-tetrahydro-1'H-spiro[indazole-5,4'-piperidin]-1'-yl)carbonyl]-1H-indole-2-carboxamide; 1'-[(2-amino-1H-benzimidazol-5-yl)carbonyl]-2-tert-butyl-2,4-dihydrospiro[indazole-5,4'-piperidin]-7(6H)-one; 5-[(2-tert-butyl-7-oxo-2,4,6,7-tetrahydro-1'H-spiro[indazole-5,4'-piperidin]-1'-yl)carbonyl]-N-ethyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-methyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-(2,2,2-trifluoroethyl)-1H-indazole-3-carboxamide; 2-tert-butyl-1'-{[2-(methylamino)-1H-benzimidazol-5-yl]carbonyl}-2,4-dihydrospiro[indazole-5,4'-piperidin]-7(6H)-one; 6-[(2-tert-butyl-7-oxo-2,4,6,7-tetrahydro-1'H-spiro[indazole-5,4'-piperidin]-1'-yl)carbonyl]-1H-pyrrolo[3,2-b]pyridine-3-carboxamide; 6-[(2'-tert-butyl-7'-oxo-6',7'-dihydro-1H,2'H-spiro[piperidine-4,5'-pyrano[3,2-c]pyrazol]-1-yl)carbonyl]-1H-indazole-3-carboxamide; 6-[(2'-tert-butyl-7'-oxo-6',7'-dihydro-1H,2'H-spiro[piperidine-4,5'-pyrano[3,2-c]pyrazol]-1-yl)carbonyl]-1H-indole-2-carboxamide; 6-[(2'-tert-butyl-7'-oxo-6',7'-dihydro-1H,2'H-spiro[piperidine-4,5'-pyrano[3,2-c]pyrazol]-1-yl)carbonyl]-1H-indole-3-carboxamide; 5-[(2'-tert-butyl-7'-oxo-6',7'-dihydro-1H,2'H-spiro[piperidine-4,5'-pyrano[3,2-c]pyrazol]-1-yl)carbonyl]-1H-indazole-3-carboxamide; 5-[(2'-tert-butyl-7'-oxo-6',7'-dihydro-1H,2'H-spiro[piperidine-4,5'-pyrano[3,2-c]pyrazol]-1-yl)carbonyl]-1H-indole-2-carboxamide; 5-[(2'-tert-butyl-7'-oxo-6',7'-dihydro-1H,2'H-spiro[piperidine-4,5'-pyrano[3,2-c]pyrazol]-1-yl)carbonyl]-1H-indole-3-carboxamide; 5-[(2'-tert-butyl-7'-oxo-6',7'-dihydro-1H,2'H-spiro[piperidine-4,5'-pyrano[3,2-c]pyrazol]-1-yl)carbonyl]-1H-pyrrolo[2,3-b]pyridine-3-carboxamide; 1-[(2-amino-1H-benzimidazol-5-yl)carbonyl]-2'-tert-butyl-2'H-spiro[piperidine-4,5'-pyrano[3,2-c]pyrazol]-7'(6'H)-one; 2'-tert-butyl-1-{[2-(methylamino)-1H-benzimidazol-5-yl]carbonyl}-2'H-spiro[piperidine-4,5'-pyrano[3,2-c]pyrazol]-7'(6'H)-one; 6-[(2'-tert-butyl-7'-oxo-6',7'-dihydro-1H,2'H-spiro[piperidine-4,5'-pyrano[3,2-c]pyrazol]-1-yl)carbonyl]-1H-pyrrolo[3,2-b]pyridine-3-carboxamide; and 5-[(2'-tert-butyl-7'-oxo-6',7'-dihydro-1H,2'H-spiro[piperidine-4,5'-pyrano[3,2-c]pyrazol]-1-yl)carbonyl]-1H-benzimidazole-2-carboxamide. or a pharmaceutically acceptable salt thereof.

Yet another embodiment of the present invention is a compound selected from the group consisting of 6-[(2-tert-butyl-7-oxo-2,4,6,7-tetrahydro-1'H-spiro[indazole-5,4'-piperidin]-1'-yl)carbonyl]-1H-pyrrolo[3,2-b]pyridine-3-carbonitrile; 5-[(2-tert-butyl-7-oxo-2,4,6,7-tetrahydro-1'H-spiro[indazole-5,4'-piperidin]-1'-yl)carbonyl]-1H-pyrrolo[2,3-b]pyridine-3-carbonitrile; 1'-[(2-aminoquinolin-6-yl)carbonyl]-2-tert-butyl-2,4-dihydrospiro[indazole-5,4'-piperidin]-7(6H)-one; 5-[(1-isopropyl-7-oxo-1,4,6,7-tetrahydro-1'H-spiro[indazole-5,4'-piperidin]-1'-yl)carbonyl]-N-methyl-1H-indole-3-carboxamide; 6-[(1-isopropyl-7-oxo-1,4,6,7-tetrahydro-1'H-spiro[indazole-5,4'-piperidin]-1'-yl)carbonyl]-N-methyl-1H-indole-3-carboxamide; 5-[(2-tert-butyl-7-oxo-2,4,6,7-tetrahydro-1'H-spiro[indazole-5,4'-piperidin]-1'-yl)carbonyl]-N-cyclopropyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-isopropyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-propyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-(2-methoxyethyl)-1H-indazole-3-carboxamide; 5-[(2-tert-butyl-7-oxo-2,4,6,7-tetrahydro-1'H-spiro[indazole-5,4'- piperidin]-1'-yl)carbonyl]-N-cyclobutyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-oxetan-3-yl-1H-indazole-3-carboxamide; 6-[(2-tert-butyl-7-oxo-2,4,6,7-tetrahydro-1'H-spiro[indazole-5,4'-piperidin]-1'-yl)carbonyl]-Ncyclopropyl-1H-indazole-3-carboxamide; 6-[(2-tert-butyl-7-oxo-2,4,6,7-tetrahydro-1'H-spiro[indazole-5,4'-piperidin]-1'-yl)carbonyl]-N-methyl-1H-indazole-3-carboxamide; 6-[(2-tert-butyl-7-oxo-2,4,6,7-tetrahydro-1'H-spiro[indazole-5,4'-piperidin]-1'-yl)carbonyl]-N-ethyl-1H-indazole-3-carboxamide; 6-[(2-tert-butyl-7-oxo-2,4,6,7-tetrahydro-1'H-spiro[indazole-5,4'-piperidin]-1'-yl)carbonyl]-N-(2-methoxyethyl)-1H-indazole-3-carboxamide; 6-[(2-tert-butyl-7-oxo-2,4,6,7-tetrahydro-1'H-spiro[indazole-5,4'-piperidin]-1'-yl)carbonyl]-N-isopropyl-1H-indazole-3-carboxamide; 6-[(2-tert-butyl-7-oxo-2,4,6,7-tetrahydro-1'H-spiro[indazole-5,4'-piperidin]-1'-yl)carbonyl]-N-propyl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-cyclopropyl-1H-indole-3-carboxamide; 6-[(2-tert-butyl-7-oxo-2,4,6,7-tetrahydro-1'H-spiro[indazole-5,4'-piperidin]-1'-yl)carbonyl]-N-cyclobutyl-1H-indazole-3-carboxamide; 6-[(2-tert-butyl-7-oxo-2,4,6,7-tetrahydro-1'H-spiro[indazole-5,4'-piperidin]-1'-yl)carbonyl]-N-oxetan-3-yl-1H-indazole-3-carboxamide; 5-[(2-tert-butyl-7-oxo-2,4,6,7-tetrahydro-1'H-spiro[indazole-5,4'-piperidin]-1'-yl)carbonyl]-N-(2-methoxyethyl)-1H-indole-3-carboxamide; 5-[(2-tert-butyl-7-oxo-2,4,6,7-tetrahydro-1'H-spiro[indazole-5,4'-piperidin]-1'-yl)carbonyl]-N-methyl-1H-indole-3-carboxamide; 5-[(2-tert-butyl-7-oxo-2,4,6,7-tetrahydro-1'H-spiro[indazole-5,4'-piperidin]-1'-yl)carbonyl]-N-ethyl-1H-indole-3-carboxamide; and 6-[(2-tert-butyl-7-oxo-2,4,6,7-tetrahydro-1'H-spiro[indazole-5,4'-piperidin]-1'-yl)carbonyl]-N-cyclopropyl-1H-indole-3-carboxamide; or a pharmaceutically acceptable salt thereof.

Another aspect of the present invention is a pharmaceutical composition comprising an amount of a compound of Formula (I) as described in any of the embodiments; or a pharmaceutically acceptable salt thereof and a pharmaceutically acceptable excipient, diluent, or carrier. Preferably, the composition comprises a therapeutically effective amount of a compound of the present invention. The composition may also contain at least one additional pharmaceutical agent. Preferred agents include anti-diabetic agents and/or anti-obesity agents.

In yet another aspect of the present invention is a method for treating a disease, condition, or disorder mediated by the inhibition of acetyl-CoA carboxylase enzyme(s) in a mammal that includes the step of administering to a mammal, preferably a human, in need of such treatment a therapeutically effective amount of a compound of the present invention, or a pharmaceutically acceptable salt thereof or a pharmaceutical composition thereof.

Diseases, disorders, or conditions mediated by inhibitors of acetyl-CoA carboxylases include Type II diabetes and diabetes-related diseases, such as nonalcoholic fatty liver disease (NAFLD), hepatic insulin resistance, hyperglycemia, metabolic syndrome, impaired glucose tolerance, diabetic neuropathy, diabetic nephropathy, diabetic retinopathy, obesity, dyslipidemia, hypertension, hyperinsulinemia, and insulin resistance syndrome. Preferred diseases, disorders, or conditions include Type II diabetes, nonalcoholic fatty liver disease (NAFLD), hepatic insulin resistance, hyperglycemia, impaired glucose tolerance, obesity, and insulin resistance syndrome. More preferred are Type II diabetes, nonalcoholic fatty liver disease (NAFLD), hepatic insulin resistance, hyperglycemia, and obesity. Most preferred is Type II diabetes.

A preferred embodiment is a method for treating (e.g. delaying the progression or onset of) Type 2 diabetes and diabetes-related disorders in animals comprising the step of administering to an animal in need of such treatment a therapeutically effective amount of a compound of the present invention or a pharmaceutically acceptable salt thereof or a composition thereof.

A more preferred embodiment is a method for treating, or delaying the progression or onset of, Type 2 diabetes and diabetes-related disorders in a human comprising the step of administering to the human in need of such treatment a therapeutically effective amount of a compound of the present invention or a pharmaceutically acceptable salt thereof or a composition thereof.

A most preferred embodiment is a method for treating, or delaying the progression or onset of, Type 2 diabetes in a human comprising the step of administering to the human in need of such treatment a therapeutically effective amount of a compound of the present invention or a pharmaceutically acceptable salt thereof or a composition thereof.

Another preferred embodiment is a method for treating obesity and obesity-related disorders in animals comprising the step of administering to an animal in need of such treatment a therapeutically effective amount of a compound of the present invention or a pharmaceutically acceptable salt thereof or a composition thereof.

Another preferred embodiment is a method for treating obesity and obesity-related disorders in a human comprising the step of administering to the human in need of such treatment a therapeutically effective amount of a compound of the present invention or a pharmaceutically acceptable salt thereof or a composition thereof.

Yet another preferred embodiment is a method for treating nonalcoholic fatty liver disease (NAFLD) or hepatic insulin resistance in animals comprising the step of administering to an animal, in particular a human, in need of such treatment a therapeutically effective amount of a compound of the present invention or a pharmaceutically acceptable salt thereof or a composition thereof.

Yet another preferred embodiment is a method for treating nonalcoholic fatty liver disease (NAFLD) or hepatic insulin resistance in a human comprising the step of administering to the human in need of such treatment a therapeutically effective amount of a compound of the present invention or a pharmaceutically acceptable salt thereof or a composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

Another embodiment is the use of a compound of the present invention in the manufacture of a medicament for treating a disease, condition or disorder that is modulated by the inhibition of acetyl-CoA carboxylase enzyme(s).

Another embodiment is the use of a compound of the present invention in the manufacture of a medicament for treating a disease, condition or disorder that is modulated by the inhibition of acetyl-CoA carboxylase enzyme(s) wherein the disease, condition, or disorder is Type 2 diabetes, diabetes-related disorders, nonalcoholic fatty liver disease (NAFLD) or hepatic insulin resistance.

Another embodiment is the use of a compound of the present invention in the manufacture of a medicament for treating a disease, condition or disorder that is modulated by the inhibition of acetyl-CoA carboxylase enzyme(s) wherein the disease, condition, or disorder is Type 2 diabetes.

Another embodiment is the use the compound of Example 6, 14, or 25 in the manufacture of a medicament for treating a disease, condition or disorder that is modulated by the inhibition of acetyl-CoA carboxylase enzyme(s) wherein the disease, condition, or disorder is Type 2 diabetes, diabetes-related disorders, nonalcoholic fatty liver disease (NAFLD) or hepatic insulin resistance.

Another embodiment is the use of the compound of Example 6, 14, or 25 in the manufacture of a medicament for treating a disease, condition or disorder that is modulated by the inhibition of acetyl-CoA carboxylase enzyme(s) wherein the disease, condition, or disorder is Type 2 diabetes.

Another embodiment is the use of the compound of Example 6 in the manufacture of a medicament for treating a disease, condition or disorder that is modulated by the inhibition of acetyl-CoA carboxylase enzyme(s) wherein the disease, condition, or disorder is Type 2 diabetes.

Another embodiment is the use of the compound of Example 14 in the manufacture of a medicament for treating a disease, condition or disorder that is modulated by the inhibition of acetyl-CoA carboxylase enzyme(s) wherein the disease, condition, or disorder is Type 2 diabetes.

Another embodiment is the use of the compound of Example 25 in the manufacture of a medicament for treating a disease, condition or disorder that is modulated by the inhibition of acetyl-CoA carboxylase enzyme(s) wherein the disease, condition, or disorder is Type 2 diabetes.

DETAILED DESCRIPTION OF THE INVENTION

Definitions

The phrase "therapeutically effective amount" means an amount of a compound of the present invention or a pharmaceutically acceptable salt thereof that: (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the Acetyl-CoA carboxylases (ACC) enzyme(s) with compounds of the present invention.

The terms "mediated" or "mediating" or "mediate(s)", as used herein, unless otherwise indicated, refers to the (i) treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by inhibiting the Acetyl-CoA carboxylases (ACC) enzyme(s).

The term "compounds of the present invention" (unless specifically identified otherwise) refer to compounds of Formula (I) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

The terms "$(C_1-C_6)$alkyl" and "$(C_1-C_3)$alkyl" are alkyl groups of the specified number of carbons, from one to six or one to three carbons, respectively, which can be either straight chain or branched. For example, the term "$(C_1-C_3)$alkyl" has from one to three carbons and consists of methyl, ethyl, n-propyl and isopropyl. Alkoxy groups with a specified number of carbons are named in an analogous manner.

The term "$(C_1-C_3)$alkylene" are diradical $(C_1-C_3)$alkyl groups of from one to three carbons which can be either straight chain or branched. Representative examples of the term "$(C_1-C_3)$alkylene" include, but are not limited to, —$CH_2$—, —$CH_2CH_2$—, —$CH(CH_3)CH_2$—, —$CH_2CH_2(CH_3)$—, or —$CH_2CH_2CH_2$—.

The term "$(C_3-C_7)$cycloalkyl" means a cycloalkyl group with three to seven carbon atoms and consists of cyclopropyl, cyclobutyl, cyclopentyl, cyclohexyl and cycloheptyl or can be a bicyclo ring system such as bicycle[1.1.1]pentanyl. The term "halo" means fluoro, chloro, bromo or iodo.

The term "four to seven membered heterocyclyl" means a radical of a four to seven membered non-aromatic heterocycle. The point of attachment can be either through a carbon atom or a nitrogen atom. Non-limiting examples of these include oxetanyl, tetrahydrofuranyl, morpholinyl, azetidinyl, pyrrolodinyl, piperidinyl, piperazinyl and the like.

The terms indolyl, indazolyl, pyrrolopyridinyl, pyrazolopyridinyl, quinolinyl or benzoimidazolyl are radicals of the groups shown below and the point of attachment is on a carbon atom of that group.

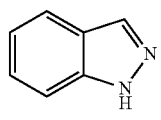
1H-indazole

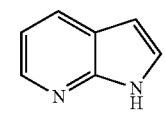
1H-pyrrolo[2,3-b]pyridine

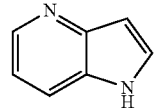
1H-pyrrolo[3,2-b]pyridine

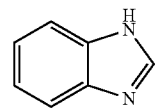
1H-benzo[d]imidazole

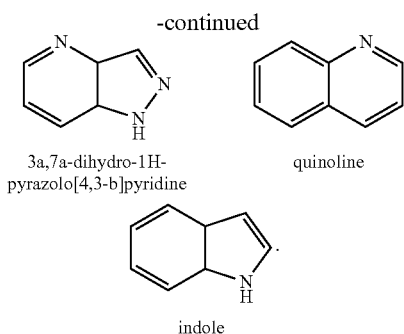

3a,7a-dihydro-1H-pyrazolo[4,3-b]pyridine quinoline indole

In one embodiment, the compound of Formula (I) is a N1 ACC inhibitor compound having the following structure:

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

The following reaction schemes, Reaction Schemes I through Reaction Scheme III, provide representative procedures that are used to prepare the compounds of Formula (I). It is to be understood that these reaction schemes are to be construed in a non-limiting manner and that reasonable variations of the depicted methods can be used to prepare the compounds of Formula (I).

Reaction Scheme I outlines the general procedures one could use to provide N1 ACC inhibitor compounds of the present invention having Formula Ia, which is a compound of Formula (I) in which $R^1$ is a $(C_1-C_6)$alkyl or $(C_3-C_7)$cycloalkyl and $R^2$ is indolyl, indazolyl, pyrrolopyridinyl, pyrazolopyridinyl, quinolinyl or benzoimidazolyl; wherein each $R^2$ group is optionally substituted with one to two substituents independently selected from a cyano, -L-C(O)$NR^4R^5$, -L-$NR^4R^5$, $(C_1-C_3)$alkyl, $(C_1-C_3)$alkoxy and halo; $R^3$ is hydrogen; L is a direct bond or —X$(C_1-C_3)$alkylene; X is a direct bond, O or S; and $R^4$ and $R^5$ are each independently hydrogen, $(C_1-C_3)$alkyl, $(C_3-C_7)$cycloalkyl or four to seven membered heterocyclyl wherein said $(C_1-C_3)$alkyl, $(C_3-C_7)$cycloalkyl or four to seven membered heterocyclyl is optionally substituted with one to three fluoro or $(C_1-C_3)$alkoxy.

REACTION SCHEME I

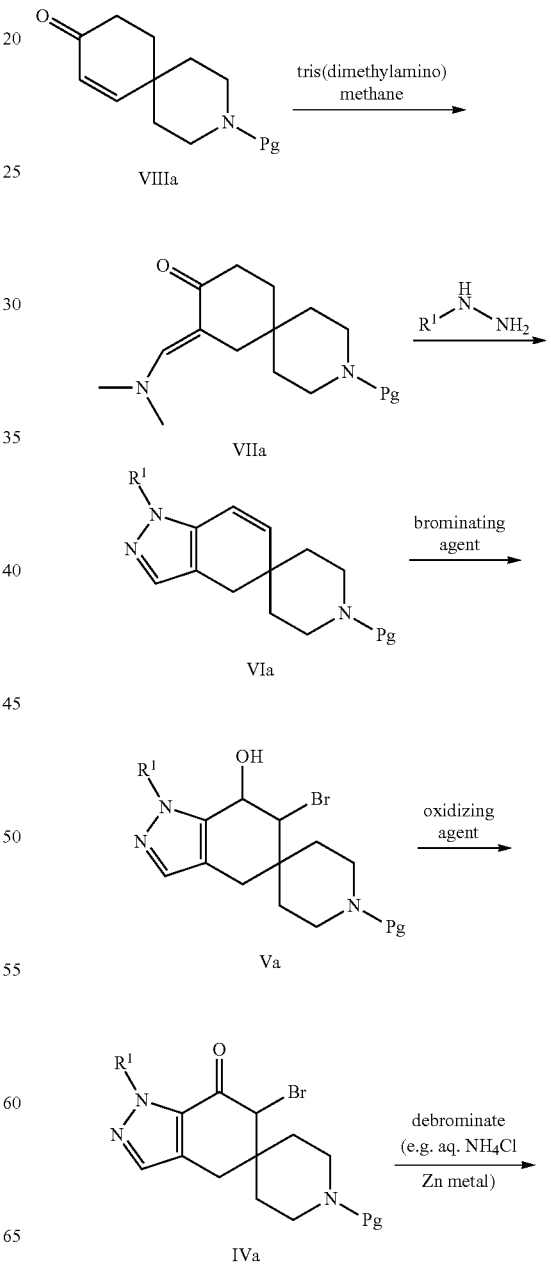

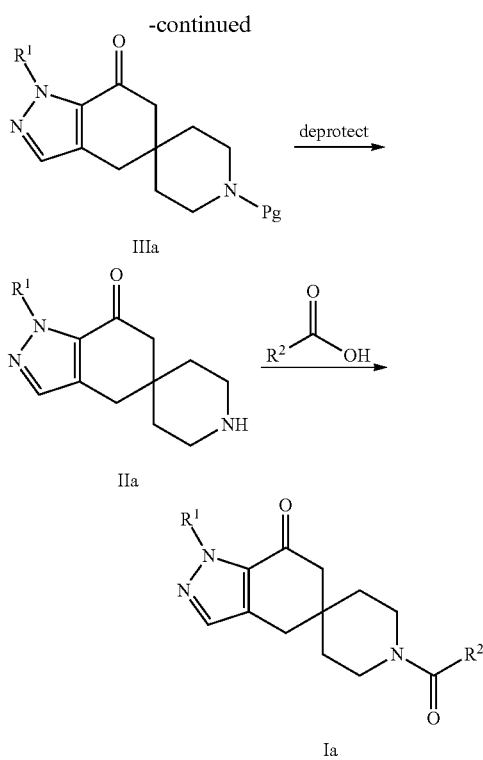

According to Scheme I, the compound of VIIa can be formed by reacting the compound of formula VIIIa wherein Pg represents an appropriate amine protecting group with tris(dimethylamino)methane in an appropriate solvent. The reaction can be carried out in an appropriate solvent such as toluene at an elevated temperature, such as reflux, for a period of 1 to 24 hours to provide the compound of formula VIIIa. The compound of formula VIa can be formed by reacting the compound of formula VIIIa with an appropriate alkyl or cycloalkyl hydrazine ($R_1NHNH_2$, such as t-butyl hydrazine, isopropyl hydrazine or bicycle[1.1.1]pentanyl hydrazine) in an appropriate solvent such as ethanol. For example, the compound of formula VIa can be formed by reacting VIIa with an appropriate alkyl hydrazine ($R_1NHNH_2$,) optionally in the presence of a base such as potassium carbonate ("$K_2CO_3$") in refluxing ethanol to provide the desired cyclized compound, at a temperature of about 20° C. to about 80° C. for about 2 to 24 hours.

The compound of formula Va can be formed by converting the compound of formula VIa to the corresponding hydroxy bromide derivative by reaction with an appropriate brominating reagent and water in an appropriate solvent. For example, the compound of formula Va can be formed by reacting the compound of formula VIa with N-bromosuccinimide (NBS) and water in tetrahydrofuran at room temperature for 1 hour to provide the corresponding hydroxy bromo derivative of formula Va. The compound of formula IVa can then be formed by oxidation of the compound of formula Va with an appropriate oxidizing agent in an appropriate solvent. For example, the compound of formula Va can be oxidized by treatment with Jones reagent in acetone at 0° C. to room temperature for a period of 15 minutes to 4 hours followed by extractive workup. The compound of formula IVa can then be debrominated by treatment with aqueous ammonium chloride and zinc metal in an appropriate solvent such as tetrahydrofuran for 15 minutes to 4 hours, typically at room temperature.

The compound of formula IIIa can then be deprotected to provide the free spiropiperidine derivative of formula IIa using standard methods which depend on which protecting group Pg has been employed. For example, when Pg represents BOC, standard strong acid deprotection conditions, such as 4N hydrochloric acid in dioxane or trifluoroacetic acid in an appropriate solvent such as dichloromethane, can be used to remove the BOC group. When Pg represents Cbz, hydrogenation over palladium on carbon in ethanol or treatment with a hydrogen source such as ammonium formate or 1-methyl-1,4-cyclohexadiene in the presence of palladium on carbon in ethanol or ethyl acetate can be employed to carry out the deprotection.

The spiropiperidine derivative of formula IIa can then be acylated by employing standard methods to provide the compound of formula Ia. For example, the compound (Ia) may then be formed using a standard peptide coupling reaction with the desired carboxylic acid ($R^2CO_2H$). For example, the spiropiperidine intermediate (IIa) and carboxylic acid ($R^2CO_2H$) may be coupled by forming an activated carboxylic acid ester, such as by contacting the carboxylic acid ($R^2CO_2H$) with a peptide coupling reagent, such as O-(7-azabenzotriazol-1-yl)-N,N,N',N'-tetramethyluronium hexafluorophosphate ("HATU") or 1-ethyl-3-(3-dimethylaminopropyl)carbodiimide hydrochloride ("EDC.HCl"), in the presence or absence of an activating agent, such as hydroxybenzotriazole ("HOBt") and in the presence of a suitable base, such as N,N-diisopropylethylamine ("DIEA"), triethylamine or N-methylmorpholine ("NMM"), in a suitable solvent such as THF and/or DMF, dimethylacetamide ("DMA") or dichloromethane and then contacting the activated carboxylic acid ester with the spiropiperidine derivative IIa to form a compound of formula Ia.

Reaction Scheme II outlines the general procedures one could use to provide N2 ACC inhibitor compounds of the present invention having Formula Ib, in which $R^1$ is a ($C_1$-$C_6$)alkyl or ($C_3$-$C_7$)cycloalkyl and $R^2$ is indolyl, indazolyl, pyrrolopyridinyl, pyrazolopyridinyl, quinolinyl or benzoimidazolyl; wherein each $R^2$ group is optionally substituted with one to two substituents independently selected from a cyano, -L-C(O)$NR^4R^5$, -L-$NR^4R^5$, ($C_1$-$C_3$)alkyl, ($C_1$-$C_3$)alkoxy and halo; $R^3$ is hydrogen; L is a direct bond or —X($C_1$-$C_3$)alkylene; X is a direct bond, O or S; and $R^4$ and $R^5$ are each independently hydrogen, ($C_1$-$C_3$)alkyl, ($C_3$-$C_7$)cycloalkyl or four to seven membered heterocyclyl wherein said ($C_1$-$C_3$) alkyl, ($C_3$-$C_7$)cycloalkyl or four to seven membered heterocyclyl is optionally substituted with one to three fluoro or ($C_1$-$C_3$)alkoxy.

REACTION SCHEME II

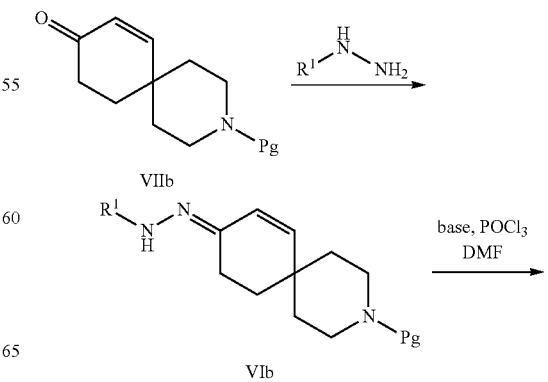

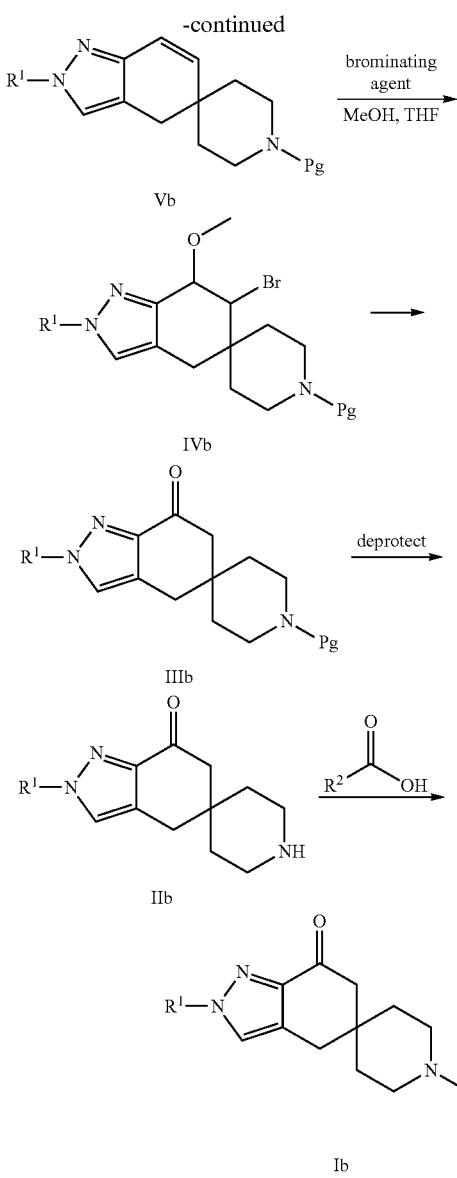

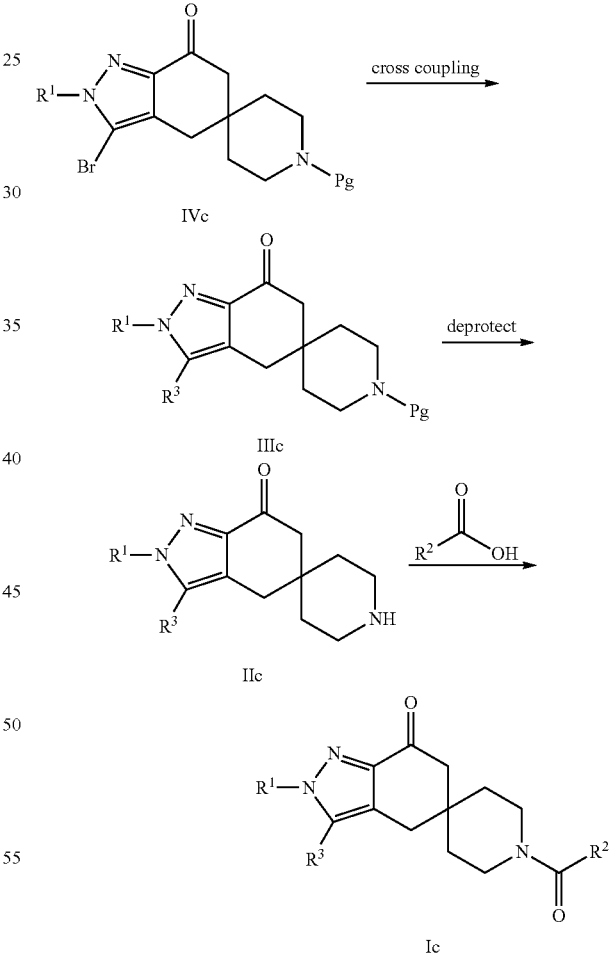

reaction with an appropriate brominating agent and methanol in an appropriate solvent such as tetrahydrofuran. For example, reaction of the compound Vb with N-bromosuccinimide in 20% methanol/tetrahydrofuran for 30 minutes to 4 hours at ambient temperature can provide the compound of formula IVb. Treatment of the compound of formula IVb with an appropriate base, such as potassium t-butoxide, in an appropriate solvent such as tetrahydrofuran for 15 minutes to 2 hours followed by acidification with an appropriate acid, such as 2N hydrochloric acid, can provide the compound of formula IIIb. Deprotection of the compound of formula IIIb, followed by coupling with the acid R2CO2H in the manner described previously in Reaction Scheme I provides the compound of formula Ib.

Reaction Scheme III outlines the general procedures one could use to provide N2 ACC inhibitor compounds of the present invention having Formula Ic, in which $R^1$ and $R^2$ are as previously and R3 is an alkyl group.

REACTION SCHEME III

According to Scheme II, reaction of the compound of formula VIIb with an appropriate hydrazine derivative $R^1$—$NHNH^2$ provides the compound of formula VIb. The reaction is typically carried out in an appropriate solvent such as ethanol at an elevated temperature such as 60° C. to reflux for a period of about 1 to 48 hours to provide the compound of formula VIb. When the hydrazine derivative $R^1$—$NHNH^2$ employed is in the form of its corresponding acid addition salt, such as a hydrochloride salt, it is to be appreciated that the compound of formula VIb formed may also exist as a salt. When the compound of formula VIb exists as the salt form, it is typically treated with an appropriate base, such as sodium bicarbonate, in an appropriate solvent, such as dichloromethane, for 15 minutes to 4 hours at ambient temperature prior to conversion to the compound of formula Vb. The compound of formula Vb is formed by first reacting phosphorous oxychloride with dimethylformamide at 0° C. then adding the compound of formula VIb and cyclizing it at an elevated temperature, such as 80° C. for a period of 1 to 24 hours. The compound of formula Vb is then converted to the corresponding methoxy bromo derivative of formula IVb by The compound of formula IIIc may be formed by palladium catalyzed cross-coupling of the bromide of formula IVc with an alkyl or alkenyl tributylstannane such as methyl tri-nbutylstannane or vinyl tri-nbutylstannane or allyl tri-nbutyl-stannane or a trialkyl boroxine such as trimethyl boroxine or trivinyl boroxine in the presence of a palladium catalyst such as tetrakis(triphenylphosphine) palladium(0) or a precatalyst and ligand combination such as palladium(II)acetate and 2-dicyclohexylphosphino-2',6'-dimethoxybiphenyl ("SPhos") and in the presence or absence of a base such as potassium carbonate in a protic solvent such as ethanol or t-amyl alcohol or an aprotic solvent such as tetrahydrofuran or dimethylformamide at a temperature of about 20° C. to about 100° C. for about 2 hours to about 18 hours or at a temperature of about 100° C. to about 150° C. for about 5 minutes to about 60 minutes under microwave heating. If a alkenyl trialkylstannane or alkenyl boroxine is utilized to install the $R^3$ group, reduction of the resulting olefin may be affected by hydrogenation over palladium on carbon in ethanol or treatment with a hydrogen source such as ammonium formate or 1-methyl-1,4-cyclohexadiene in the presence of palladium on carbon in ethanol or ethyl acetate.

The compound of formula IIIc may then be deprotected to provide the free spiropiperidine derivative of formula IIc using standard methods which depend on which protecting group Pg has been employed. For example, when Pg represents BOC, standard strong acid deprotection conditions. such as 4N hydrochloric acid in dioxane or trifluoroacetic acid in an appropriate solvent such as dichloromethane, can be used to remove the BOC group. When Pg represents Cbz, hydrogenation over palladium on carbon in ethanol or treatment with a hydrogen source such as ammonium formate or 1-methyl-1,4-cyclohexadiene in the presence of palladium on carbon in ethanol or ethyl acetate may be employed to carry out the deprotection.

The spiropiperidine derivative of formula IIc may then be acylated by employing standard methods to provide the compound of Formula Ic. For example, the compound Ic may then be formed using a standard peptide coupling reaction with the desired carboxylic acid ($R^2CO_2H$). For example, the spiropiperidine intermediate IIc and carboxylic acid ($R^2CO_2H$) may be coupled by forming an activated carboxylic acid ester, such as by contacting the carboxylic acid ($R^2CO_2H$) with a peptide coupling reagent, such as HATU or EDC.HCl, in the presence or absence of an activating agent, such as HOBt and in the presence of a suitable base, such as DIEA, triethylamine or NMM, in a suitable solvent such as THF and/or DMF, DMA or dichloromethane and then contacting the activated carboxylic acid ester with the spiropiperidine derivative IIc to form a compound of Formula Ic. Similar methodology can be employed to prepare the corresponding N1 analogues (where $R^1$ is on N1 of the pyrazole ring rather than on N2 as shown in Reaction Scheme III).

The compounds of the present invention may be isolated and used per se or in the form of their pharmaceutically acceptable salts. In accordance with the present invention, compounds with multiple basic nitrogen atoms can form salts with varying number of equivalents ("eq.") of acid. It will be understood by practitioners that all such salts are within the scope of the present invention.

Pharmaceutically acceptable salts, as used herein in relation to compounds of the present invention, include pharmaceutically acceptable inorganic and organic salts of the compound. These salts can be prepared in situ during the final isolation and purification of a compound, or by separately reacting the compound thereof, with a suitable organic or inorganic acid and isolating the salt thus formed. Representative salts include, but are not limited to, the hydrobromide, hydrochloride, hydroiodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylammonium, dimethylammonium, trimethylammonium, triethylammonium, ethylammonium, and the like. For additional examples see, for example, Berge, et al., J. Pharm. Sci., 66, 1-19 (1977).

Compounds of the present invention may exist in more than one crystal form. Polymorphs of compounds of Formula (I) and salts thereof (including solvates and hydrates) form part of this invention and may be prepared by crystallization of a compound of the present invention under different conditions. For example, using different solvents or different solvent mixtures for recrystallization; crystallization at different temperatures; various modes of cooling, ranging from very fast to very slow cooling during crystallization. Polymorphs may also be obtained by heating or melting a compound of the present invention followed by gradual or fast cooling. The presence of polymorphs may be determined by solid probe nuclear magnetic resonance (NMR) spectroscopy, infrared (IR) spectroscopy, differential scanning calorimetry, powder X-ray diffraction or such other techniques.

This invention also includes isotopically-labeled compounds, which are identical to those described by Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur and fluorine, such as $^2H$, $^3H$, $^{13}C$, $^{14}C$, $^{15}N$, $^{18}O$, $^{17}O$, $^{35}S$, $^{36}Cl$, $^{125}I$, $^{129}I$, and $^{18}F$ respectively. Certain isotopically-labeled compounds of the present invention, for example those into which radioactive isotopes such as $^3H$ and $^{14}C$ are incorporated, are useful in drug and/or substrate tissue distribution assays. Tritiated (i.e., $^3H$), and carbon-14 (i.e., $^{14}C$), isotopes are particularly preferred for their ease of preparation and detectability. Further, substitution with heavier isotopes such as deuterium (i.e., $^2H$), can afford certain therapeutic advantages resulting from greater metabolic stability, for example increased in vivo half-life or reduced dosage requirements and, hence, may be preferred in some circumstances. Isotopically labeled compounds of the present invention can generally be prepared by carrying out the procedures disclosed in the schemes and/or in the Examples below, by substituting a readily available isotopically labeled reagent for a non-isotopically labeled reagent.

The compounds of the present invention may contain stereogenic centers. These compounds may exist as mixtures of enantiomers or as pure enantiomers. Wherein a compound includes a stereogenic center, the compounds may be resolved into the pure enantiomers by methods known to those skilled in the art, for example by formation of diastereoisomeric salts which may be separated, for example, by crystallization; formation of stereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation.

Compounds of the present invention may exist in different stable conformational forms which may be separable. Torsional asymmetry due to restricted rotation about an asymmetric single bond, for example because of steric hindrance or ring strain, may permit separation of different conformers. The compounds of the present invention further include each conformational isomer of compounds of Formula (I) and mixtures thereof.

Compounds of the present invention are useful for treating diseases, conditions and/or disorders modulated by the inhibition of the acetyl-CoA carboxylases enzyme(s) (in particular, ACC1 and ACC2). Another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., for use in the preparing a medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The dissolution rate of poorly water-soluble compounds may be enhanced by the use of a spray-dried dispersion, such as those described by Takeuchi, H., et al. in "Enhancement of the dissolution rate of a poorly water-soluble drug (tolbutamide) by a spray-drying solvent deposition method and disintegrants" *J. Pharm. Pharmacol.*, 39, 769-773 (1987); and EP0901786 B1 (US2002/009494), incorporated herein by reference. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the present invention. The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of the acetyl-CoA carboxylases enzyme(s) in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of acetyl-CoA carboxylases enzyme(s).

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment (e.g., delaying the progression or onset) of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

In yet another aspect of the present invention is the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant ($p<0.05$) reduction in glucose serum levels.

In yet another aspect of the invention is the treatment of nonalcoholic fatty liver disease (NAFLD) and hepatic insulin resistance.

For a normal adult human having a body weight of about 100 kg, a dosage in the range of from about 0.001 mg to about 10 mg per kilogram body weight is typically sufficient, preferably from about 0.01 mg/kg to about 5.0 mg/kg, more preferably from about 0.01 mg/kg to about 1 mg/kg. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be combined with the compounds of the present invention include, for example, those described at page 30, line 20 through page 31, line 30 of WO 2011005611. The lipid lowering agents include bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR α agonists, FXR receptor modulators, LXR receptor modulators, lipoprotein synthesis inhibitors, rennin angiotensisn system inhibitors, PPAR d partial agonists, bile acid reabsorption inhibitors, PPAR γ agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin bound chromium and other agents that affect lipid composition.

Suitable anti-hypertensive agents that can be combined with the compounds of the present invention include, for example, those described at page 31, line 31 through page 32, line 18 of WO 2011005611. The anti-hypertensive agents include diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, α/β adrenergic blockers, alpha 1 blockers, alpha 2 agonists, aldosterone inhibitors, mineraocorticoid receptor inhibitors, renin inhibitors and angiopoietin-2-binding agents.

Suitable anti-diabetic agents include an acetyl-CoA carboxylase- (ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, N,N-9924, TTP-054, a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (Jul. 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4)359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTR5), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents (some of which may also act as anti-diabetic agents as well) include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $\beta_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists such as velneperit), $PYY_{3-36}$ (including analogs thereof), BRS3 modulator, mixed antagonists of opiod receptor subtypes, thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, histamine 3 antagonists or inverse agonists, neuromedin U agonists, MTP/ApoB inhibitors (e.g., gut-selective MTP inhibitors, such as dirlotapide, JTT130, Usistapide, SLx4090), opioid antagonist, mu opioid receptor modulators, including but not limited to GSK1521498, MetAp2 inhibitors, including but not limited to ZGN-433, agents with mixed modulatory activity at 2 or more of glucagon, GIP and GLP1 receptors, such as MAR-701 or ZP2929, norepinephrine transporter inhibitors, cannabinoid-1-receptor antagonist/inverse agonists, ghrelin agonists/antagonists, oxyntomodulin and analogs, monoamine uptake inhibitors, such as but not limited to tesofensine, an orexin antagonist, combination agents (such as bupropion plus zonisamide, pramlintide plus metreleptin, bupropion plus naltrexone, phentermine plus topiramate), and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e] azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine. Preferably, compounds of the present invention and combination therapies are administered in conjunction with exercise and a sensible diet.

All of the recited U.S. patents and publications (including all technical bulletins referenced in the Examples) are incorporated herein by reference in their entireties.

The Examples set forth herein below are for illustrative purposes only. The compositions, methods, and various parameters reflected herein are intended only to exemplify various aspects and embodiments of the invention, and are not intended to limit the scope of the claimed invention in any way.

EXAMPLES

The compounds and intermediates described below were named using the naming convention provided with Chemdraw Ultra, Version 11.0.1 (CambridgeSoft Corp., Cambridge Mass.). The naming convention provided with Chemdraw Ultra, Version 11.0.1 are well known by those skilled in the art and it is believed that the naming convention provided with Chemdraw Ultra, Version 11.0.1 generally comports with the IUPAC (International Union for Pure and Applied Chemistry) recommendations on Nomenclature of Organic Chemistry and the CAS Index rules. Unless noted otherwise, all reactants were obtained commercially. All of the references cited herein below are incorporated by reference.

Flash chromatography was performed according to the method described by Still et al., J. Org. Chem., 1978, 43, 2923.

All Biotage® purifications, discussed herein, were performed using Biotage® SNAP columns containing KP-SIL silica (40-63 μM, 60 Angstroms) (Biotage AB; Uppsala, Sweden).

All Combiflash® purifications, discussed herein, were performed using a CombiFlash® Companion system (Teledyne Isco; Lincoln, Nebr.) utilizing packed RediSep® silica columns Mass Spectra were recorded on a Waters (Waters Corp.; Milford, Mass.) Micromass Platform II spectrometer. Unless otherwise specified, mass spectra were recorded on a Waters (Milford, Mass.) Micromass Platform II spectrometer.

Proton NMR chemical shifts are given in parts per million downfield from tetramethylsilane and were recorded on a Varian Unity 300, 400 or 500 MHz (megaHertz) spectrometer (Varian Inc.; Palo Alto, Calif.). NMR chemical shifts are given in parts per million downfield from tetramethylsilane (for proton) or fluorotrichloromethane (for fluorine).

HPLC retention times were measured using the following methods: Method A: column: Waters Atlantis dC18 4.6×50 mm, 5 μm; mobile phase A: 0.05% TFA in water (v/v); mobile phase B: 0.05% TFA in acetonitrile (v/v); gradient: 95% A/5% B linear to 5% A/95% B in 4.0 minutes, hold at 5% A/95% B for 5.0 minutes; flow rate: 2.0 mL/minute.

The preparations described below were used in the synthesis of compounds exemplified in the following examples.

The following starting materials are available from the corresponding sources 6-bromo-1H-indole-3-carbonitrile—Indofine Chemical Company, Inc. (Hillsborough, N.J., USA)
5-bromo-1H-indole-3-carbonitrile—Indofine Chemical Company, Inc. (Hillsborough, N.J., USA)
6-bromo-1H-indole-2-carboxamide—Aurora Fine Chemicals LLC (San Diego, Calif., USA)
methyl 3-iodo-1H-indazole-5-carboxylate—Anichem LLC (North Brunswick, N.J., USA)
1H-pyrrolo[3,2-b]pyridine-6-carboxylic acid—ACS Scientific Inc. (Metuchen, N.J., USA)
methyl 1H-pyrrolo[3,2-b]pyridine-6-carboxylate—ACS Scientific Inc. (Metuchen, N.J., USA)
methyl 1H-pyrrolo[2,3-b]pyridine-5-carboxylate—Anichem LLC (North Brunswick, N.J., USA)
5-(methoxycarbonyl)-1H-indole-2-carboxylic acid—Bepharm Ltd. (Shanghai, China)
methyl 3-bromo-1H-pyrazolo[3,4-b]pyridine-5-carboxylate—MolBridge (Plainsboro, N.J., USA)
ethyl 2-bromo-1H-pyrrolo[2,3-b]pyridine-5-carboxylate—American Custom Chemicals Corp. (San Diego, Calif., USA)
5-bromo-1H-indazole-3-carboxylic acid—Anichem LLC (North Brunswick, N.J., USA)
6-methoxyquinoline-3-carboxylic acid—BioBlocks, Inc. (San Diego, Calif., USA); prepared as described by A. Hanna-Elias et al. *Austr. J. Chem.* 2009, 62, 150-156
2-aminoquinoline-6-carboxylic acid—Princeton Biomolecular Research Inc. (Monmouth Junction, N.J., USA)
5-bromo-2-nitrobenzaldehyde—Oakwood Products, Inc. (West Columbia, S.C., USA)
ethyl quinoline-7-carboxylate—ASW MedChem, Inc. (New Brunswick, N.J., USA)

Preparation of Intermediates and Starting Materials

Intermediate 1: 1-isopropyl-4,6-dihydrospiro[indazole-5,4'-piperidin]-7(1H)-one, shown below, was prepared as follows:

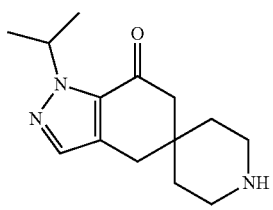 [SMILES: CC(C)n1ncc2c1C(=O)CC1(CCNCC1)C2]

Step 1. tert-butyl 9-oxo-3-azaspiro[5.5]undec-7-ene-3-carboxylate

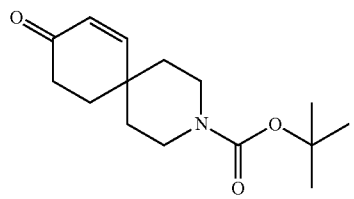 [SMILES: CC(C)(C)OC(=O)N1CCC2(C=CC(=O)CC2)CC1]

Methyl vinyl ketone (146 mL, 1.78 mol) was added to a solution of tert-butyl 4-formylpiperidine-1-carboxylate (375 g, 1.76 mol) in tetrahydrofuran (18 L). The reaction mixture was cooled to −5° C. and a solution of potassium hydroxide in ethanol (3N, 0.243 L) was added dropwise over 10 minutes. The reaction mixture was allowed to warm to room temperature and stirred for 16 hours. Cyclohexane (10 L) was added and the solution was washed with saturated sodium chloride (3×10 L). The organic layer was concentrated to an oil. This oil was dissolved in 2 L of 80:20 cyclohexane/ethyl acetate and filtered through Celite® to remove the insoluble material. The filtrate was purified via flash column chromatography (30% ethyl acetate/hexanes) to afford the product as an oil. The oil was triturated in hexanes to afford the title compound as a colorless solid (131 g, 28%).

Step 2. 1-isopropyl-4,6-dihydrospiro[indazole-5,4'-piperidin]-7(1H)-one

A solution of tert-butyl 9-oxo-3-azaspiro[5.5]undec-7-ene-3-carboxylate (250 g) and tris(dimethylaminomethane) (325 mL) in toluene (1.9 L) was heated at reflux for 4 hours. The mixture was distilled and concentrated to a minimum stirring volume (110° C.) and then toluene (1.9 L) was added. The reaction was redistilled to a minimum stirring volume and cooled to room temperature. Toluene (1.8 L) and isopropyl hydrazine hydrochloride (135 g) were added and the solution was heated to reflux for 5 hours. The reaction was cooled to room temperature and was washed with citric acid (10% aqueous, 2×150 mL) and water (200 mL). The organic layer was then distilled to a minimum stirring volume. Methanol (2 L) was added and distilled to a minimum stirring volume. This was repeated with methanol (2 L). The solution was redissolved in methanol (2.5 L) and N-bromosuccinimide (176 g) was added in one portion. The solution was stirred at 23° C. for 2 hours. Aqueous sodium thiosulfate solution (5 wt %, 0.5 L) was added and the mixture was stirred for 15 minutes. The reaction mixture was concentrated via distillation (45° C., 210 mm Hg) to ~0.5 L and then 2-methyl tetrahydrofuran (2.5 L) was added. After stirring for 15 minutes the aqueous layer was discarded. The organic layer was concentrated to 0.2 L and tetrahydrofuran (0.5 L) was added. To the mixture was added a potassium tert-butoxide solution in tetrahydrofuran (1.9 L, 1 M solution). The solution was heated to 60° C. and stirred for 1 hour. After cooling to room temperature, aqueous hydrochloric acid (1 N, 2.2 L) was added over 20 minutes. The mixture was stirred at room temperature for 20 minutes, and then the layers were allowed to separate. The aqueous layer was removed and back extracted with ethyl acetate (1.75 L). The combined organic layers were washed with water (1 L) and concentrated via distillation (4 L solvent removed). Ethyl acetate (1.8 L) was added and the solution was concentrated to a minimum stirring volume. Ethyl acetate (3 L) and methanol (0.8 L) were added and the solution was cooled to 0° C. Acetyl chloride (401 mL) was added dropwise over 20 minutes and the solution was stirred at 0° C. for 4 hours. The precipitate was collected by filtration under nitrogen. The filtrate was washed with ethyl acetate (0.5 L) and dried in a vacuum oven at 40° C. to afford the title compound as an off-white solid (241 g). +ESI (M+H) 248.4; $^1$H NMR (400 MHz, CD$_3$OD, δ): 7.43 (s, 1 H), 5.32-5.42 (m, 1 H), 3.15-3.25 (m, 4 H), 2.89 (s, 2 H), 2.64 (s, 2 H), 1.69-1.90 (m, 4 H), 1.37-1.45 (m, 6 H).

Intermediate 2: 2-tert-butyl-4,6-dihydrospiro[indazole-5,4'-piperidin]-7(2H)-one hydrochloride salt, shown below, was prepared as follows:

Step 1. benzyl 9-oxo-3-azaspiro[5.5]undec-7-ene-3-carboxylate

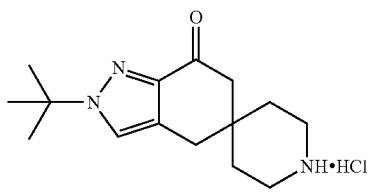

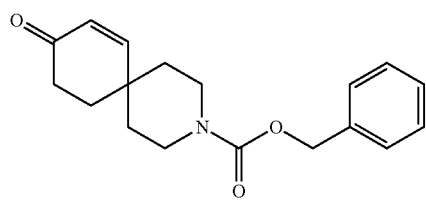 [SMILES: O=C1C=CC2(CC1)CCN(C(=O)OCc1ccccc1)CC2]

To a benzene (700 mL) solution of benzyl 4-formylpiperidine-1-carboxylate (90.0 g, 364 mmol) in a 2 L 3-neck flask fitted with a Dean-Stark trap was added p-toluenesulfonic acid (6.92 g, 36.4 mmol) with stirring. The reaction was heated to 70° C., and 3-buten-2-one (61.8 mL, 753 mmol) was added. The mixture was heated at reflux for 24 hours collecting expelled water in the trap. The reaction was cooled to room temperature and washed with 500 mL saturated aqueous sodium bicarbonate. The organic phase was dried over sodium sulfate, filtered and concentrated. The resultant dark brown oil was taken up in 200 mL dichloromethane and filtered through a silica pad (600 mL silica), eluting with 2 L heptane followed by 3 L 50% ethyl acetate/heptane and then 3 L ethyl acetate. Fractions containing clean product were combined and concentrated to yield 68.1 g of the title compound as a thick brown oil. The fractions containing impure product were combined and concentrated and purified by flash column chromatography (10-80% ethyl acetate/heptanes) to yield an additional 23.6 g of the title compound as a thick brown oil. A combined yield of 91.7 g, (94.1%) was realized. $^1$H NMR (400 MHz, CDCl$_3$, δ): 7.27-7.43 (m, 5 H), 6.79 (d, J=10.3 Hz, 1 H), 5.95 (d, J=10.3 Hz, 1 H), 5.13 (s, 2 H), 3.56-3.71 (m, 2 H), 3.39-3.55 (m, 2 H), 2.38-2.50 (m, 2 H), 1.96 (t, J=6.7 Hz, 2 H), 1.52-1.70 (m, 4 H).

Step 2. (E)-benzyl 9-(2-tert-butylhydrazono)-3-azaspiro[5.5]undec-7-ene-3-carboxylate hydrochloride salt

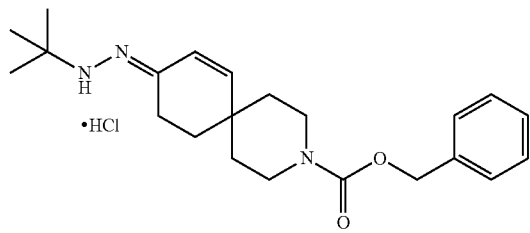 [SMILES: CC(C)(C)N/N=C1/C=CC2(CC1)CCN(C(=O)OCc1ccccc1)CC2 ; Cl]

Benzyl 9-oxo-3-azaspiro[5.5]undec-7-ene-3-carboxylate (4.89 g, 16.3 mmol) was dissolved in ethanol (60 mL) and tert-butylhydrazine hydrochloride (2.44 g, 19.6 mmol) was added. The mixture was heated at reflux for 4 hours and then stirred at 60° C. for 48 hours. The reaction was cooled to room temperature and concentrated under reduced pressure to give a tan oil which solidified upon standing to yield 6.60 g (99%) of the title compound as a tan solid. +ESI (M+H) 370.3; $^1$H NMR (400 MHz, CDCl$_3$, δ): 7.26-7.42 (m, 5 H), 6.46 (d, J=10.0 Hz, 1 H), 6.26 (br. s., 1 H), 5.08-5.16 (m, 2 H), 3.43-3.58 (m, 4 H), 3.19 (s, 2 H), 1.78 (s, 2 H), 1.44-1.63 (m, 4 H), 1.17-1.30 (m, 9 H).

Step 3. benzyl 2-tert-butyl-2,4-dihydrospiro[indazole-5,4'-piperidine]-1'-carboxylate

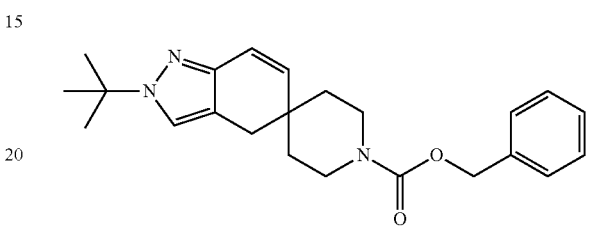

(E)-benzyl 9-(2-tert-butylhydrazono)-3-azaspiro[5.5]undec-7-ene-3-carboxylate hydrochloride salt (8.00 g, 19.7 mmol) was dissolved in dichloromethane (100 mL) and treated with sodium bicarbonate (1.70 g, 19.7 mmol). The solution was stirred for 30 minutes and was then filtered and concentrated under reduced pressure to yield (E)-benzyl 9-(2-tert-butylhydrazono)-3-azaspiro[5.5]undec-7-ene-3-carboxylate. A 250 mL round bottom flask was charged with dimethylformamide (80 mL) and cooled to 0° C. Phosphorous oxychloride (5.51 mL, 59.1 mmol) was added dropwise over 2 minutes, and the solution was stirred for 30 minutes at 0° C. To this solution was added the (E)-benzyl 9-(2-tert-butylhydrazono)-3-azaspiro[5.5]undec-7-ene-3-carboxylate in dimethylformamide (15 mL) and the reaction was heated at 80° C. for 18 hours. The reaction was cooled to room temperature and concentrated under reduced pressure. The resultant oil was dissolved in ethyl acetate (500 mL) and washed with brine (2×150 mL). The aqueous layer was extracted with an additional 100 mL ethyl acetate. The combined organic layers were dried over sodium sulfate, filtered and concentrated. The resultant oil was purified by flash column chromatography (10-80% ethyl acetate/heptane) to yield 4.89 g (65%) of the title compound as a pale yellow oil. +ESI (M+H) 380.0; $^1$H NMR (400 MHz, CDCl$_3$, δ): 7.25-7.36 (m, 5 H), 7.18 (s, 1 H), 6.57 (d, J=10.0 Hz, 1 H), 5.86 (d, J=10.0 Hz, 1 H), 5.12 (s, 2 H), 3.51-3.69 (m, 2 H), 3.36-3.53 (m, 2 H), 2.58 (s, 2 H), 1.59-1.74 (m, 2 H), 1.52-1.58 (m, 9 H), 1.41-1.53 (m, 2 H).

Step 4. benzyl 6-bromo-2-tert-butyl-7-methoxy-2,4,6,7-tetrahydrospiro[indazole-5,4'-piperidine]-1'-carboxylate

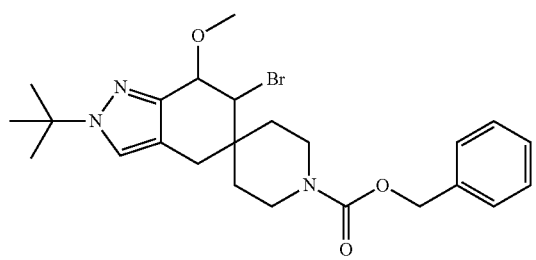 [SMILES: COC1c2nn(C(C)(C)C)cc2CC2(CCN(C(=O)OCc3ccccc3)CC2)C1Br]

Benzyl 2-tert-butyl-2,4-dihydrospiro[indazole-5,4'-piperidine]-1'-carboxylate (560 mg, 1.48 mmol) was dissolved in a 20% methanol/tetrahydrofuran mixture (25 mL). N-bromosuccinimide (315 mg, 1.77 mmol) was added and the mixture was stirred for 30 minutes. The mixture was concentrated under reduced pressure. The resultant oil was partitioned between ethyl acetate (50 mL) and water (50 mL). The organic phase was dried over sodium sulfate, filtered and concentrated. The resultant oil was purified by flash column chromatography (10-80% ethyl acetate/heptane) to yield 538 mg (73%) of the title compound as a colorless oil. $^1$H NMR (400 MHz, CDCl$_3$, δ): 7.27-7.43 (m, 6 H), 5.12 (s, 2 H), 4.74 (d, J=2.7 Hz, 1 H), 4.41 (d, J=2.5 Hz, 1 H), 3.60-3.84 (m, 2 H), 3.54-3.61 (m, 3 H), 3.14-3.39 (m, 2 H), 2.59 (s, 2 H), 1.86 (br. s., 1 H), 1.69 (br. s., 3 H), 1.51-1.60 (m, 9 H).

Step 5. benzyl 2-tert-butyl-7-oxo-2,4,6,7-tetrahydrospiro[indazole-5,4'-piperidine]-1'-carboxylate

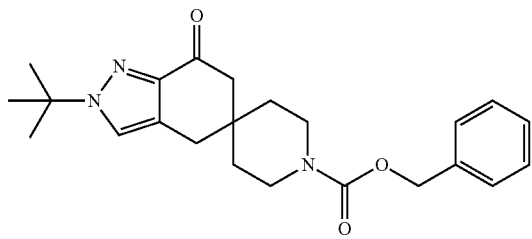 [SMILES: CC(C)(C)n1cc2c(n1)C(=O)CC1(CCN(C(=O)OCc3ccccc3)CC1)C2]

Benzyl 6-bromo-2-tert-butyl-7-methoxy-2,4,6,7-tetrahydrospiro[indazole-5,4'-piperidine]-1'-carboxylate (150 mg, 0.31 mmol) was dissolved in 5 mL tetrahydrofuran and treated with potassium tert-butoxide (0.61 mL, 0.61 mmol, 1 M tetrahydrofuran) and stirred for 30 minutes. Aqueous 2 N HCl (5 mL) was added and the mixture was stirred for 15 minutes at room temperature. The mixture was then diluted with 50 mL water and extracted with ethyl acetate (50 mL). The organic layer was dried over sodium sulfate, filtered and concentrated. The residue was purified by flash column chromatography (10-80% ethyl acetate/heptanes) to yield 86 mg (71%) of the title compound as a clear oil. +ESI (M+H) 396.5; $^1$H NMR (400 MHz, CDCl$_3$, δ): 7.38 (s, 1 H), 7.27-7.35 (m, 5 H), 5.11 (s, 2 H), 3.48 (t, J=5.8 Hz, 4 H), 2.71 (s, 2 H), 2.57 (s, 2 H), 1.57-1.66 (m, 9 H), 1.47-1.59 (m, 4 H).

Step 6. 2-tert-butyl-4,6-dihydrospiro[indazole-5,4'-piperidin]-7(2 H)-one hydrochloride salt Benzyl 2-tert-butyl-7-oxo-2,4,6,7-tetrahydrospiro[indazole-5,4'-piperidine]-1'-carboxylate (441 mg, 1.12 mmol) was dissolved in methanol (15 mL) and treated with ammonium formate (217 mg, 3.34 mmol) and palladium on carbon (50 mg, 10% Pd, 50% H$_2$O). The reaction was stirred 2 hours at room temperature and the catalyst then removed by filtration. The filtrate was concentrated under reduced pressure. The resultant colorless solid was taken up in ethyl acetate (20 mL) and treated with 0.5 M HCl in diethyl ether (1 mL). The mixture was stirred for 30 minutes and concentrated under reduced pressure. The resultant colorless solid was triturated with heptane (20 mL) to yield 265 mg (80%) of the title compound as a colorless solid. +ESI (M+H) 262.1; $^1$H NMR (400 MHz, CD$_3$OD, δ): 7.74 (s, 1 H), 3.20 (t, J=6.1 Hz, 4 H), 2.88 (s, 2 H), 2.64 (s, 2H), 1.67-1.91 (m, 4 H), 1.55-1.63 (m, 9 H).

Intermediate 3: 2-(bicyclo[1.1.1]pentan-1-yl)-4,6-dihydrospiro[indazole-5,4'-piperidin]-7(2 H)-one, shown below, was prepared as follows:

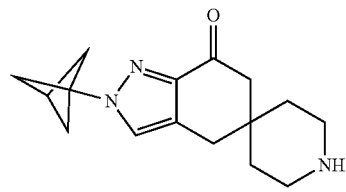 [SMILES: O=C1CC2(CCNCC2)Cc2cn(C34CC(C3)C4)nc21]

Step 1: di-tert-butyl 1-(bicyclo[1.1.1]pentan-1-yl)hydrazine-1,2-dicarboxylate

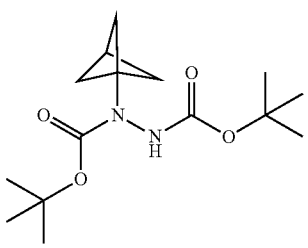 [SMILES: CC(C)(C)OC(=O)NN(C(=O)OC(C)(C)C)C12CC(C1)C2]

Tris(2,2,6,6-tetramethyl-3,5-heptanedionato)manganese (III) (281 mg, 0.460 mmol) was dissolved in 2-propanol (100 mL) in a 1 L 3-necked flask equipped with addition funnel, gas inlet, and thermometer. The solution was cooled to −15° C. under nitrogen. Di-tert-butyl azodicarboxylate (8.11 g, 34.5 mmol) and phenylsilane (2.9 mL, 23 mmol) were dissolved in dichloromethane (100 mL) and this resulting orange solution was added to the above cooled solution dropwise over 10 minutes, maintaining the internal temperature at approximately −10° C. A solution of [1.1.1]propellane (Journal of the American Chemical Society (2001), 123(15), 3484-3492) (50 mL, 23 mmol, 0.46 M in pentane) was added to the reaction mixture in one portion at −15° C. The reaction was stirred at −15° C. for 30 minutes. The cold bath was removed and the reaction was allowed to warm to room temperature and stir for 4 hours. The reaction was concentrated and purification by flash column chromatography (5-20% ethyl acetate/heptanes) gave the title compound (6.38 g, 93%) as a clear oil which solidified upon standing. −ESI (M−H) 297.4; $^1$H NMR (400 MHz, CDCl$_3$, δ): 6.26 (br. s., 1H), 2.37 (s, 1H), 2.02 (s, 6H), 1.45 (s, 18H).

Step 2: bicyclo[1.1.1]pentan-1-ylhydrazine hydrochloride

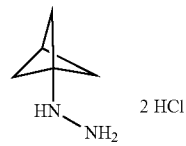

To a solution of di-tert-butyl 1-(bicyclo[1.1.1]pentan-1-yl)hydrazine-1,2-dicarboxylate (6.38 g, 21.4 mmol) in ethyl acetate (20 mL) was added 4 N hydrochloric acid in 1,4-dioxane (53.5 mL, 214 mmol). The reaction was stirred at room temperature for 18 hours. The reaction was concentrated and the solid triturated with heptanes to yield the title compound (3.24 g, 89%) as a white solid. $^1$H NMR (400 MHz, DMSO-d$_6$, δ): 2.42 (s, 1 H), 1.80 (s, 6 H).

Step 3: benzyl 2-(bicyclo[1.1.1]pentan-1-yl)-7-oxo-2,4,6,7-tetrahydrospiro[indazole-5,4'-piperidine]-1'-carboxylate

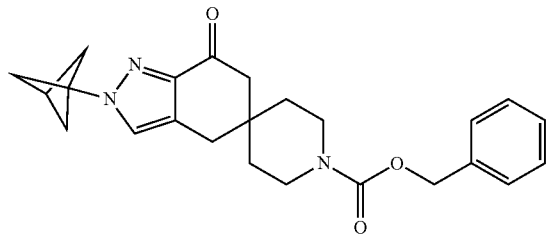 [SMILES: O=C1CC2(CCN(C(=O)OCc3ccccc3)CC2)Cc2cn(C34CC(C3)C4)nc21]

The title compound was prepared by a method analogous to that described in Steps 1-5 of Intermediate 2, using bicyclo[1.1.1]pentan-1-ylhydrazine hydrochloride in Step 2. +ESI (M+H) 406.1; $^1$H NMR (400 MHz, CDCl$_3$, δ): 7.28-7.36 (m, 5 H), 7.27 (s, 1 H), 5.10 (s, 2 H), 3.44-3.50 (m, 4 H), 2.70 (s, 2 H), 2.62 (s, 1 H), 2.56 (s, 2 H), 2.31 (s, 6 H), 1.53 (d, J=2.5 Hz, 4H).

Step 4: 2-(bicyclo[1.1.1]pentan-1-yl)-4,6-dihydrospiro[indazole-5,4'-piperidin]-7(2H)-one To a solution of benzyl 2-(bicyclo[1.1.1]pentan-1-yl)-7-oxo-2,4,6,7-tetrahydrospiro[indazole-5,4'-piperidine]-1'-carboxylate (150 mg, 0.37 mmol) in ethyl acetate (10 mL) was added 10% palladium on carbon (1 mg) and 1-methylcyclohexane-1,4-diene (0.1 mL, 0.9 mmol). The reaction was heated to 80° C. and stirred for 2 hours. The reaction was cooled to room temperature and filtered through Celite. The filtrate was concentrated to give the title compound (100 mg, 100%) as an oil. +ESI (M+H) 272.4; $^1$H NMR (400 MHz, CDCl$_3$, δ): 7.26 (s, 1 H), 2.82 (dd, J=6.63, 4.49 Hz, 4 H), 2.69 (s, 2 H), 2.60 (s, 1 H), 2.56 (s, 2 H), 2.30 (s, 6 H), 1.47-1.55 (m, 4 H).

Intermediate 4: 1-tert-butyl-4,6-dihydrospiro[indazole-5,4'-piperidin]-7(1H)-one, shown below, was prepared as follows:

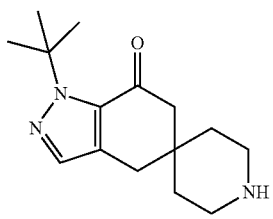 [SMILES: CC(C)(C)n1ncc2c1C(=O)CC1(CCNCC1)C2]

Step 1. benzyl 10-((dimethylamino)methylene)-9-oxo-3-azaspiro[5.5]undec-7-ene-3-carboxylate

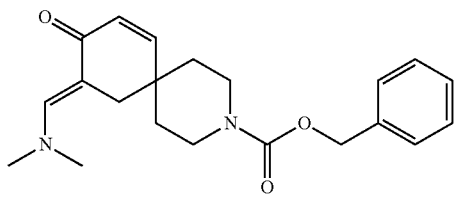 [SMILES: CN(C)/C=C1\CC2(C=CC1=O)CCN(C(=O)OCc1ccccc1)CC2]

Benzyl 9-oxo-3-azaspiro[5.5]undec-7-ene-3-carboxylate (15.2 g, 51 mmol) was dissolved in toluene (180 mL) and tris(dimethylamino)methane (22.2 g, 27 mmol) was added. The reaction was heated to reflux for 5 hours and then allowed to cool to room temperature and stir overnight. The reaction solution was concentrated in vacuo to provide the title compound (18.0 g, 100%). +APCI (M+H) 354.6; $^1$H NMR (400 MHz, CDCl$_3$, δ): 7.49 (s, 1 H), 7.28-7.40 (m, 5 H), 6.59 (d, J=10.16 Hz, 1 H), 6.01 (d, J=9.97 Hz, 1 H), 5.13 (s, 2 H), 3.52-3.66 (m, 2 H), 3.39-3.52 (m, 2 H), 3.07 (s, 6 H), 2.74 (s, 2 H), 1.58-1.73 (m, 2 H), 1.41-1.58 (m, 2 H).

Step 2. benzyl 1-tert-butyl-1,4-dihydrospiro[indazole-5,4'-piperidine]-1'-carboxylate

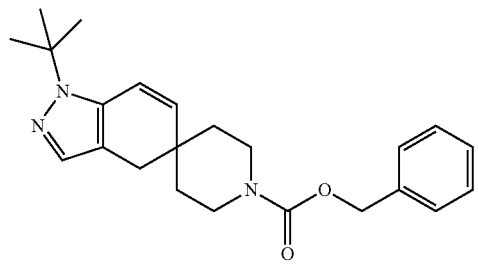 [SMILES: CC(C)(C)n1ncc2c1C=CC1(CCN(C(=O)OCc3ccccc3)CC1)C2]

Benzyl 10-((dimethylamino)methylene)-9-oxo-3-azaspiro[5.5]undec-7-ene-3-carboxylate (59.2 g, 167 mmol) was dissolved in ethanol (835 mL). To the solution was added acetic acid (20 mL, 345 mmol) and tert-butylhydrazine hydrochloride (29.1 g, 234 mmol). The reaction was heated to reflux for 1 hour. The reaction was cooled to room temperature and concentrated to an orange oil. Purification by flash column chromatography (20-40% ethyl acetate/heptanes) afforded the title compound (50 g, 79%) as a pale yellow solid. +ESI (M+H) 380.5; $^1$H NMR (400 MHz, CDCl$_3$, δ): 7.26-7.40 (m, 5 H), 7.17 (s, 1 H), 6.66 (d, J=9.95 Hz, 1 H), 5.77 (d, J=10.15 Hz, 1 H), 5.12 (s, 2 H), 3.38-3.64 (m, 4 H), 2.58 (s, 2 H), 1.60 (s, 12 H), 1.50 (br. s., 1 H).

Step 3. benzyl 6-bromo-1-tert-butyl-7-hydroxy-1,4,6,7-tetrahydrospiro[indazole-5,4'-piperidine]-1'-carboxylate

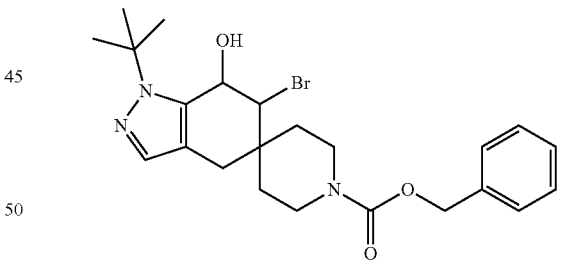

Benzyl 1-tert-butyl-1,4-dihydrospiro[indazole-5,4'-piperidine]-1'-carboxylate (50 g, 132 mmol) was dissolved in tetrahydrofuran (1 L). To the reaction was added N-bromosuccinimide (24.6 g, 138 mmol) and water (250 mL). The reaction was stirred for 1 hour at room temperature. The reaction was partitioned between ethyl acetate and water. The phases were separated and the organic phase was washed 2 times with water and once with saturated aqueous sodium chloride. The organic phase was dried over magnesium sulfate, filtered, and concentrated in vacuo. The residue was crystallized from diethylether to afford the title compound (60.7 g, 97%) as a cream-colored solid. +ESI (M+H) 476.5; $^1$H NMR (400 MHz, CDCl$_3$,δ): 7.28-7.36 (m, 5 H), 7.27 (s, 1 H), 5.23 (t, J=4.68 Hz, 1 H), 5.12 (s, 2 H), 4.24 (d, J=4.49 Hz, 1 H), 3.87 (br. s., 2 H), 3.12 (br. s., 2 H), 2.79 (d, J=16.00 Hz, 2 H), 2.59 (d, J=15.80 Hz, 2 H), 1.95 (br. s., 1 H), 1.66 (s, 11 H), 1.58 (br. s., 1 H).

Step 4. benzyl 6-bromo-1-tert-butyl-7-oxo-1,4,6,7-tetrahydrospiro[indazole-5,4'-piperidine]-1'-carboxylate

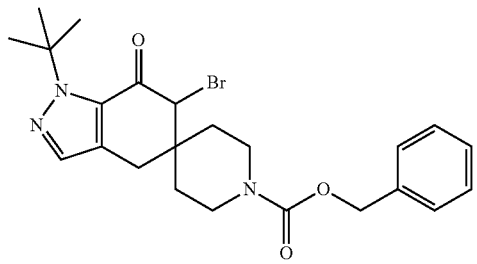 [SMILES: CC(C)(C)n1ncc2c1C(=O)C(Br)C1(CCN(C(=O)OCc3ccccc3)CC1)C2]

Benzyl 6-bromo-1-tert-butyl-7-hydroxy-1,4,6,7-tetrahydrospiro[indazole-5,4'-piperidine]-1'-carboxylate (57.9 g, 122 mmol) was dissolved in acetone (1 L) and cooled to 0° C. in an ice bath. To the solution was added Jones Reagent (122 mL) (Fillion, E. *Tetrahedron Letters* 2004, 46, 1091-1094). The ice bath was removed and the reaction was allowed to warm to room temperature and stir for 45 minutes. Saturated aqueous sodium bicarbonate was added until gas evolution ceased and the pH reached 7. The resulting mixture was filtered through a pad of Celite®, rinsing with ethyl acetate. The filtrate layers were separated and the aqueous layer was extracted with ethyl acetate. The combined organic extracts were washed twice with water, once with saturated aqueous sodium chloride, dried over magnesium sulfate, filtered and concentrated. The residue was crystallized from ethyl acetate/heptanes to afford the title compound (50.4 g, 87%). +ESI (M+H) 474.5; $^1$H NMR (400 MHz, CDCl$_3$, δ): 7.32 (d, J=9.38 Hz, 6 H), 5.11 (s, 2 H), 4.24 (s, 1 H), 3.58-3.84 (m, 2 H), 3.16-3.41 (m, 2 H), 2.67-2.91 (m, 2 H), 1.80 (br. s., 1 H), 1.61-1.76 (m, 11 H), 1.52-1.61 (m, 1 H).

Step 5. benzyl 1-tert-butyl-7-oxo-1,4,6,7-tetrahydrospiro[indazole-5,4'-piperidine]-1'-carboxylate

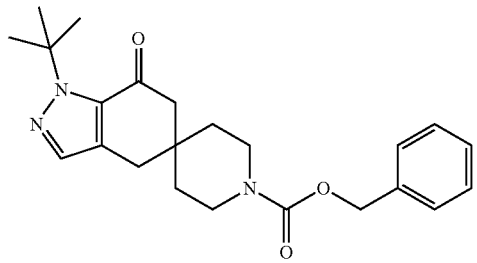 [SMILES: CC(C)(C)n1ncc2c1C(=O)CC1(CCN(C(=O)OCc3ccccc3)CC1)C2]

To a solution of benzyl 6-bromo-1-tert-butyl-7-oxo-1,4,6,7-tetrahydrospiro[indazole-5,4'-piperidine]-1'-carboxylate (50.4 g, 106 mmol) in tetrahydrofuran (600 mL), was added saturated aqueous ammonium chloride (600 mL) and zinc powder (20.8 g, 319 mmol). The reaction was stirred for 30 minutes at room temperature. The reaction was filtered through Celite®. The phases of the filtrate were separated and the organic phase was washed with water and saturated aqueous sodium chloride. The organics were dried over magnesium sulfate, filtered, and concentrated to provide a foam. The foam was triturated once with ethyl acetate/heptanes and once with diethylether to afford the title compound (40.4 g, 96%) as a white solid. +ESI (M+H) 396.5; $^1$H NMR (400 MHz, CDCl$_3$, δ): 7.24-7.38 (m, 6H), 5.11 (s, 2 H), 3.36-3.61 (m, 4 H), 2.74 (s, 2 H), 2.54 (s, 2 H), 1.64 (s, 9 H), 1.51 (br. s., 4 H).

Step 6. 1-tert-butyl-4,6-dihydrospiro[indazole-5,4'-piperidin]-7(1H)-one

A solution of benzyl 1-tert-butyl-7-oxo-1,4,6,7-tetrahydrospiro[indazole-5,4'-piperidine]-1'-carboxylate (46.6 g, 118 mmol) in ethanol (730 mL) was added to 10% palladium on carbon (9.4 g). To this mixture was added 1-methyl-1,4-cyclohexadiene (90 mL, 769 mmol). The reaction was stirred at reflux for 2 hours. The reaction was cooled to room temperature and filtered through Celite®. The filtrate was concentrated in vacuo to give a gray solid. The solid was dissolved in ethyl acetate (150 mL) and to this solution was added 4 M hydrochloric acid in 1,4-dioxane (35 mL). The resulting precipitate was collected by filtration and dried under vacuum to afford the title compound (34 g, 97%) as a white solid. +ESI (M+H) 262.5; $^1$H NMR (400 MHz, CD$_3$OD, δ): 7.34 (s, 1 H) 3.12-3.25 (m, 4 H) 2.90 (s, 2 H) 2.66 (s, 2 H) 1.67-1.85 (m, 4 H) 1.62 (s, 9 H).

Intermediate 5: 1-(bicyclo[1.1.1]pentan-1-yl)-4,6-dihydrospiro[indazole-5,4'-piperidin]-7(1H)-one hydrochloride, shown below, was prepared as follows:

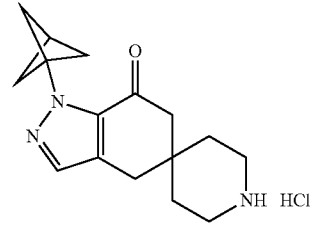 [SMILES: O=C1CC2(CCNCC2)Cc2cnn(C34CC(C3)C4)c21 ; Cl]

Step 1: benzyl 1-(bicyclo[1.1.1]pentan-1-yl)-1,4-dihydrospiro[indazole-5,4'-piperidine]-1'-carboxylate

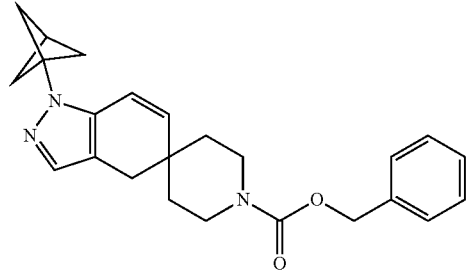 [SMILES: O=C(OCc1ccccc1)N1CCC2(C=Cc3c(cnn3C34CC(C3)C4)C2)CC1]

To a solution of benzyl 9-oxo-3-azaspiro[5.5]undec-7-ene-3-carboxylate (543 mg, 1.81 mmol) in toluene (15 mL) was added tris(dimethylamino)methane (0.47 mL, 2.7 mmol). The reaction was heated to reflux and stirred for 4 hours. The reaction was cooled to room temperature, diluted with ethyl acetate (50 mL), and washed with water (50 mL). The organic layer was dried over sodium sulfate, filtered, and concentrated. The resulting yellow oil was taken up in toluene (15 mL) and bicyclo[1.1.1]pentan-1-ylhydrazine hydrochloride (310 mg, 1.81 mmol) was added. The mixture was heated to reflux and stirred for 18 hours. The reaction was cooled to room temperature, diluted with ethyl acetate (50 mL), washed with water (50 mL) and 1 M aqueous citric acid (50 mL). The organic layer was dried over sodium sulfate, filtered, and concentrated. Purification by flash column chromatography gave 2 regioisomeric products.

benzyl 1-(bicyclo[1.1.1]pentan-1-yl)-1,4-dihydrospiro[indazole-5,4'-piperidine]-1'-carboxylate (365 mg, 52%): +APCI (M+H) 390.5; $^1$H NMR (400 MHz, CDCl$_3$, δ): 7.33-7.36 (m, 5 H), 7.22 (s, 1 H), 6.51 (d, J=10.1 Hz, 1 H), 5.81 (d, J=9.9 Hz, 1 H), 5.12 (s, 2 H), 3.42-3.59 (m, 4 H), 2.59 (s, 3 H), 2.35 (s, 6 H), 1.43-1.68 (m, 4 H).

benzyl 2-(bicyclo[1.1.1]pentan-1-yl)-2,4-dihydrospiro[indazole-5,4'-piperidine]-1'-carboxylate (85 mg, 12%): +APCI (M+H) 390.5; $^1$H NMR (400 MHz, CDCl$_3$, δ): 7.33-7.36 (m, 5 H), 7.08 (d, J=0.8 Hz, 1 H), 6.56 (d, J=10.0 Hz, 1 H), 5.91 (d, J=10.0 Hz, 1 H), 5.12 (s, 2 H), 3.40-3.62 (m, 4 H), 2.57 (s, 3 H), 2.26 (s, 6 H), 1.41-1.68 (m, 4 H).

Step 2: benzyl 1-(bicyclo[1.1.1]pentan-1-yl)-7-oxo-1,4,6,7-tetrahydrospiro[indazole-5,4'-piperidine]-1'-carboxylate

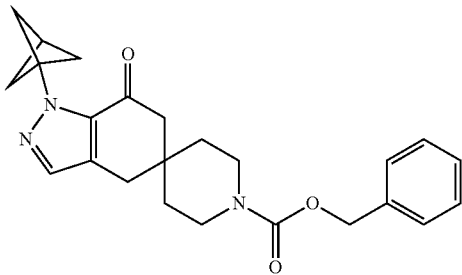 [SMILES: O=C1CC2(CCN(C(=O)OCc3ccccc3)CC2)Cc2cnn(C34CC(C3)C4)c21]

To a solution of benzyl 1-(bicyclo[1.1.1]pentan-1-yl)-1,4-dihydrospiro[indazole-5,4'-piperidine]-1'-carboxylate (340 mg, 0.87 mmol) in 3:1 tetrahydrofuran:water (10 mL) was added N-bromosuccinimide (155 mg, 0.87 mmol). The reaction was stirred at room temperature for 45 minutes. The reaction was diluted with ethyl acetate (50 mL), washed with 0.5 N aqueous sodium hydroxide (25 mL) and saturated aqueous sodium thiosulfate (25 mL). The organic layer was dried over sodium sulfate, filtered, and concentrated. The resulting oil was taken up in dichloromethane (5 mL) and treated with activated 4 Å molecular sieves (500 mg) and tetrapropylammonium perruthenate (16 mg, 0.04 mmol). The slurry was treated with N-methylmorpholine-N-oxide (243 mg, 1.75 mmol) in acetonitrile (5 mL). The reaction was stirred at room temperature for 2 hours. The reaction was filtered through Celite and the filtrate was concentrated. The residue was purified by flash column chromatography (7-60% ethyl acetate/heptanes) to yield a clear oil. The oil was taken up in tetrahydrofuran (5 mL) and treated with saturated aqueous ammonium chloride (5 mL) and zinc dust (171 mg, 2.62 mmol). The mixture was stirred at room temperature for 30 minutes. The reaction was diluted with water (50 mL) and extracted with ethyl acetate (2×30 mL). The combined organics were washed with brine, dried over sodium sulfate, filtered, and concentrated. Purification by flash column chromatography (7-60% ethyl acetate/heptanes) gave the title compound (148 mg, 42%) as a white solid. $^1$H NMR (400 MHz, CDCl$_3$, δ): 7.34 (m, 6 H), 5.13 (s, 2 H), 3.51 (m, 4 H), 2.75 (s, 2 H), 2.59 (s, 1 H), 2.54 (s, 2 H), 2.41 (s, 6 H), 1.56 (m, 4 H).

Step 3: 1-(bicyclo[1.1.1]pentan-1-yl)-4,6-dihydrospiro[indazole-5,4'-piperidin]-7(1H)-one hydrochloride The title compound was prepared by a method analogous to that described in Step 6 of Intermediate 4.

Intermediate 6: 3-carbamoyl-1H-indazole-6-carboxylic acid, shown below, was prepared as follows:

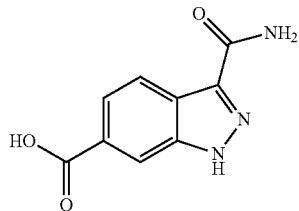 [SMILES: NC(=O)c1n[nH]c2cc(C(=O)O)ccc12]

Step 1. methyl 1H-indazole-6-carboxylate

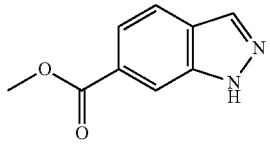

To a solution of 1H-indazole-6-carboxylic acid (3.00 g, 18.5 mmol) in N,N-dimethylformamide (46 mL) was added sodium carbonate (2.06 g, 19.4 mmol), followed by iodomethane (2.75 g, 1.21 mL, 19.4 mmol) dropwise. The mixture was stirred at room temperature overnight. The mixture was poured into half saturated sodium bicarbonate and extracted with ethyl acetate three times. The combined organic layers were washed with brine, dried over sodium sulfate, filtered and concentrated in vacuo to afford a brown oil. This residue was purified by flash column chromatography (12-100% ethyl acetate/heptanes) to afford methyl 1H-indazole-6-carboxylate as a yellow solid (2.95 g, 90%). $^1$H NMR (400 MHz, CDCl$_3$, δ): 10.40 (br. s., 1 H), 8.26 (s, 1 H), 8.13 (s, 1 H), 7.84 (d, J=8.4 Hz, 1 H), 7.79 (d, J=8.4 Hz, 1 H), 3.96 (s, 3 H).

Step 2. methyl 3-iodo-1H-indazole-6-carboxylate

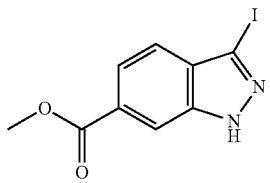

To a solution of methyl 1H-indazole-6-carboxylate (865 mg, 4.91 mmol) in N,N-dimethylformamide (12 mL) was added potassium hydroxide (840 mg, 3.05 mmol) followed by iodine (1.54 g, 5.9 mmol). The mixture was stirred at room temperature for 3 hours. Sodium bisulfate (30 mL of 5% aqueous) was added and the mixture was extracted with ethyl acetate twice. The combined organic layers were washed with brine, dried over sodium sulfate, filtered and concentrated in vacuo. The residue was purified via flash column chromatography (5-65% ethyl acetate/heptanes) to afford methyl 3-iodo-1H-indazole-6-carboxylate as a colorless solid (1.16 g, 78%). $^1$H NMR (400 MHz, DMSO-d$_6$, δ): 13.84 (s, 1 H), 8.13 (s, 1 H), 7.72 (d, J=8.4 Hz, 1 H), 7.54 (d, J=8.6 Hz, 1 H), 3.87 (s, 3 H).

Step 3. methyl 3-cyano-1H-indazole-6-carboxylate

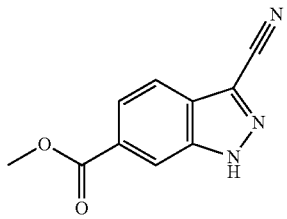

A mixture of methyl 3-iodo-1H-indazole-6-carboxylate (3.0 g, 9.9 mmol), zinc dust (400 mg, 6.11 mmol), zinc cyanide (2.0 g, 17.0 mmol), [1,1'-bis(diphenylphosphino)ferrocene]-dichloropalladium(II), complex with dichloromethane (1.15 g, 1.41 mmol), and copper (I) iodide (1.90 g, 9.97 mmol) in dimethylacetamide (55 mL) was purged with nitrogen for 15 minutes. The mixture was stirred at 120° C. for 15 hours. The reaction mixture was cooled, diluted with ethyl acetate (250 mL), and filtered through Celite, rinsing with ethyl acetate (100 mL). To the filtrate was added ~400 mL of a solution of saturated aqueous ammonium chloride and concentrated ammonium hydroxide (prepared by adding ammonium hydroxide to a saturated aqueous solution of ammonium chloride until pH=8). The mixture was stirred for 1 hour. The layers were then separated. The organic layer was washed with water and brine, dried over sodium sulfate, filtered and concentrated in vacuo. To the residue was added methanol (40 mL) and the mixture was stirred overnight. The mixture was filtered and the solid was dried in vacuo to give methyl 3-cyano-1H-indazole-6-carboxylate as a tan solid (1.47 g, 73%). $^1$H NMR (400 MHz, DMSO-d$_6$, δ): 13.40 (br. s., 1 H), 8.25 (s, 1 H), 7.94 (d, J=8.6 Hz, 1 H), 7.83 (d, J=8.4 Hz, 1 H), 3.88 (s, 3 H).

Step 4. 3-carbamoyl-1H-indazole-6-carboxylic acid

To a solution of methyl 3-cyano-1H-indazole-6-carboxylate (254 mg, 1.26 mmol) in methanol (12 mL) at 0° C. was added a cold solution of urea hydrogen peroxide (1.22 g, 12.6 mmol) in sodium hydroxide (12.6 mL 1M in water, 12.6 mmol). The yellow solution was stirred at room temperature overnight. The mixture was concentrated in vacuo to remove methanol. The pH of the resulting residue was adjusted to ~4 with 1N hydrochloric acid. A precipitate formed. The mixture was filtered and the solid was dried to afford 3-carbamoyl-1H-indazole-6-carboxylic acid as a brown solid (82 mg, 32%). $^1$H NMR (400 MHz, DMSO-d$_6$, δ): 13.84 (s, 1 H), 13.04 (br. s., 1 H), 8.20 (d, J=8.4 Hz, 1 H), 8.13-8.16 (m, 1 H), 7.77 (br. s., 1 H), 7.74 (dd, J=8.6, 1.4 Hz, 1 H), 7.38 (br. s., 1 H).

Intermediate 7: 3-carbamoyl-1H-indole-6-carboxylic acid, shown below, was prepared as follows:

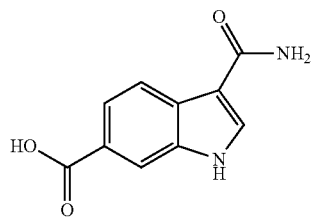 [SMILES: NC(=O)c1c[nH]c2cc(C(=O)O)ccc12]

Step 1. 3-cyano-1H-indole-6-carboxylic acid ethyl ester

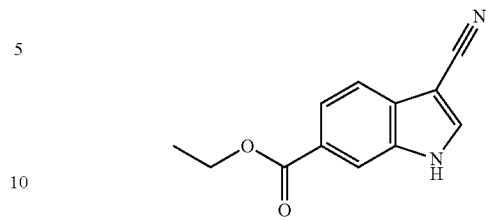

To a solution of 6-bromo-1H-indole-3-carbonitrile (328 mg, 1.48 mmol) in ethanol (5 mL) in a 500 mL Parr bottle was added sodium acetate (370 mg, 4.47 mmol) and [1,1'-bis(diphenylphosphino)ferrocene]dichloropalladium(II), complex with dichloromethane (242 mg, 0.297 mmol). The reaction vessel was purged with nitrogen and evacuated three times and then was filled with 30 psi carbon monoxide. The reaction mixture was heated to 70° C., increasing the pressure within the vessel to 45 psi. The reaction was agitated at 70° C. for 24 hours. The reaction mixture was cooled to room temperature. The mixture was filtered through Celite, rinsing with ethanol. The filtrate was concentrated under reduced pressure and diluted with dichloromethane. The remaining solids were filtered off and the filtrate was concentrated. The residue was purified by flash column chromatography (20-80% ethyl acetate/heptanes) to give 3-cyano-1H-indole-6-carboxylic acid ethyl ester (142 mg, 45%). –APCI (M–H) 213.4; $^1$H NMR (400 MHz, DMSO-d$_6$, δ): 12.50 (br. s., 1 H), 8.45 (s, 1 H), 8.16 (s, 1 H), 7.82 (dd, J=8.4, 1.4 Hz, 1 H), 7.73 (d, J=8.4 Hz, 1 H), 4.32 (q, J=7.0 Hz, 2 H), 1.33 (t, J=7.0 Hz, 3 H).

Step 2. 3-carbamoyl-1H-indole-6-carboxylic acid

A suspension of 3-cyano-1H-indole-6-carboxylic acid ethyl ester (100 mg, 1.4 mmol) in methanol (1.12 mL) was added to a solution of urea hydrogen peroxide (453 mg, 4.67 mmol) in 2.5 M sodium hydroxide (1.12 mL, 2.80 mmol) at 0° C. The suspension was allowed to warm to room temperature and was stirred overnight. The reaction was concentrated under reduced pressure. Water was added and the solution was acidified with 3 N aqueous hydrochloric acid to pH=2. A precipitate formed. The reaction mixture was stirred for 1 minute at room temperature and was then filtered to give an orange solid. Additional urea hydrogen peroxide (453 mg) in 2.5 M sodium hydroxide and methanol was added and the mixture was stirred for 2 hours. The reaction was concentrated, diluted with water, acidified to pH=3 and filtered. The solid was washed with water and heptanes and was dried in a vacuum oven to give 3-carbamoyl-1H-indole-6-carboxylic acid as a solid (66.5 mg, 70%). –ESI (M–1) 203.1; $^1$H NMR (400 MHz, DMSO-d$_6$, δ): 12.45 (br. s., 1 H), 11.78 (br. s., 1 H), 8.83 (d, J=1.6 Hz, 1 H), 8.09 (d, J=2.9 Hz, 1 H), 7.73 (dd, J=8.6, 1.8 Hz, 1 H), 7.51 (br. s., 1 H), 7.45 (d, J=8.4 Hz, 1 H), 6.89 (br. s., 1 H).

Intermediate 8: 3-carbamoyl-1H-indazole-5-carboxylic acid, shown below, was prepared as follows:

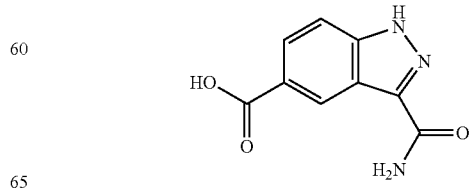

Step 1. methyl 3-cyano-1H-indazole-5-carboxylate

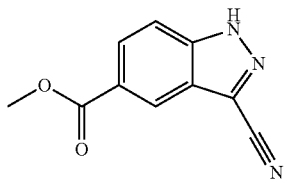

Methyl 3-iodo-1H-indazole-5-carboxylate (30.7 g, 102 mmol), zinc cyanide (20.3 g, 173 mmol), zinc dust (4.05 g, 61.9 mmol), [1,1'-bis(diphenylphosphino)ferrocene]-dichloropalladium(II), complex with dichloromethane (12 g, 15 mmol), and copper (I) iodide (19.7 g, 103 mmol) were combined in a 1 L round bottom flask. N,N-dimethylacetamide (500 mL) was added and the reaction mixture was purged with nitrogen for 10 minutes. The reaction was heated to 120° C. for 1 hour. The reaction was cooled to room temperature and was diluted with ethyl acetate (1 L), and allowed to stir for 20 minutes. The reaction mixture was filtered through a plug of Celite, rinsing with 500 mL ethyl acetate. The filtrate was added to a solution of saturated ammonium chloride and concentrated ammonium hydroxide (2 L) (prepared by adding ammonium hydroxide to a saturated aqueous solution of ammonium chloride until pH=8) and the biphasic solution was stirred vigorously for 1 hour. The resulting emulsion was filtered through a small pad of Celite. The layers were separated and the aqueous was extracted two additional times with ethyl acetate (1.1 L), each time filtering the resulting emulsion through Celite. The combined organic layers were washed with water (2×900 mL) and brine (900 mL), dried over sodium sulfate, filtered and concentrated. To the crude was added methanol (100 mL) and the mixture was stirred for 20 minutes. The resulting precipitate was filtered off and washed with methanol (10 mL). The filtrate was concentrated to give the title compound (13.2 g, 65%) as a solid. −ESI (M−H) 200.0; $^1$H NMR (400 MHz, DMSO-$d_6$, δ): 8.43-8.45 (m, 1 H), 8.05 (dd, J=8.8, 1.6 Hz, 1 H), 7.85 (dd, J=8.9, 0.9 Hz, 1 H), 3.88 (s, 3 H).

Step 2. 3-carbamoyl-1H-indazole-5-carboxylic acid

A suspension of methyl 3-cyano-1H-indazole-5-carboxylate (50.0 g, 249 mmol) in methanol (1 L) was cooled to 10° C. A solution of urea hydrogen peroxide (241 g, 2.49 mol) in sodium hydroxide (1 L of 2.5 N) and water (100 mL) was added dropwise, maintaining an internal temperature below 25° C. When the addition was complete, the ice bath was removed and the reaction was allowed to stir at room temperature for 16 hours. A small amount of unreacted starting material was observed by HPLC. The reaction was cooled to 15° C. and additional urea hydrogen peroxide (50 g) was added portionwise. Vigorous bubbling was noted. The reaction was allowed to stir for another 2 hours. The crude reaction was filtered to remove the solids present and the filtrate was concentrated to remove the methanol. The remaining solution was cooled in an ice bath and 6 N hydrochloric acid (420 mL) was added dropwise to adjust the pH to 4. The solution was stirred for 20 minutes and the resulting tan solid was collected by filtration and dried to give 57.2 g of crude product. To the crude was added acetonitrile (700 mL) and dichloromethane (700 mL) and the mixture was stirred at room temperature for 1 hour. The solid was collected by filtration, washed with 1:1 acetonitrile:dichloromethane (400 mL) and dried to give the title compound (39.5 g, 77%) as a tan solid. +ESI (M+H) 206.1; $^1$H NMR (DMSO-$d_6$, δ): 13.81 (s, 1 H), 12.85 (br. s., 1 H), 8.82 (d, J=0.8 Hz, 1 H), 7.93 (dd, J=8.8, 1.6 Hz, 1 H), 7.79-7.85 (m, 1 H), 7.64 (d, J=8.6 Hz, 1 H), 7.44 (s, 1 H).

Intermediate 9: 3-carbamoyl-1H-pyrrolo[3,2-b]pyridine-6-carboxylic acid, shown below, was prepared as follows:

Step 1. benzyl 1H-pyrrolo[3,2-b]pyridine-6-carboxylate

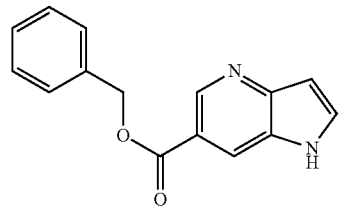 [SMILES: O=C(OCc1ccccc1)c1cnc2cc[nH]c2c1]

To a solution of 1H-pyrrolo[3,2-b]pyridine-6-carboxylic acid (1.37 g, 8.45 mmol) in N,N-dimethylformamide (55 mL) was added cesium carbonate (2.79 g, 8.56 mmol) and benzyl bromide (1.05 mL, 8.64 mmol). The reaction was allowed to stir at room temperature for 17 hours. Additional cesium carbonate (500 mg, 1.54 mmol) and benzyl bromide (0.186 mL, 1.53 mmol) were added, and the reaction was stirred for another 4 hours. The reaction was then quenched with water and diluted with ethyl acetate. The layers were separated and the aqueous was extracted with ethyl acetate three times. The combined organics were washed with water and brine, dried over sodium sulfate, filtered, and concentrated. Purification by flash column chromatography (0-100% ethyl acetate/heptanes) gave the title compound (1.42 g, 67%). +ESI (M+H) 253.3; $^1$H NMR (400 MHz, DMSO-$d_6$, δ): 11.68 (br. s., 1 H), 8.93 (d, J=2.0 Hz, 1 H), 8.33 (dd, J=2.0, 1.0 Hz, 1 H), 7.93 (t, J=3.0 Hz, 1 H), 7.51 (m, 2 H), 7.41 (m, 3 H), 6.68 (ddd, J=3.1, 2.0, 1.0 Hz, 1 H), 5.40 (s, 2 H).

Step 2. benzyl 3-bromo-1H-pyrrolo[3,2-b]pyridine-6-carboxylate

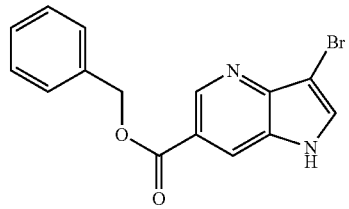 [SMILES: O=C(OCc1ccccc1)c1cnc2c(Br)c[nH]c2c1]

To a 0° C. solution of benzyl 1H-pyrrolo[3,2-b]pyridine-6-carboxylate (830 mg, 3.29 mmol) in N,N-dimethylformamide (19 mL) was added N-bromosuccinimide (609 mg, 3.42 mmol). The reaction was allowed to gradually warm to room temperature and stir over the weekend. The reaction was diluted with ethyl acetate and washed successively with saturated aqueous sodium thiosulfate, saturated aqueous sodium bicarbonate, water, and brine. The organics were dried over sodium sulfate, filtered, and concentrated to give the title compound (1.08 g, quantitative). +ESI (M+1+H) 333.0; $^1$H NMR (400 MHz, DMSO-$d_6$, δ): 12.06 (br. s., 1 H), 8.99 (d, J=1.8 Hz, 1 H), 8.37 (d, J=2.0 Hz, 1 H), 8.14 (d, J=2.9 Hz, 1 H), 7.52 (m, 2 H), 7.41 (m, 3 H), 5.41 (s, 2 H).

Step 3. 3-carbamoyl-1H-pyrrolo[3,2-b]pyridine-6-carboxylic acid

The title compound was prepared by a method analogous to that described in Steps 3-4 for Intermediate 6, using benzyl 3-bromo-1H-pyrrolo[3,2-b]pyridine-6-carboxylate. +ESI (M+H) 206.2; $^1$H NMR (400 MHz, DMSO-$d_6$, δ): 12.76 (br. s., 1 H), 8.92 (d, J=1.6 Hz, 1 H), 8.54-8.64 (m, 2 H), 8.17 (br. s., 1 H), 7.51 (br. s., 1 H).

Intermediate 10: 3-carbamoyl-1H-pyrrolo[2,3-b]pyridine-5-carboxylic acid, shown below, was prepared as follows:

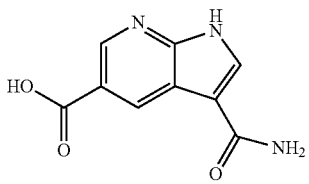 [SMILES: NC(=O)c1c[nH]c2ncc(C(=O)O)cc12]

Step 1. methyl 3-iodo-1H-pyrrolo[2,3-b]pyridine-5-carboxylate

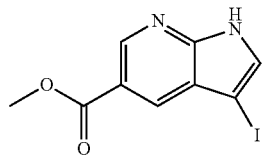

To a solution of methyl 1H-pyrrolo[2,3-b]pyridine-5-carboxylate (2.97 g, 14.0 mmol) in N,N-dimethylformamide (30 mL) was added potassium carbonate (5.79 g, 41.9 mmol). Iodine (3.90 g, 15.4 mmol) in N,N-dimethylformamide (5.0 mL) was then added dropwise and the reaction was allowed to stir at room temperature for 2 hours. Water (150 mL) was then added to the reaction mixture, resulting in the formation of a precipitate. A solution of sodium bisulfite (5.79 g, 41.9 mmol) in water (50 mL) was slowly added, and the mixture was allowed to stir for 1 hour. The resulting solid was filtered and dried under vacuum to give the title compound (3.07 g, 73%). +ESI (M+H) 303.0; $^1$H NMR (400 MHz, DMSO-$d_6$, δ): 12.53 (br. s., 1 H), 8.79 (d, J=2.0 Hz, 1 H), 8.15 (d, J=2.0 Hz, 1 H), 7.86 (s, 1 H), 3.88 (s, 3 H).

Step 2. 1-tert-butyl 5-methyl 3-iodo-1H-pyrrolo[2,3-b]pyridine-1,5-dicarboxylate

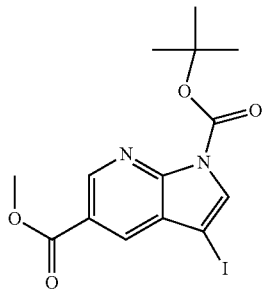 [SMILES: COC(=O)c1cnc2c(c1)c(I)cn2C(=O)OC(C)(C)C]

To a mixture of methyl 3-iodo-1H-pyrrolo[2,3-b]pyridine-5-carboxylate (700 mg, 2.32 mmol) in dichloromethane (10 mL) and tetrahydrofuran (10 mL) was added N,N-diisopropylethylamine (1.21 mL, 6.95 mmol), di-tert-butyldicarbonate (607 mg, 2.78 mmol), and 4-dimethylaminopyridine (28 mg, 23 mmol). The reaction was allowed to stir at room temperature for 16 hours. The reaction was concentrated and purification by flash column chromatography (0-50% ethyl acetate/heptanes) gave the title compound (760 mg, 82%) as a solid. +APCI (M+H) 403.3; $^1$H NMR (400 MHz, DMSO-$d_6$, δ): 8.93 (d, J=2.0 Hz, 1 H), 8.16 (d, J=2.0 Hz, 1 H), 8.14 (s, 1 H), 3.91 (s, 3 H), 1.59 (s, 9 H).

Step 3. 3-carbamoyl-1H-pyrrolo[2,3-b]pyridine-5-carboxylic acid

The title compound was prepared by a method analogous to that described in Steps 3-4 for Intermediate 6, using 1-tert-butyl 5-methyl 3-iodo-1H-pyrrolo[2,3-b]pyridine-1,5-dicarboxylate. −APCI (M−H) 204.4.

Intermediate 11: 2-carbamoyl-1H-indole-5-carboxylic acid, shown below, was prepared as follows:

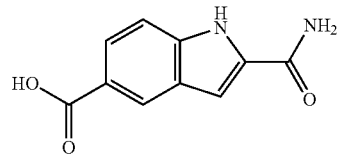 [SMILES: NC(=O)c1cc2cc(C(=O)O)ccc2[nH]1]

Step 1. methyl 2-carbamoyl-1H-indole-5-carboxylate

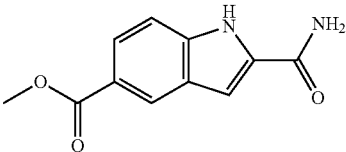 [SMILES: COC(=O)c1ccc2[nH]c(C(N)=O)cc2c1]

To a solution of 5-(methoxycarbonyl)-1H-indole-2-carboxylic acid (2.50 g, 11.4 mmol) in tetrahydrofuran (20 mL) was added 1,1-carbonyldiimidazole (3.70 g, 22.8 mmol). The yellow suspension was stirred for 2 hours. Then concentrated ammonium hydroxide (20 mL) was added and the mixture was stirred at room temperature for 5 hours. The pale green suspension was filtered, washed with water and 5 mL of methanol, and air dried to give methyl 2-carbamoyl-1H-indole-5-carboxylate (2.04 g, 82%) as a colorless solid. $^1$H NMR (400 MHz, DMSO-$d_6$, δ): 11.93 (br. s., 1 H), 8.32 (d, J=1.2 Hz, 1 H), 8.06 (br. s., 1 H), 7.79 (dd, J=8.6, 1.6 Hz, 1 H), 7.48 (d, J=8.6 Hz, 1 H), 7.45 (br. s., 1 H), 7.27 (s, 1 H), 3.32 (s, 3 H).

Step 2. 2-carbamoyl-1H-indole-5-carboxylic acid

To a suspension of methyl 2-carbamoyl-1H-indole-5-carboxylate (300 mg, 1.38 mmol) in tetrahydrofuran (4.5 mL) and ethylene glycol (4.5 mL) was added potassium hydroxide (3.16 g, 56.4 mmol). The mixture was heated to reflux and stirred for 2 hours. The reaction was cooled to room temperature and diluted with water. The tetrahydrofuran was removed under reduced pressure. The solids were filtered off and the filtrate was acidified to pH 4 with concentrated hydrochloric acid. The resulting precipitate was collected by filtration and dried under vacuum to give 2-carbamoyl-1H-indole-5-carboxylic acid (230 mg, 82%). $^1$H NMR (400 MHz, DMSO-$d_6$, δ): 12.53 (br. s., 1 H), 11.88 (br. s., 1 H), 8.28 (s, 1 H), 8.04 (br. s., 1 H), 7.77 (d, J=8.6 Hz, 1 H), 7.46 (m, J=8.6 Hz, 2 H), 7.25 (s, 1 H).

Intermediate 12: 3-carbamoyl-1H-indole-5-carboxylic acid, shown below, was prepared as follows:

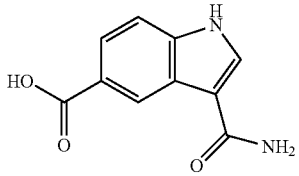 [SMILES: NC(=O)c1c[nH]c2ccc(C(=O)O)cc12]

Step 1. ethyl 3-cyano-1H-indole-5-carboxylate

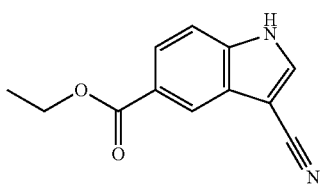 [SMILES: CCOC(=O)c1ccc2[nH]cc(C#N)c2c1]

To a solution of 5-bromo-1H-indole-3-carbonitrile (2.61 g, 11.8 mmol) in ethanol (50 mL) in a 500 mL Parr bottle was added sodium acetate (2.90 g, 35.6 mmol) and 1,1'-bis(diphenylphosphino)ferrocene-palladium (II) dichloride dichloromethane complex (1.93 g, 2.36 mmol). The reaction mixture was evacuated and back filled with nitrogen three times. The reaction vessel was then pressurized with 25 psi carbon monoxide. The reaction was heated to 70° C. and when the desired temperature was reached the pressure of the vessel was increased to 40 psi. The reaction was agitated at 70° C. for 24 hours. The mixture was filtered through Celite, rinsing with ethanol. The filtrate was concentrated under reduced pressure and then diluted with dichloromethane. The mixture was filtered to remove the insoluble solids. The filtrate was concentrated and purified by flash column chromatography (20-80% ethyl acetate/heptanes). The resulting solid was triturated with dichloromethane and a small amount of heptanes to give ethyl 3-cyano-1H-indole-5-carboxylate (1.05 g, 41%) $^1$H NMR (400 MHz, DMSO-d$_6$, δ): 12.54 (br. s., 1 H), 8.41 (d, J=2.7 Hz, 1 H), 8.25 (d, J=1.6 Hz, 1 H), 7.89 (dd, J=8.6, 1.6 Hz, 1 H), 7.66 (dd, J=8.6, 0.6 Hz, 1 H), 4.34 (q, J=7.0 Hz, 2 H), 1.35 (t, J=7.1 Hz, 3 H).

Step 2. 3-carbamoyl-1H-indole-5-carboxylic acid

A solution of ethyl 3-cyano-1H-indole-5-carboxylate (1.05 g, 4.89 mmol) in methanol (12 mL) was added to a 0° C. solution of urea hydrogen peroxide (4.74 g, 48.9 mmol) and sodium hydroxide (11.7 mL of a 2.5 M solution in water, 29.3 mmol). The mixture was allowed to warm to room temperature and stir overnight. An additional 2 mL of a 2.5 M solution of sodium hydroxide was added and the reaction was left stirring 4 hours. The mixture was concentrated and acidified to pH 2 using 6 M hydrochloric acid. The resulting precipitate was filtered off and dried under vacuum at 60° C. to give the title compound (915 mg, 92%). $^1$H NMR (400 MHz, DMSO-d$_6$, δ): 12.46 (br. s., 1 H), 11.84 (s, 1 H), 8.85 (s, 1 H), 8.12 (d, J=2.5 Hz, 1 H), 7.75 (dd, J=8.6, 1.6 Hz, 1 H), 7.50-7.63 (m, 1 H), 7.47 (d, J=8.6 Hz, 1 H), 6.88 (br. s., 1 H).

Intermediate 13: 2-carbamoyl-1H-indole-6-carboxylic acid, shown below, was prepared as follows:

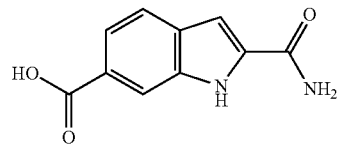 [SMILES: NC(=O)c1cc2ccc(C(=O)O)cc2[nH]1]

Step 1. ethyl 2-carbamoyl-1H-indole-6-carboxylate

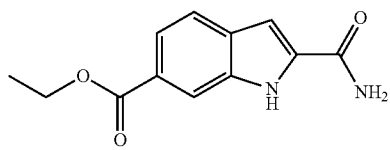 [SMILES: CCOC(=O)c1ccc2cc(C(N)=O)[nH]c2c1]

The title compound was prepared by a method analogous to that described in Step 1 for Intermediate 12, using 6-bromo-1H-indole-2-carboxamide. +ESI (M+H) 233.2; $^1$H NMR (DMSO-d$_6$, δ): 11.92 (s, 1 H), 8.07 (s, 2 H), 7.65-7.71 (m, 1 H), 7.57-7.63 (m, 1 H), 7.49 (br. s., 1 H), 7.17 (dd, J=2.1, 1.0 Hz, 1 H), 4.30 (q, J=7.1 Hz, 2 H), 1.31 (t, J=7.1 Hz, 3 H).

Step 2. 2-carbamoyl-1H-indole-6-carboxylic acid

To a solution of ethyl 2-carbamoyl-1H-indole-6-carboxylate (3.3 g, 14 mmol) in methanol (50 mL) was added 1 N aqueous sodium hydroxide (71 mL, 71 mmol). The reaction was stirred at room temperature for 17 hours. Then the reaction was acidified to pH 2-3 using 6 N aqueous hydrochloric acid. The resulting precipitate was collected by filtration and dried under vacuum to afford the title compound (2.97 g, 100%). −APCI (M−H) 203.4.

Intermediate 14: 2-amino-1H-benzo[d]imidazole-5-carboxylic acid, shown below, was prepared as follows:

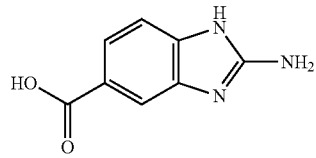 [SMILES: Nc1nc2cc(C(=O)O)ccc2[nH]1]

A solution of cyanogen bromide (5.0 mL, 5 M in acetonitrile, 25 mmol) was added to a mixture of methyl 3,4-diaminobenzoate (3.0 g, 18 mmol) in water (50 mL). The reaction was stirred at room temperature overnight. Aqueous ammonia (20 mL) and ethyl acetate (100 mL) were added to the reaction mixture and the layers were separated. The organics were dried over sodium sulfate, filtered, and concentrated. To the crude residue was added 2 N aqueous hydrochloric acid (18 mL, 36.0 mmol) and the mixture was heated at reflux overnight. The reaction was concentrated to give the title compound (2.90 g, 97%). $^1$H NMR (400 MHz, DMSO-d$_6$, δ): 8.75 (s, 2 H), 7.84 (s, 1 H), 7.77 (dd, J=1.2 Hz, J=8.4 Hz, 1 H), 7.38 (d, J=8.4 Hz, 1 H).

Intermediate 15: 3-(methylcarbamoyl)-1H-indazole-5-carboxylic acid, shown below, was prepared as follows:

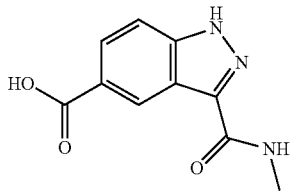 [SMILES: CNC(=O)c1n[nH]c2ccc(C(=O)O)cc12]

Step 1.
5-bromo-N-methyl-1H-indazole-3-carboxamide

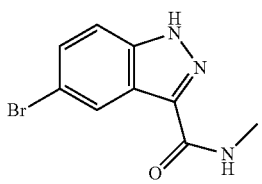

To a solution of 5-bromo-1H-indazole-3-carboxylic acid (1.2 g, 5.0 mmol) in N,N-dimethylformamide (20 mL) was added methyl amine (5 mL, 2 M in tetrahydrofuran, 10 mmol), 1, (3-dimethylaminopropyl)-3-ethyl carbodiimide hydrochloride (1.4 g, 7.5 mmol), 1-hydroxybenzotriazole hydrate (1.2 g, 7.5 mmol), and N-methylmorpholine (1.0 g, 10 mmol). The reaction was stirred at room temperature overnight. The reaction was concentrated and purification by flash column chromatography gave the title compound (0.71 g, 56%) as a colorless solid. $^1$H NMR (400 MHz, DMSO-$d_6$, δ): 13.8 (br. s., 1 H), 8.41 (m, 1 H), 8.31 (s, 1 H), 7.60 (d, J=8.8 Hz, 1 H), 7.51-7.54 (m, 1 H), 2.80 (d, J=4.8 Hz, 3 H).

Step 2. methyl 3-(methylcarbamoyl)-1H-indazole-5-carboxylate

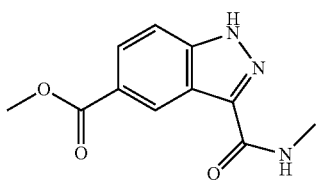

To a solution of 5-bromo-N-methyl-1H-indazole-3-carboxamide (710 mg, 2.8 mmol) in anhydrous methanol (20 mL) was added 1,1'-bis(diphenylphosphino)ferrocene-palladium (II) dichloride dichloromethane complex (400 mg, 0.56 mmol) and N-methylmorpholine (565 mg, 5.60 mmol). The reaction vessel was evacuated and back filled with nitrogen three times. The vessel was then filled with 30 psi carbon monoxide. The reaction mixture was heated to 70° C., increasing the pressure within the vessel to 45 psi. The reaction was agitated at 70° C. for 24 hours. The reaction mixture was cooled to room temperature and was filtered through Celite, rinsing with methanol. The filtrate was concentrated and purification by flash column chromatography gave the title compound (410 mg, 61%) as a brown solid. $^1$H NMR (400 MHz, DMSO-$d_6$, δ): 13.9 (s, 1 H), 8.88 (s, 1 H), 8.49 (d, J=4.8, 1 H), 7.95-7.98 (m, 1 H), 7.68-7.70 (m, 1 H), 3.88 (s, 3 H), 2.82 (d, J=4.8 Hz, 3 H).

Step 3.
3-(methylcarbamoyl)-1H-indazole-5-carboxylic acid

To a solution of methyl 3-(methylcarbamoyl)-1H-indazole-5-carboxylate (400 mg, 1.7 mmol) in methanol (10 mL) and water (10 mL), was added lithium hydroxide monohydrate (0.36 g, 8.5 mmol). The reaction was heated to 60° C. and was stirred overnight. The methanol was removed under reduced pressure and the remaining residue was acidified to pH=4 with 1 N aqueous hydrochloric acid. The resulting precipitate was collected by filtration and dried under vacuum to give the title compound (350 mg, 94%) as a yellow solid. $^1$H NMR (400 MHz, DMSO-$d_6$, δ): 13.99 (s, 1 H), 8.85 (s, 1 H), 8.47-8.48 (m, 1 H), 7.94-7.96 (m, 1 H), 7.65-7.68 (m, 1 H), 2.82 (d, J=4.4 Hz, 3 H).

Intermediate 16: 3-(ethylcarbamoyl)-1H-indazole-5-carboxylic acid, shown below, was prepared as follows:

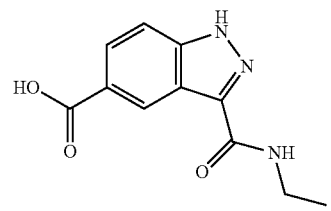 [SMILES: CCNC(=O)c1n[nH]c2ccc(C(=O)O)cc12]

Step 1.
5-bromo-N-ethyl-1H-indazole-3-carboxamide

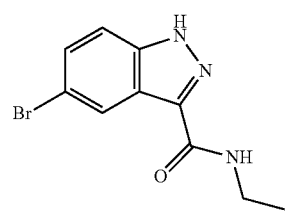

To a solution of 5-bromo-1H-indazole-3-carboxylic acid (1.2 g, 5.0 mmol) in dichloromethane (20 mL) was added oxalyl chloride (1.26 g, 10 mmol) and 1 drop of N,N-dimethylformamide. The mixture was stirred at room temperature under a nitrogen atmosphere overnight. The reaction was concentrated and the residue was dissolved in dichloromethane (20 mL). Ethylamine (1.1 g, 25 mmol) was added dropwise. The reaction was allowed to stir at room temperature for 4 hours. The reaction mixture was concentrated to provide the title compound (1.27 g). +ESI (M+H+1) 270.9.

Step 2. ethyl 3-(ethylcarbamoyl)-1H-indazole-5-carboxylate

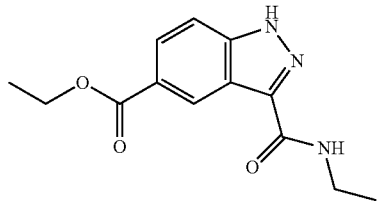 [SMILES: CCNC(=O)c1n[nH]c2ccc(C(=O)OCC)cc12]

To a solution of 5-bromo-N-ethyl-1H-indazole-3-carboxamide (1.1 g, 4.1 mmol) in ethanol (50 mL), was added triethylamine (1.24 g, 12.3 mmol) and 1,1'-bis(diphenylphosphino)ferrocene-palladium (II) dichloride dichloromethane complex (300 mg, 0.41 mmol). The reaction vessel was evacuated and back filled with nitrogen three times. The vessel was filled with 50 psi carbon monoxide, heated to 80° C., and was agitated for 24 hours. The reaction was cooled to room temperature and filtered on Celite. The filtrate was concentrated to a brown residue. The residue was diluted with ethyl acetate (100 mL) and was washed successively with 1 N hydrochloric acid, saturated aqueous sodium bicarbonate, and brine. The organics were dried over sodium sulfate, filtered, and concentrated to give the title compound (0.88 g, 82%) as a brown solid. $^1$H NMR (400 MHz, DMSO-$d_6$, δ): 13.87 (s, 1 H), 8.88 (s, 1 H), 8.54-8.57 (m, 1 H), 7.96-7.98 (m, 1 H), 7.68-7.70 (m, 1 H), 4.32-4.37 (m, 2 H), 3.33-3.37 (m, 2 H), 1.35 (t, 3 H), 1.22 (t, 3 H).

Step 3. 3-(ethylcarbamoyl)-1H-indazole-5-carboxylic acid

The title compound was prepared by a method analagous to that described in Step 3 of Intermediate 15. $^1$H NMR (400 MHz, DMSO-$d_6$, δ): 13.83 (s, 1 H), 12.91 (br. s., 1 H), 8.86 (s, 1 H), 8.51-8.54 (m, 1 H), 7.95-7.97 (m, 1 H), 7.65-7.68 (m, 1 H), 3.30-3.36 (m, 2 H), 1.12-1.16 (t, 3 H).

Intermediate 17: 3-(2,2,2-trifluoroethylcarbamoyl)-1H-indazole-5-carboxylic acid, shown below, was prepared as follows:

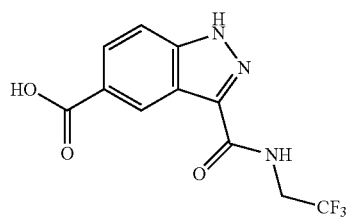 [SMILES: O=C(O)c1ccc2[nH]nc(C(=O)NCC(F)(F)F)c2c1]

The title compound was prepared by a method analogous to that described for Intermediate 16, using 2,2,2-trifluoroethylamine in Step 1. $^1$H NMR (400 MHz, DMSO-$d_6$, δ): 14.04 (s, 1 H), 13.0 (br. s., 1 H), 9.12-9.15 (m, 1 H), 8.83 (s, 1 H), 7.97-7.99 (m, 1 H), 7.69-7.72 (m, 1 H), 4.04-4.13 (m, 2 H).

Intermediate 18: 2-(methylamino)-1H-benzo[d]imidazole-5-carboxylic acid, shown below, was prepared as follows:

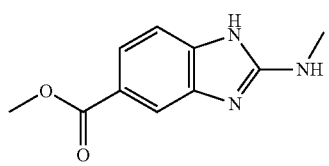

Step 1. methyl 2-(methylamino)-1H-benzo[d]imidazole-5-carboxylate

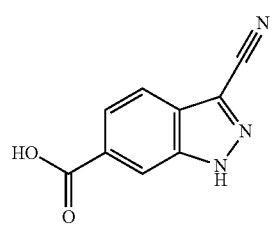 [SMILES: N#Cc1n[nH]c2cc(C(=O)O)ccc12]

A mixture of 3,4-diaminobenzoic acid (15 g, 0.09 mol) and isothiocyanatomethane (6.6 g, 0.09 mol) was dissolved in tetrahydrofuran (90 mL). The reaction was heated at reflux for 3 hours and was then concentrated. The residue was poured into ice water. The resulting precipitate was filtered, washed with water, and dried under vacuum to give methyl 4-amino-3-(3-methylthioureido)benzoate (12.0 g, 56%).

To the solid (12 g, 0.05 mol) was added ethanol (200 mL), followed by methyl iodide (35.5 g, 0.25 mol). The reaction was heated to reflux and stirred overnight. The reaction was concentrated and the residue was basified with ammonium hydroxide. The solids were collected by filtration and washed with water. Purification by column chromatography (9-25% ethyl acetate/petroleum ether) gave the title compound (2.9 g, 28%) as a yellow solid. $^1$H NMR (400 MHz, CDCl$_3$, δ): 8.37 (s, 1 H), 7.92-7.96 (m, 1 H), 7.51 (d, J=8.4 Hz, 1 H), 3.93 (s, 3 H), 2.81 (s, 3 H).

Step 2. 2-(methylamino)-1H-benzo[d]imidazole-5-carboxylic acid

3 N Aqueous hydrochloric acid (14 mL, 42 mmol) was added to methyl 2-(methylamino)-1H-benzo[d]imidazole-5-carboxylate (2.9 g, 14 mmol) and the reaction was stirred at reflux overnight. The reaction was concentrated to give the title compound (2.4 g, 90%) as a yellow solid. $^1$H NMR (400 MHz, CD$_3$OD, δ): 7.96-8.00 (m, 2 H), 7.40 (d, J=8.4 Hz, 1 H), 3.10 (s, 3 H).

Intermediate 19: 3-cyano-1H-indazole-6-carboxylic acid, shown below, was prepared as follows:

Step 1: methyl 1H-indazole-6-carboxylate

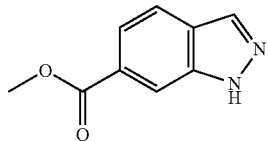

To a solution of 1H-indazole-6-carboxylic acid (3.00 g, 18.5 mmol) in N,N-dimethylformamide (46 mL) was added sodium carbonate (2.06 g, 19.4 mmol), followed by iodomethane (2.75 g, 1.21 mL, 19.4 mmol) dropwise. The mixture was stirred at room temperature overnight. The mixture was poured into half saturated sodium bicarbonate and extracted with ethyl acetate three times. The combined organic layers were washed with brine, dried over sodium sulfate, filtered and concentrated in vacuo to afford a brown oil. This residue was purified by flash column chromatography (12-100% ethyl acetate/heptanes) to afford methyl 1H-indazole-6-carboxylate as a yellow solid (2.95 g, 90%). $^1$H NMR (400 MHz, CDCl$_3$, δ): 10.40 (br. s., 1 H), 8.26 (s, 1 H), 8.13 (s, 1 H), 7.84 (d, J=8.4 Hz, 1 H), 7.79 (d, J=8.4 Hz, 1 H), 3.96 (s, 3 H).

Step 2: methyl 3-iodo-1H-indazole-6-carboxylate

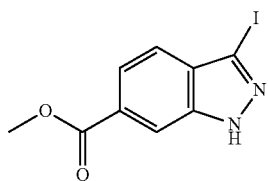

To a solution of methyl 1H-indazole-6-carboxylate (865 mg, 4.91 mmol) in N,N-dimethylformamide (12 mL) was added potassium hydroxide (840 mg, 3.05 mmol) followed by iodine (1.54 g, 5.9 mmol). The mixture was stirred at room temperature for 3 hours. Sodium bisulfate (30 mL of 5% aqueous) was added and the mixture was extracted with ethyl acetate twice. The combined organic layers were washed with brine, dried over sodium sulfate, filtered and concentrated in vacuo. The residue was purified via flash column chromatography (5-65% ethyl acetate/heptanes) to afford methyl 3-iodo-1H-indazole-6-carboxylate as a colorless solid (1.16 g, 78%). $^1$H NMR (400 MHz, DMSO-d$_6$, δ): 13.84 (s, 1 H), 8.13 (s, 1 H), 7.72 (d, J=8.4 Hz, 1 H), 7.54 (d, J=8.6 Hz, 1 H), 3.87 (s, 3 H).

Step 3: methyl 3-cyano-1H-indazole-6-carboxylate

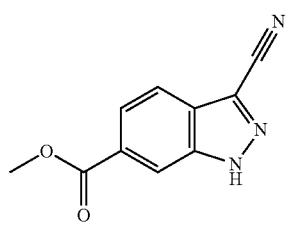

A mixture of methyl 3-iodo-1H-indazole-6-carboxylate (3.0 g, 9.9 mmol), zinc dust (400 mg, 6.11 mmol), zinc cyanide (2.0 g, 17.0 mmol), [1,1'-bis(diphenylphosphino)ferrocene]-dichloropalladium(II), complex with dichloromethane (1.15 g, 1.41 mmol), and copper (I) iodide (1.90 g, 9.97 mmol) in dimethylacetamide (55 mL) was purged with nitrogen for 15 minutes. The mixture was stirred at 120° C. for 15 hours. The reaction mixture was cooled, diluted with ethyl acetate (250 mL), and filtered through Celite, rinsing with ethyl acetate (100 mL). To the filtrate was added ~400 mL of a solution of saturated aqueous ammonium chloride and concentrated ammonium hydroxide (prepared by adding ammonium hydroxide to a saturated aqueous solution of ammonium chloride until pH=8). The mixture was stirred for 1 hour. The layers were then separated. The organic layer was washed with water and brine, dried over sodium sulfate, filtered and concentrated in vacuo. To the residue was added methanol (40 mL) and the mixture was stirred overnight. The mixture was filtered and the solid was dried in vacuo to give methyl 3-cyano-1H-indazole-6-carboxylate as a tan solid (1.47 g, 73%). $^1$H NMR (400 MHz, DMSO-d$_6$, δ): 13.40 (br. s., 1 H), 8.25 (s, 1 H), 7.94 (d, J=8.6 Hz, 1 H), 7.83 (d, J=8.4 Hz, 1 H), 3.88 (s, 3 H).

Step 4: 3-cyano-1H-indazole-6-carboxylic acid

To a solution of methyl 3-cyano-1H-indazole-6-carboxylate (1.47 g, 7.31 mmol) in methanol (36 mL) and tetrahydrofuran (20 mL) was added 2 N aqueous lithium hydroxide (16 mL, 32 mmol). The reaction was heated to 50° C. for 72 hours. The reaction was cooled to room temperature and concentrated. The residue was diluted with water and the pH was adjusted to 4 with 1 N aqueous hydrochloric acid. The resulting precipitate was filtered off, rinsed with water, and dried under vacuum to provide the title compound (500 mg, 37%) as a tan solid. +ESI (M+H) 188.2.

Intermediate 20: 3-chloro-1H-pyrrolo[3,2-b]pyridine-6-carboxylic acid, shown below, was prepared as follows:

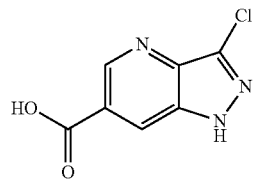 [SMILES: O=C(O)c1cnc2c(Cl)n[nH]c2c1]

Step 1: methyl 3-chloro-1H-pyrrolo[3,2-b]pyridine-6-carboxylate

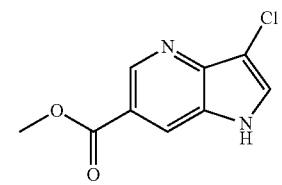

To a 0° C. solution of methyl 1H-pyrrolo[3,2-b]pyridine-6-carboxylate (1.00 g, 5.68 mmol) in N,N-dimethylformamide (15 mL) was added N-chlorosuccinimide (895 mg, 5.96 mmol). The reaction was allowed to gradually warm to room temperature and stir overnight. The reaction was diluted with water (125 mL) and stirred for 20 minutes. The resulting solid was collected by filtration, washed with water, and dried under vacuum to give the title compound (1.11 g, 93%) as an orange powder. +ESI (M+H) 211.0; $^1$H NMR (400 MHz, DMSO-$d_6$, δ): 11.99 (br. s., 1 H), 8.92 (d, J=2.0 Hz, 1 H), 8.31 (d, J=1.8 Hz, 1 H), 8.08 (d, J=3.1 Hz, 1 H), 3.88 (s, 3 H).

Step 2:
3-chloro-1H-pyrrolo[3,2-b]pyridine-6-carboxylic acid

Methyl 3-chloro-1H-pyrrolo[3,2-b]pyridine-6-carboxylate (1.10 g, 5.22 mmol) was suspended in 1,4-dioxane (25 mL) and 6 N aqueous hydrochloric acid (8.7 mL) was added. The reaction was allowed to stir at room temperature overnight. The reaction was then concentrated to give the title compound (1.2 g, 100%). +ESI (M+H) 197.1; $^1$H NMR (400 MHz, DMSO-$d_6$, δ): 12.50 (br. s., 1 H), 8.92 (d, J=1.6 Hz, 1 H), 8.46 (br. s., 1 H), 8.19 (br. s., 1 H).

Intermediate 21: 3-cyano-1H-indazole-5-carboxylic acid, shown below, was prepared as follows:

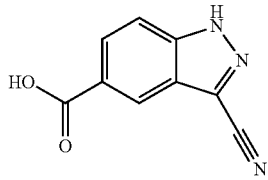 [SMILES: N#Cc1n[nH]c2ccc(C(=O)O)cc12]

Methyl 3-cyano-1H-indazole-5-carboxylate (500 mg, 2.5 mmol) was dissolved in methanol (12 mL) and 2 N aqueous lithium hydroxide (3.7 mL, 7 mmol) was added. The reaction was stirred at room temperature overnight. The reaction mixture was concentrated to remove the methanol and the residue was acidified to pH=4 with 1 N aqueous hydrochloric acid. The resulting yellow precipitate was collected by filtration, washed with water, and dried in a vacuum oven to provide the title compound (445 mg, 96%). −ESI (M−H) 186.4; $^1$H NMR (400 MHz, DMSO-$d_6$, δ): 13.17 (br. s., 1 H), 8.42 (s, 1 H), 8.05 (dd, J=8.8, 1.6 Hz, 1 H), 7.83 (d, 1 H).

Intermediate 22: 6-(2-tert-butoxy-2-oxoethoxy)quinoline-3-carboxylic acid, shown below, was prepared as follows:

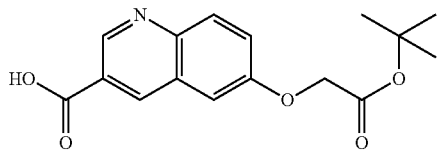 [SMILES: CC(C)(C)OC(=O)COc1ccc2ncc(C(=O)O)cc2c1]

Step 1: 2-chloro-6-hydroxyquinoline-3-carbaldehyde

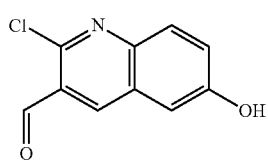 [SMILES: O=Cc1cc2cc(O)ccc2nc1Cl]

To a −78° C. mixture of 2-chloro-6-methoxyquinoline-3-carbaldehyde (4.64 g, 20.9 mmol) in dichloromethane (130 mL) was added boron tribromide (4.0 mL, 42 mmol). The mixture was allowed to warm to room temperature and stir for 4 hours. The reaction was neutralized by the careful addition of saturated aqueous sodium bicarbonate. The mixture was then extracted with 2-methyl tetrahydrofuran (3×). The combined organics were filtered, and the filtrate was washed with saturated aqueous sodium bicarbonate (3×) and once with brine. The organics were dried over sodium sulfate, filtered, and concentrated to a yellow solid. The solid was partially dissolved in 2-methyl tetrahydrofuran and filtered. The filtrate was concentrated to a solid and again partially dissolved in 2-methyl tetrahydrofuran, filtered, and concentrated. Purification by flash column chromatography (10-100% ethyl acetate/heptanes) gave the title compound (2.65 g, 61%) as a pale yellow solid. +ESI (M+H) 208.1; $^1$H NMR (400 MHz, CDCl$_3$, δ): 10.54 (s, 1 H), 8.59 (s, 1 H), 7.98 (d, J=9.17 Hz, 1 H), 7.47 (dd, J=9.17, 2.73 Hz, 1 H), 7.25 (d, J=2.93 Hz, 1 H), 5.57 (br. s., 1 H).

Step 2: tert-butyl 2-(2-chloro-3-formylquinolin-6-yloxy)acetate

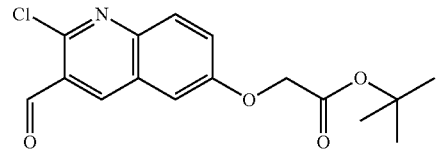 [SMILES: CC(C)(C)OC(=O)COc1ccc2nc(Cl)c(C=O)cc2c1]

To a solution of 2-chloro-6-hydroxyquinoline-3-carbaldehyde (2.35 g, 11.3 mmol) in N,N-dimethylformamide (15 mL) was added tert-butyl 2-bromoacetate (2.0 mL, 13.6 mmol) and potassium carbonate (3.13 g, 22.6 mmol). The reaction was stirred at room temperature for 1.5 hours. The reaction was diluted with water (100 mL) and allowed to stir for 1 hour. The resulting solid was collected by filtration, washed with water, and dried under vacuum to give the title compound (3.62 g, 99%) as an off-white solid. +ESI (M+H) 322.1; $^1$H NMR (400 MHz, CDCl$_3$, δ): 10.54 (s, 1 H), 8.60 (s, 1 H), 7.99 (d, J=9.36 Hz, 1 H), 7.59 (dd, J=9.17, 2.93 Hz, 1 H), 7.11 (d, J=2.73 Hz, 1 H), 4.65 (s, 2 H), 1.49 (s, 9 H).

Step 3: 6-(2-tert-butoxy-2-oxoethoxy)-2-chloroquinoline-3-carboxylic acid

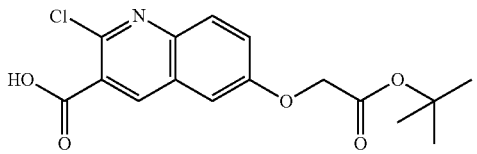 [SMILES: CC(C)(C)OC(=O)COc1ccc2nc(Cl)c(C(=O)O)cc2c1]

To a suspension of tert-butyl 2-(2-chloro-3-formylquinolin-6-yloxy)acetate (3.6 g, 11 mmol) in tert-butanol (150 mL) was added 2-methyl-2-butene (14.9 mL, 133 mmol) and a solution of sodium chlorite (8.27 g, 73.1 mmol) and sodium dihydrogenphosphate (8.10 g, 58.7 mmol) in water (50 mL). The reaction was allowed to stir at room temperature for 1 hour. The tert-butanol was removed in vacuo. The mixture was diluted with water (60 mL) and acidified to pH=4 with 1 N aqueous hydrochloric acid. The resulting precipitate was filtered, washed with water, and dried under vacuum to give the title compound (3.7 g, 100%) as a white solid. +ESI (M+H) 338.1; ¹H NMR (400 MHz, CD₃OD, δ): 8.69 (s, 1 H), 7.89 (d, J=9.19 Hz, 1 H), 7.56 (dd, J=9.19, 2.74 Hz, 1 H), 7.34 (d, J=2.93 Hz, 1 H), 4.76 (s, 2 H), 1.49 (s, 9 H).

Step 4: 6-(2-tert-butoxy-2-oxoethoxy)quinoline-3-carboxylic acid

Methanol (100 mL) and triethylamine (4.5 mL, 33 mmol) were added to 6-(2-tert-butoxy-2-oxoethoxy)-2-chloroquinoline-3-carboxylic acid (1.27 g, 3.76 mmol). 10% Palladium on carbon (350 mg) was added and the reaction was pressurized to 17 psi hydrogen. The reaction was agitated at room temperature for 3 hours. The reaction mixture was diluted with methanol and filtered through Celite. The filtrate was concentrated to a yellow solid. The solid was diluted with water and the mixture was acidified to pH=4 with 1 N aqueous hydrochloric acid. The solid was collected by filtration, washed with water, and dried under vacuum to give the title compound (960 mg, 84%) as a pale yellow solid. +ESI (M+H) 304.2; ¹H NMR (400 MHz, CD₃OD, δ): 9.19 (d, J=2.15 Hz, 1 H), 8.87 (d, J=2.15 Hz, 1 H), 8.01 (d, J=9.36 Hz, 1 H), 7.59 (dd, J=9.27, 2.83 Hz, 1 H), 7.38 (d, J=2.73 Hz, 1 H), 4.78 (s, 2 H), 1.49 (s, 9 H).

Intermediate 23: 6-carbamoylquinoline-3-carboxylic acid, shown below, was prepared as follows:

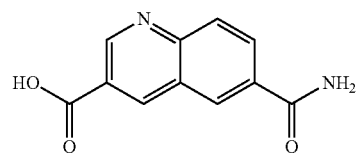 [SMILES: NC(=O)c1ccc2ncc(C(=O)O)cc2c1]

Step 1: ethyl 6-bromoquinoline-3-carboxylate

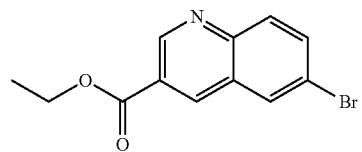 [SMILES: CCOC(=O)c1cnc2ccc(Br)cc2c1]

To a solution of 5-bromo-2-nitrobenzaldehyde (2 g, 9 mmol) in ethanol (46 mL) was added tin(II) chloride dihydrate (7.95 g, 35.2 mmol) and 3,3-diethoxypropionic acid ethyl ester (4.2 mL, 22 mmol). The reaction was heated to 90° C. for 16 hours. The reaction was then allowed to cool to room temperature and stir overnight. The reaction mixture was concentrated and the residue was dissolved in ethyl acetate. The mixture was poured into saturated aqueous sodium bicarbonate. The resulting emulsion was filtered through Celite, rinsing with ethyl acetate. The layers were separated and the aqueous was extracted with ethyl acetate. The combined organics were washed with brine, dried over magnesium sulfate, filtered, and concentrated. Purification by flash column chromatography (0-50% ethyl acetate/heptanes) gave the title compound (1.41 g, 60%) as a solid.

Step 2: 6-carbamoylquinoline-3-carboxylic acid

The title compound was prepared by a method analogous to that described in Steps 3-4 of Intermediate 6, using ethyl 6-bromoquinoline-3-carboxylate. +ESI (M+H) 217.0; ¹H NMR (400 MHz, DMSO-d₆, δ): 13.58 (br. s., 1 H), 9.34 (d, J=2.1 Hz, 1 H), 8.97 (d, J=2.1 Hz, 1 H), 8.67 (d, J=2.0 Hz, 1 H), 8.25-8.31 (m, 1 H), 8.20 (br. s., 1 H), 8.09-8.14 (m, 1 H), 7.61 (br. s., 1 H).

Intermediate 24: 7-bromo-6-methoxyquinoline-3-carboxylic acid, shown below, was

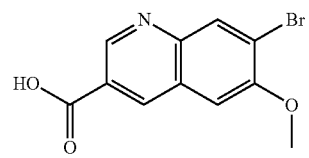

Step 1:
1-bromo-2-methoxy-4-methyl-5-nitrobenzene

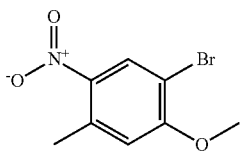

To a solution of 4-methoxy-2-methyl-1-nitrobenzene (2.0 g, 12 mmol) in N,N-dimethylformamide (5 mL) was added N-bromosuccinimide (8.52 g, 47.9 mmol). The reaction was heated to 100° C. for 1.5 hours. The reaction was cooled to room temperature and diluted with saturated aqueous sodium thiosulfate. The mixture was extracted with ethyl acetate (3×). The combined organics were washed with water, saturated sodium thiosulfate, and brine, dried over sodium sulfate, filtered, and concentrated. The residue was purified via flash column chromatography (0-30% ethyl aceate/heptanes) to provide the title compound (2.6 g, ~43% pure) as a pale yellow solid. ¹H NMR (400 MHz, CDCl₃, δ): 8.32 (s, 1 H), 6.74 (s, 1 H), 3.97 (s, 3 H), 2.63 (s, 3 H).

Step 2: 4-bromo-5-methoxy-2-nitrobenzaldehyde

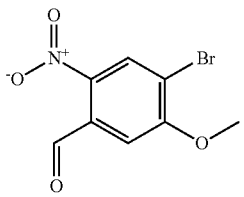

The crude 1-bromo-2-methoxy-4-methyl-5-nitrobenzene (2.6 g, 11 mmol) was dissolved in N,N-dimethylformamide (15 mL) and N,N-dimethylformamide dimethylacetal (5 mL, 38 mmol) was added. The reaction was heated to 120° C. for 18 hours. The reaction was cooled to room temperature and the mixture was added directly to a 0° C. suspension of sodium periodate (12.2 g, 57.2 mmol) in water (20 mL) and N,N-dimethylformamide (5 mL). The reaction was stirred at 0° C. for 2 hours, then allowed to warm to room temperature and stir for another 6 hours. The reaction mixture was filtered, rinsing with ethyl acetate, toluene, and water. The filtrate was extracted with ethyl acetate (3×). The combined organics were washed with water and brine, dried over sodium sulfate, filtered, and concentrated. Purification by flash column chromatography (0-50% ethyl acetate/heptanes) gave the title compound (550 mg, 19%) as a pale yellow solid. $^1$H NMR (400 MHz, CDCl$_3$, δ): 10.47 (s, 1 H), 8.41 (s, 1 H), 7.35 (s, 1 H), 4.05 (s, 3 H).

Step 3: ethyl 7-bromo-6-methoxyquinoline-3-carboxylate

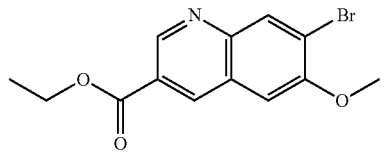 [SMILES: CCOC(=O)c1cnc2cc(Br)c(OC)cc2c1]

To a suspension of 4-bromo-5-methoxy-2-nitrobenzaldehyde (475 mg, 1.83 mmol) in ethanol (15 mL) was added tin(II) chloride dihydrate (1.65 g, 7.31 mmol) and ethyl 3,3-diethoxypropionate (1.0 mL, 5.1 mmol). The reaction was heated to 90° C. for 3 hours. LCMS showed the reaction to be incomplete. Additional tin(II) chloride dihydrate (600 mg, 2.7 mmol) and ethyl 3,3-diethoxypropionate (0.35 mL, 1.8 mmol) were added and the reaction was left heating overnight. LCMS showed the reaction to be incomplete. Tin(II) chloride dihydrate (200 mg, 0.89 mmol) and ethyl 3,3-diethoxypropionate (0.10 mL, 0.51 mmol) were added and the reaction was heated at 90° C. for another 3 hours. The reaction was concentrated and the residue partitioned between ethyl acetate and saturated aqueous sodium bicarbonate. The aqueous layer was filtered and extracted again with ethyl acetate. The combined organics were washed with brine, dried over sodium sulfate, filtered, and concentrated. The residue was purified via flash column chromatography (0-100% ethyl acetate/heptanes) to give a yellow solid (410 mg) which contained desired product and impurities. This material was taken up in tetrahydrofuran (5 mL) and ethyl 3,3-diethoxypropionate (0.17 mL, 0.87 mmol) and p-toluenesulfonic acid monohydrate (12.0 mg, 0.63 mmol) were added. The mixture was heated to 75° C. and stirred for 3 hours. The reaction was concentrated and the residue partitioned between ethyl acetate and saturated aqueous sodium bicarbonate. The layers were separated and the aqueous was extracted with ethyl acetate (2×). The combined organics were washed with brine, dried over sodium sulfate, filtered, and concentrated. Purification by flash column chromatography (0-25% ethyl acetate/heptanes) gave the title compound (256 mg, 45%) as a yellow solid. +ESI (M+H+1) 313.3.

Step 4: 7-bromo-6-methoxyquinoline-3-carboxylic acid

To a solution of ethyl 7-bromo-6-methoxyquinoline-3-carboxylate (250 mg, 0.80 mmol) in tetrahydrofuran (5 mL) was added 1 N aqueous lithium hydroxide (1.6 mL, 1.6 mmol). The reaction was stirred at room temperature overnight. The reaction was concentrated and the residue was taken up in water and 1 N aqueous lithium hydroxide (0.4 mL). The solution was extracted twice with ethyl acetate. The aqueous layer was then acidified to pH=4 with 1 N aqueous hydrochloric acid. The resulting precipitate was filtered, washed with water, and dried under vacuum to give the title compound (165 mg, 73%) as an off-white solid. +ESI (M+H+1) 284.1; $^1$H NMR (400 MHz, CD$_3$OD, δ): 9.19 (d, J=2.15 Hz, 1 H), 8.89 (d, J=1.76 Hz, 1 H), 8.30 (s, 1 H), 7.53 (s, 1 H), 4.04 (s, 3 H).

Intermediate 25: 2-(tert-butylamino)quinoline-7-carboxylic acid, shown below, was prepared as follows:

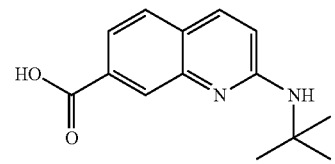 [SMILES: CC(C)(C)Nc1ccc2ccc(C(=O)O)cc2n1]

Step 1: 7-(ethoxycarbonyl)quinoline 1-oxide

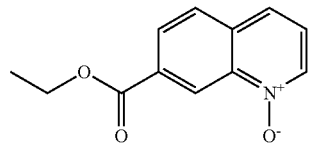 [SMILES: CCOC(=O)c1ccc2ccc[n+]([O-])c2c1]

To a solution of ethyl quinoline-7-carboxylate (1.02 g, 5.05 mmol) in dichloromethane (20 mL) was added peracetic acid (2.13 mL, 10.1 mmol, 32 wt % in acetic acid). The reaction was stirred at room temperature overnight. The reaction was partitioned between water and dichloromethane. The layers were separated and the aqueous was extracted with dichloromethane (4×). The combined organics were washed with water and brine, dried over sodium sulfate, filtered, and concentrated. The solid was concentrated from heptanes and ethyl acetate several times, then dried under vacuum to give the title compound (1.01 g, 92%) as a yellow solid. +ESI (M+H) 218.2; $^1$H NMR (400 MHz, CDCl$_3$, δ): 9.40 (s, 1 H), 8.65 (d, J=6.05 Hz, 1 H), 8.27 (dd, J=8.58, 1.56 Hz, 1 H), 7.95 (d, J=8.39 Hz, 1 H), 7.82 (d, J=8.58 Hz, 1 H), 7.42 (dd, J=8.49, 6.15 Hz, 1 H), 4.47 (q, J=7.02 Hz, 2 H), 1.45 (t, J=7.1 Hz, 3 H).

Step 2: 2-(tert-butylamino)quinoline-7-carboxylic acid

To a 0° C. solution of 7-(ethoxycarbonyl)quinoline 1-oxide (500 mg, 2.3 mmol) and tert-butylamine (1.46 mL, 13.8 mmol) in trifluoromethylbenzene (25 mL) was added p-toluenesulfonic anhydride (1.96 g, 5.76 mmol) portion-wise, maintaining the internal reaction temperature below 5° C. The reaction was stirred for 1 hour. Saturated aqueous sodium bicarbonate was added and the reaction mixture was allowed to stir for 15 minutes. The phases were then separated and the aqueous was extracted with dichloromethane (2×). The combined organics were washed with brine, dried over magnesium sulfate, filtered, and concentrated. Purification by flash column chromatography gave 499 mg of a clear oil that solidified upon standing. This material was taken up in tetrahydrofuran (5 mL) and 1 N aqueous lithium hydroxide (3.6 mL, 3.6 mmol) was added. The reaction was stirred at room temperature overnight. The reaction was concentrated and the residue was diluted with water and acidified to pH=4 with 1 N aqueous hydrochloric acid. The resulting precipitate was filtered off and dried under vacuum to give the title compound (330 mg, 75%) as a pale yellow powder. −ESI (M−H) 243.1; $^1$H NMR (400 MHz, DMSO-d$_6$, δ): 12.86 (br. s., 1 H), 8.02 (d, J=1.56 Hz, 1 H), 7.81 (d, J=9.03 Hz, 1 H), 7.57-7.65 (m, 2 H), 6.83 (d, J=8.97 Hz, 1 H), 6.81 (br. s., 1 H), 1.46 (s, 9 H).

Intermediate 26: 2-(methylamino)quinoline-7-carboxylic acid, shown below, was prepared as follows:

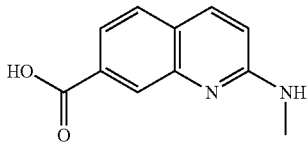

Step 1: ethyl 2-(methylamino)quinoline-7-carboxylate

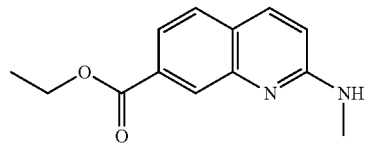 [SMILES: CCOC(=O)c1ccc2ccc(NC)nc2c1]

To a −70° C. solution of 7-(ethoxycarbonyl)quinoline 1-oxide (1.67 g, 7.70 mmol) in dichloromethane (80 mL) was added trifluoromethanesulfonic anhydride (1.43 mL, 8.47 mmol) dropwise, under a nitrogen atmosphere. The mixture was stirred at −70° C. for 5 minutes. Then a solution of methylamine in tetrahydrofuran (21 mL, 42 mmol, 2.0 M) was added dropwise at −70° C. The mixture was stirred for 5 minutes and then the reaction was quenched with water (20 mL). The layers were separated and the aqueous was extracted with dichloromethane (3×30 mL). The combined organics were washed with brine, dried over sodium sulfate, filtered, and concentrated. Purification by flash column chromatography gave the title compound (720 mg, 41%) as a yellow solid. $^1$H NMR (400 MHz, CDCl$_3$, δ): 8.42 (s, 1 H), 7.84-7.82 (m, 2 H), 7.63-7.61 (m, 1 H), 6.72-6.70 (m, 1 H), 4.92 (br. s., 1 H), 4.44-4.38 (m, 2 H), 3.12-3.11 (m, 3 H), 1.44-1.40 (m, 3 H).

Step 2: 2-(methylamino)quinoline-7-carboxylic acid

The title compound was prepared by a method analogous to that described in Step 2 of Intermediate 13, using ethyl 2-(methylamino)quinoline-7-carboxylate. $^1$H NMR (400 MHz, DMSO, δ): 8.08 (s, 1 H), 7.91-7.89 (m, 1 H), 7.71-7.62 (m, 2 H), 7.21 (s, 1 H), 6.85-6.83 (m, 1 H), 2.91-2.90 (m, 3 H).

Example 1

6-[(1-isopropyl-7-oxo-1,4,6,7-tetrahydro-1'H-spiro [indazole-5,4'-piperidin]-1'-yl) carbonyl]-1H-indole-3-carboxamide

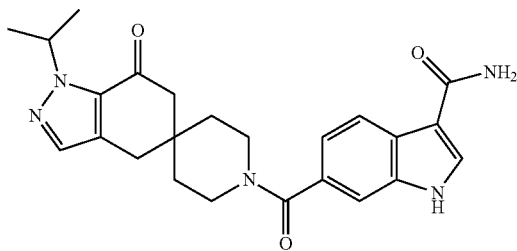 [SMILES: CC(C)n1ncc2c1C(=O)CC1(CCN(C(=O)c3ccc4c(C(N)=O)c[nH]c4c3)CC1)C2]

A mixture of 3-carbamoyl-1H-indole-6-carboxylic acid (25 mg, 0.12 mmol), 1-isopropyl-4,6-dihydrospiro[indazole-5,4'-piperidin]-7(1H)-one (38 mg, 0.13 mmol), (1H-7-azabenzotriazol-1-yl)-1,1,3,3-tetramethyl uronium hexafluorophosphate (46 mg, 0.12 mmol), and diisopropyethylamine (85 μL, 0.49 mmol) in 0.5 mL of dimethylformamide was stirred at room temperature overnight. The reaction was diluted with ethyl acetate and washed with 0.1 N hydrochloric acid. The organic layer was dried over magnesium sulfate, filtered, and concentrated in vacuo. The residue was purified by reversed-phase HPLC to yield the title compound (14.6 mg, 28%). Analytical LCMS: +ESI (M+H) 434.1; retention time 2.24 minutes (Waters Atlantis C$_{18}$ 4.6×50 mm, 5 μM column; 95% water/acetonitrile linear gradient to 5% water/acetonitrile over 4.0 minutes, hold at 5% water/acetonitrile to 5.0 minutes; 0.05% trifluoroacetic acid modifier; flow rate 2.0 mL/minute) (Method A).

Example 2

5-[(1-isopropyl-7-oxo-1,4,6,7-tetrahydro-1'H-spiro [indazole-5,4'-piperidin]-1'-yl) carbonyl]-1H-indazole-3-carboxamide

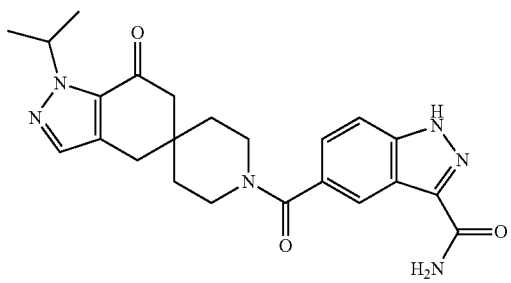 [SMILES: CC(C)n1ncc2c1C(=O)CC1(CCN(C(=O)c3ccc4[nH]nc(C(N)=O)c4c3)CC1)C2]

To a suspension of 1-isopropyl-4,6-dihydrospiro[indazole-5,4'-piperidin]-7(1H)-one (16.8 g, 53.6 mmol) and 3-carbamoyl-1H-indazole-5-carboxylic acid (10.0 g, 48.7 mmol) in N,N-dimethylformamide (120 mL) was added triethylamine (40 mL, 290 mmol). The mixture was stirred at room temperature for 5 minutes and was then cooled to 5° C. 1-Propanephosphonic acid cyclic anhydride (60 mL, 100 mmol, 50 wt % solution in ethyl acetate) was added dropwise over 20 minutes, maintaining and internal temperature between 5-10° C. The reaction was allowed to stir overnight, gradually warming to room temperature. The reaction mixture was slowly poured into 700 mL of water at 5° C. The resulting precipitate was filtered off and dried. To the filtrate was added 10% methanol/ethyl acetate (1 L) and the resulting precipitate was filtered off and dried. The solids collected were combined (8.9 g) and were dissolved in N,N-dimethylformamide (34 mL) at 130° C. The solution was cooled to 100° C. and methanol (65 mL) was added. The solution was allowed to slowly cool to room temperature. The resulting precipitate was collected by filtration and dried to give the title compound (6.0 g, 28%). +ESI (M+H) 435.1; $^1$H NMR (400 MHz, DMSO-d$_6$, δ): 13.65 (s, 1 H), 8.15 (s, 1 H), 7.75 (s, 1 H), 7.60 (d, J=8.6 Hz, 1 H), 7.29-7.47 (m, 3 H), 5.24 (m, 1 H), 3.32-3.79 (m, 4 H), 2.78 (s, 2 H), 2.59 (s, 2 H), 1.47 (br. s., 4 H), 1.32 (d, J=6.7 Hz, 6 H).

Example 3

6-[(1-isopropyl-7-oxo-1,4,6,7-tetrahydro-1'H-spiro[indazole-5,4'-piperidin]-1'-yl) carbonyl]-1H-pyrrolo[3,2-b]pyridine-3-carboxamide

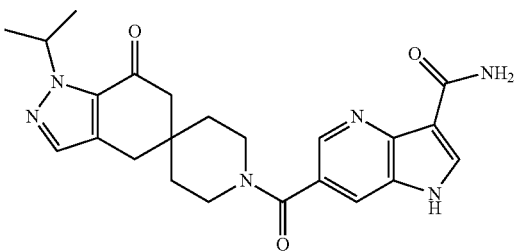 [SMILES: CC(C)n1ncc2c1C(=O)CC1(CCN(C(=O)c3cnc4c(C(N)=O)c[nH]c4c3)CC1)C2]

To a solution of 1, (3-dimethylaminopropyl)-3-ethyl carbodiimide hydrochloride (252 mg, 1.31 mmol) and 1-hydroxybenzotriazole hydrate (199 mg, 1.30 mmol) in dichloromethane (5 mL) was added 3-carbamoyl-1H-pyrrolo[3,2-b]pyridine-6-carboxylic acid (212 mg, 1.04 mmol). The mixture was stirred at room temperature for 40 minutes. 1-isopropyl-4,6-dihydrospiro[indazole-5,4'-piperidin]-7(1H)-one (312 mg, 1.26 mmol) and triethylamine (0.434 mL, 3.11 mmol) were then added and the reaction was allowed to stir at room temperature for 16 hours. The reaction was diluted with saturated aqueous ammonium chloride and extracted twice with dichloromethane. The combined organic layers were washed successively with saturated sodium bicarbonate, water, and brine. The organics were dried over sodium sulfate, filtered, and concentrated. Purification via flash column chromatography (0-100% of a 20% methanol/dichloromethane solution) afforded the title compound (254 mg, 57%). +ESI (M+H) 435.5; $^1$H NMR (400 MHz, CD$_3$OD, δ): 8.57 (d, J=1.8 Hz, 1 H), 8.26 (s, 1 H), 7.98 (d, J=1.0 Hz, 1 H), 7.43 (s, 1 H), 5.38 (m, 1 H), 3.63 (m, 4 H), 2.90 (s, 2 H), 2.66 (s, 2 H), 1.66 (m, 4 H), 1.42 (d, J=6.6 Hz, 6 H).

The compounds listed in Table 1 below were prepared using procedures analogous to those described above for the synthesis of the compounds of Examples 1-3 using the appropriate starting materials which are available commercially, prepared using preparations well-known to those skilled in the art, or prepared by a route described above. The compounds listed below were isolated initially as the free base and may be converted to a pharmaceutically acceptable salt for testing.

TABLE 1

| Example | —R² | Analytical Data |
|---|---|---|
| 4 | (3-carbamoyl-1H-indazol-6-yl) | +ESI (M + H) 435.3; $^1$H NMR (400 MHz, DMSO-d$_6$, δ): 13.64 (s, 1 H), 8.15 (d, J = 8.2 Hz, 1 H), 7.73 (d, J = 0.8 Hz, 1 H), 7.56 (s, 1 H), 7.43 (s, 1 H), 7.33-7.38 (m, 1 H), 7.18 (dd, J = 8.3, 0.9 Hz, 1 H), 5.17-5.32 (m, 1 H), 3.50-3.80 (m, 2 H), 3.22-3.38 (m, 2 H), 2.78 (br. s., 2 H), 2.59 (s, 2 H), 1.40-1.61 (m, 4 H), 1.32 (d, J = 6.3 Hz, 6 H). |
| 5 | (3-carbamoyl-1H-pyrrolo[2,3-b]pyridin-5-yl) | +ESI (M + H) 435.1; retention time 2.1 minutes. (Method A) |
| 6 | (2-carbamoyl-1H-indol-5-yl) | +ESI (M + H) 434.2; $^1$H NMR (400 MHz, DMSO-d$_6$, δ): 11.67-11.72 (m, 1 H), 7.98 (br. s., 1 H), 7.65 (s, 1 H), 7.45 (s, 1 H), 7.42 (d, J = 8.4 Hz, 1 H), 7.38 (br. s., 1 H), 7.21 (d, J = 0.4 Hz, 1 H), 7.15 (d, J = 2.5 Hz, 1 H), 5.26 (dt, J = 13.3, 6.6 Hz, 1 H), 3.38-3.54 (m, 4 H), 2.80 (s, 2 H), 2.61 (s, 2 H), 1.45-1.54 (m, 4 H), 1.35 (d, J = 6.4 Hz, 6 H). |

TABLE 1-continued

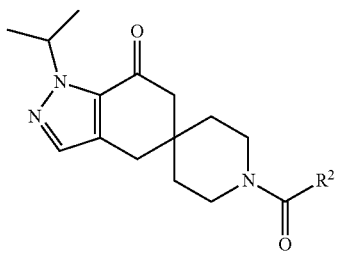

| Example | —R² | Analytical Data |
|---|---|---|
| 7 | 5-(1H-indol-3-yl)carboxamide | +ESI (M + H) 434.2; ¹H NMR (400 MHz, DMSO-$d_6$, δ): 11.68 (br. s., 1 H), 8.20 (s, 1 H), 8.08 (s, 1 H), 7.41-7.47 (m, 3 H), 7.17 (dd, J = 8.3, 1.5 Hz, 1 H), 6.81 (br. s., 1 H), 5.21-5.32 (m, 1 H), 3.42-3.71 (m, 4 H), 2.81 (s, 2 H), 2.62 (s, 2 H), 1.44-1.56 (m, 4 H), 1.36 (d, J = 6.6 Hz, 6 H). |
| 8 | 2-amino-1H-benzimidazol-5-yl | ¹H NMR (400 MHz, CD$_3$OD, δ): 8.50 (br. s., 1 H), 7.44 (s, 1 H), 7.37 (d, J = 9.2 Hz, 2 H), 7.26 (d, J = 8 Hz, 1 H), 5.37-5.44 (m, 1 H), 3.40-4.00 (m, 4 H), 2.91 (s, 2 H), 2.66 (s, 2 H), 1.50-1.80 (m, 4 H), 1.44 (d, J = 6.8 Hz, 6 H). |
| 9 | N-methyl-1H-indazole-3-carboxamide-5-yl | ¹H NMR (400 MHz, DMSO-$d_6$, δ): 13.65 (s, 1 H), 8.35 (m, 1 H), 8.13 (s, 1 H), 7.57 (d, J = 8.4 Hz, 1 H), 7.39 (s, 1 H), 7.35-7.37 (m, 1 H), 5.15-5.30 (m, 1 H), 3.3-3.8 (m, 4 H), 2.75 (m, 5 H), 2.56 (s, 2 H), 1.35-1.60 (m, 4 H), 1.29 (d, J = 6.8 Hz, 6 H). |
| 10 | N-ethyl-1H-indazole-3-carboxamide-5-yl | ¹H NMR (400 MHz, CD$_3$OD, δ): 8.43 (m, 1 H), 8.31 (s, 1 H), 7.65 (d, J = 8.8 Hz, 1 H), 7.47 (d, J = 8.8 Hz, 1 H), 7.43 (s, 1 H), 5.37-5.40 (m, 1 H), 3.65-4.00 (m, 2 H), 3.44-3.52 (m, 4 H), 2.90 (s, 2 H), 2.66 (s, 2 H), 1.50-1.80 (m, 4 H), 1.42 (d, J = 6.4 Hz, 6 H), 1.26 (t, J = 7.2 Hz, 3 H). |
| 11 | N-(2,2,2-trifluoroethyl)-1H-indazole-3-carboxamide-5-yl | ¹H NMR (400 MHz, CD$_3$OD, δ): 8.31 (s, 1 H), 7.68 (d, J = 8.8 Hz, 1 H), 7.50 (d, J = 8.8 Hz, 1 H), 7.43 (s, 1 H), 5.37-5.40 (m, 1 H), 4.09-4.16 (m, 2 H), 3.65-4.00 (m, 2 H), 3.45-3.64 (m, 2 H), 2.90 (s, 2 H), 2.66 (s, 2 H), 1.50-1.80 (m, 4 H), 1.42 (d, J = 6.4 Hz, 6 H). |
| 12 | 1H-indole-2-carboxamide-6-yl | +ESI (M + H) 434.3; ¹H NMR (400 MHz, DMSO-$d_6$, δ): 11.67 (s, 1 H), 7.98 (br. s., 1 H), 7.60 (d, J = 8.2 Hz, 1 H), 7.40-7.44 (m, 2 H), 7.36-7.40 (m, 1 H), 7.09-7.13 (m, 1 H), 7.01 (dd, J = 8.3, 1.5 Hz, 1 H), 5.19-5.29 (m, 1 H), 3.31-3.70 (m, 4 H), 2.78 (s, 2 H), 2.59 (s, 2 H), 1.38-1.54 (m, 4 H), 1.33 (d, J = 6.6 Hz, 6 H). |
| 13 | 2-(methylamino)quinolin-7-yl | +ESI (M + H) 432.3; HPLC retention time 2.18 minutes (Method A) |

TABLE 1-continued

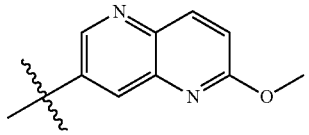 [SMILES: *c1cnc2ccc(OC)nc2c1]

| Example | —R² | Analytical Data |
|---|---|---|
| 14 | 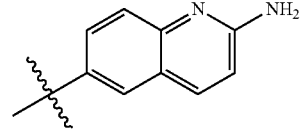 [SMILES: *c1ccc2nc(N)ccc2c1] | +ESI (M + H) 433.3; HPLC retention time 2.52 minutes (Method A). ¹H NMR (500 MHz, CDCl₃, δ) 8.78 (d, J = 2.20 Hz, 1 H), 8.13 (d, J = 1.95 Hz, 1 H), 8.03 (d, J = 9.27 Hz, 1 H), 7.44 (dd, J = 9.03, 2.68 Hz, 1 H), 7.40 (s, 1 H), 7.10 (d, J = 2.68 Hz, 1 H), 5.35-5.43 (m, 1 H), 3.96 (s, 3 H), 3.81 (br. s., 2 H), 3.50 (br. s., 2 H), 2.84 (s, 2 H), 2.63 (s, 2 H), 1.54-1.79 (m, 4 H), 1.47 (d, J = 6.34 Hz, 6 H). |
| 15 | 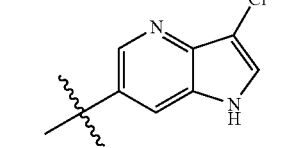 | +ESI (M + H) 418.2; HPLC retention time 2.06 minutes (Method A). |
| 16 | 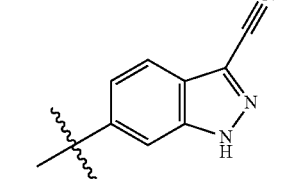 | +ESI (M + H) 426.1; HPLC retention time 2.18 minutes (Method A). |
| 17 | 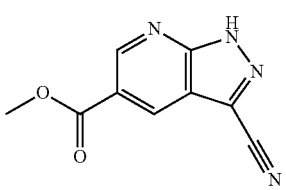 | +ESI (M + H) 417.2; ¹H NMR (400 MHz, DMSO-d₆, δ): 7.91 (dd, J = 8.4, 0.8 Hz, 1 H), 7.73 (s, 1 H), 7.42 (s, 1 H), 7.33 (dd, J = 8.4, 1.2 Hz, 1 H) 5.19-5.28 (m, 1 H), 3.49-3.78 (m, 4 H), 2.77 (br. s., 2 H), 2.59 (s, 2 H), 1.36-1.60 (m, 4 H), 1.33 (m, 6 H). |

Example 18

5-[(1-isopropyl-7-oxo-1,4,6,7-tetrahydro-1'H-spiro [indazole-5,4'-piperidin]-1'-yl)carbonyl]-1H-pyrazolo[3,4-b]pyridine-3-carboxamide

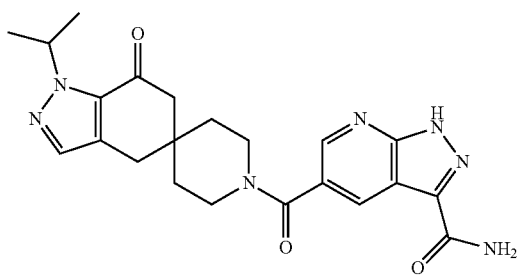 [SMILES: CC(C)n1ncc2c1C(=O)CC1(CCN(C(=O)c3cnc4[nH]nc(C(N)=O)c4c3)CC1)C2]

Step 1. methyl 3-cyano-1H-pyrazolo[3,4-b]pyridine-5-carboxylate

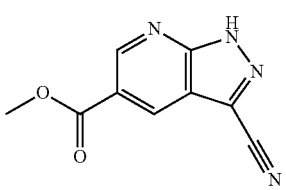

Methyl 3-bromo-1H-pyrazolo[3,4-b]pyridine-5-carboxylate (1.28 g, 5.01 mmol) was combined with N,N-dimethylacetamide (34 mL). To this mixture was added zinc dust (195 mg, 2.90 mmol) and zinc cyanide (1.20 g, 10.2 mmol). Nitrogen was bubbled through the mixture for 30 minutes. Then 1,1'-bis(diphenylphosphino)ferrocene-palladium (II) dichloride dichloromethane complex (611 mg, 0.749 mmol) was added and the reaction vessel was sealed. The reaction was heated to 120° C. for 65 hours. The reaction was diluted with 20% methanol/ethyl acetate and filtered through Celite. The filtrate was diluted with water and transferred to a separatory funnel. The phases were separated, and the organics were washed again with water and brine. The organics were then dried over sodium sulfate, filtered, and concentrated. Purification by flash column chromatography (0-75% ethyl acetate/ heptanes) gave the title compound (390 mg, 39%). +ESI (M+H) 203.1.

Step 2. 5-(1-isopropyl-7-oxo-1,4,6,7-tetrahydrospiro [indazole-5,4'-piperidine]-1'-ylcarbonyl)-1H-pyrazolo[3,4-b]pyridine-3-carbonitrile

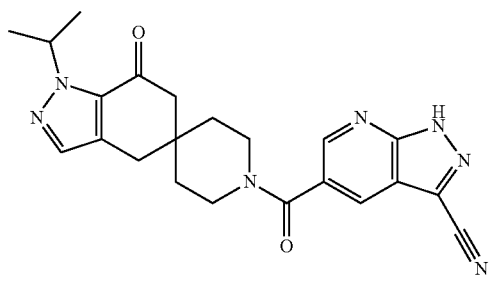 [SMILES: CC(C)n1ncc2c1C(=O)CC1(CCN(C(=O)c3cnc4[nH]nc(C#N)c4c3)CC1)C2]

Methyl 3-cyano-1H-pyrazolo[3,4-b]pyridine-5-carboxylate (390 mg, 1.93 mmol) was dissolved in methanol (20 mL). Aqueous 1 N sodium hydroxide (11 mL, 10 mmol) was added and the reaction was allowed to stir at room temperature for 22 hours. The crude was concentrated to remove the methanol and was then washed once with dichloromethane. The aqueous layer was acidified to pH=2 with 6 N aqueous hydrochloric acid and the resulting solids were collected by filtration (172 mg).

To the carboxylic acid (170 mg, 0.91 mmol) was added 4-dimethylaminopyridine (27.6 mg, 0.22 mmol), 2-propanephosphonic acid cyclic anhydride (0.65 mL, 1.1 mmol), and dichloromethane (3 mL). The mixture was stirred at room temperature for 1 hour. Triethylamine (0.51 mL, 3.6 mmol) and 1-isopropyl-4,6-dihydrospiro[indazole-5,4'-piperidine]-7(1H)-one (293 mg, 0.913 mmol) were then added and the reaction was stirred for 17 hours. Additional triethylamine (0.30 mL, 2.2 mmol) was added and the reaction was stirred for another 24 hours. The reaction was diluted with water and the layers were separated. The aqueous was extracted twice with dichloromethane. The combined organics were dried over sodium sulfate, filtered, and concentrated. Purification by column chromatography (0-100% of a 10% methanol in dichloromethane solution/dichloromethane) gave the title compound (177 mg, 47%). +ESI (M+H) 418.3; $^1$H NMR (500 MHz, CHLOROFORM-d, δ): 13.59 (br. s., 1 H), 8.81 (d, J=2.0 Hz, 1 H), 8.38 (d, J=1.7 Hz, 1 H), 7.44 (s, 1 H), 5.40 (m, 1 H), 3.77-3.98 (m, 2 H), 3.44-3.63 (m, 2 H), 2.86 (s, 2 H), 2.66 (s, 2 H), 1.54-1.85 (m, 4 H), 1.47 (d, J=6.6 Hz, 6 H).

Step 3. 5-[(1-isopropyl-7-oxo-1,4,6,7-tetrahydro-1'H-spiro[indazole-5,4'-piperidin]-1'-yl)carbonyl]-1H-pyrazolo[3,4-b]pyridine-3-carboxamide A solution of 5-(1-isopropyl-7-oxo-1,4,6,7-tetrahydrospiro[indazole-5,4'-piperidine]-1'-ylcarbonyl)-1H-pyrazolo[3,4-b]pyridine-3-carbonitrile (177 mg, 0.424 mmol) in methanol (2 mL) was added to a 0° C. solution of urea hydrogen peroxide (552 mg, 5.70 mmol) in 1 N aqueous sodium hydroxide (4.24 mL, 4.24 mmol). The reaction was allowed to warm to room temperature and stir for 22 hours. The methanol was removed under reduced pressure and the residue was diluted with water and saturated aqueous ammonium chloride. The mixture was extracted with dichloromethane (3×). The combined organics were dried over sodium sulfate, filtered, and concentrated. Purification by reversed-phase HPLC gave the title compound. Analytical LCMS: +ESI (M+H) 436.2; retention time 2.11 minutes (Method A).

Example 19

5-[(1-isopropyl-7-oxo-1,4,6,7-tetrahydro-1'H-spiro [indazole-5,4'-piperidin]-1'-yl)carbonyl]-1H-pyrrolo [2,3-b]pyridine-2-carboxamide

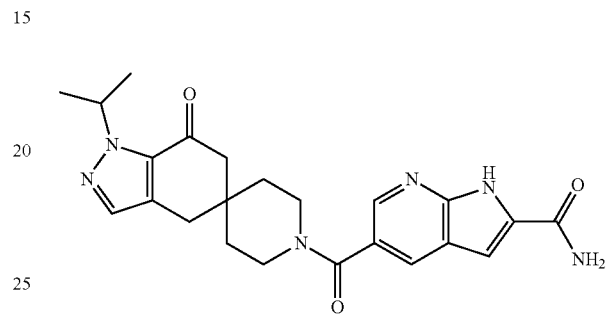

Step 1. ethyl 2-cyano-1H-pyrrolo[2,3-b]pyridine-5-carboxylate

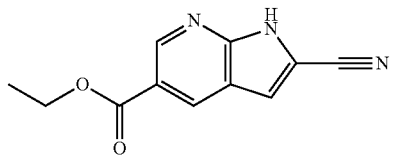 [SMILES: CCOC(=O)c1cnc2[nH]c(C#N)cc2c1]

The title compound was prepared by a method analogous to that described in Step 1 of Example 18, using ethyl 2-bromo-1H-pyrrolo[2,3-b]pyridine-5-carboxylate. +ESI (M+H) 216.3; $^1$H NMR (400 MHz, METHANOL-$d_4$, δ): 9.02 (d, J=2.1 Hz, 1 H), 8.73 (d, J=2.0 Hz, 1 H), 7.35 (s, 1 H), 4.41 (q, J=7.2 Hz, 2 H), 1.40 (t, J=7.1 Hz, 3 H).

Step 2. 5-(1-isopropyl-7-oxo-1,4,6,7-tetrahydrospiro [indazole-5,4'-piperidine]-1'-ylcarbonyl)-1H-pyrrolo [2,3-b]pyridine-2-carbonitrile

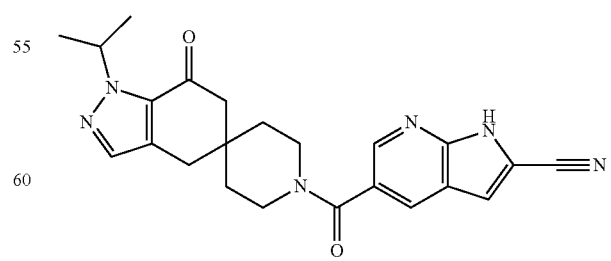

To ethyl 2-cyano-1H-pyrrolo[2,3-b]pyridine-5-carboxylate (36 mg, 0.17 mmol) was added methanol (1 mL), tetrahydrofuran (1 mL), and water (1 mL), followed by 2 N aqueous lithium hydroxide (0.17 mL, 0.33 mmol). The reaction was stirred at room temperature overnight and was then concentrated. The crude was taken up in water and the pH was adjusted to 4 using 1 N aqueous hydrochloric acid. The mixture was extracted with ethyl acetate (3×). The combined organics were dried over sodium sulfate, filtered, and concentrated to provide the 2-cyano-1H-pyrrolo[2,3-b]pyridine-5-carboxylic acid. The title compound was then prepared by a method analogous to that described in Example 1, using 2-cyano-1H-pyrrolo[2,3-b]pyridine-5-carboxylic acid. −ESI (M−H) 415.1.

Step 3. 5-[(1-isopropyl-7-oxo-1,4,6,7-tetrahydro-1′H-spiro[indazole-5,4′-piperidin]-1′-yl)carbonyl]-1H-pyrrolo[2,3-b]pyridine-2-carboxamide The title compound was prepared by a method analogous to that described in Step 3 of Example 18. Analytical LCMS: +ESI (M+H) 435.1; retention time 2.17 minutes (Method A).

Example 20

1-isopropyl-1′-{[2-(methylamino)-1H-benzimidazol-5-yl]carbonyl}-1,4-dihydrospiro[indazole-5,4′-piperidin]-7(6H)-one

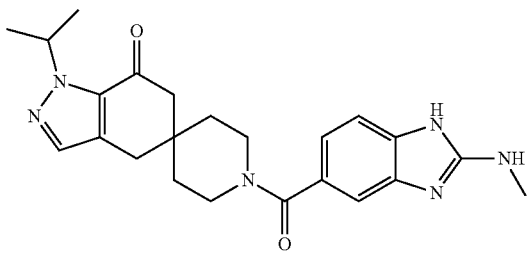 [SMILES: CNc1nc2cc(C(=O)N3CCC4(CC3)CC(=O)c3c(cnn3C(C)C)C4)ccc2[nH]1]

Step 1. 1′-(3,4-diaminobenzoyl)-1-isopropyl-4,6-dihydrospiro[indazole-5,4′-piperidin]-7(1H)-one

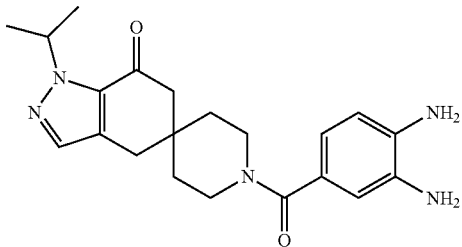 [SMILES: CC(C)n1ncc2c1C(=O)CC1(CCN(C(=O)c3ccc(N)c(N)c3)CC1)C2]

The title compound was prepared by a method analogous to that described for Example 3, using 3,4-diaminobenzoic acid. $^1$H NMR (400 MHz, DMSO-d$_6$, δ): 7.45 (s, 1 H), 6.60 (s, 1 H), 6.46 (s, 1 H), 5.76 (s, 1 H), 5.24-5.30 (m, 1 H), 4.78 (s, 2 H), 4.56 (s, 2 H), 3.35-3.55 (m, 4 H), 2.79 (s, 2 H), 2.59 (s, 2 H), 2.40-2.50 (m, 1 H), 1.42-1.46 (m, 3 H), 1.35 (d, J=6.8 Hz, 6 H).

Step 2. 1-isopropyl-1′-{[2-(methylamino)-1H-benzimidazol-5-yl]carbonyl}-1,4-dihydrospiro[indazole-5,4′-piperidin]-7(6H)-one A mixture of 1′-(3,4-diaminobenzoyl)-1-isopropyl-4,6-dihydrospiro[indazole-5,4′-piperidin]-7(1H)-one (0.1 g, 0.3 mmol) and isothiocyanatomethane (19 mg, 0.3 mmol) was dissolved in tetrahydrofuran (3 mL). The reaction was heated to reflux and stirred for 6 hours. The reaction mixture was concentrated, and the residue was poured into cold water. The solution was extracted with ethyl acetate (3×20 mL). The combined organics were dried over sodium sulfate, filtered, and concentrated to provide 1-(2-amino-4-(1-isopropyl-7-oxo-1,4,6,7-tetrahydrospiro[indazole-5,4′-piperidine]-1′-ylcarbonyl)phenyl)-3-methylthiourea (37 mg, 27%).

The crude product was dissolved in ethanol (2 mL) and methyl iodide (147 mg, 1.0 mmol) was added. The reaction was heated to reflux and stirred overnight. The reaction was concentrated and the residue was basified to pH=9 with ammonium hydroxide. The mixture was extracted with dichloromethane (3×20 mL). The combined organics were dried over sodium sulfate, filtered, and concentrated. Purification by reversed-phase HPLC gave the title compound (28 mg, 83%) as an off white solid. $^1$H NMR (400 MHz, CDCl$_3$, δ): 7.39 (s, 1 H), 7.13 (s, 1 H), 7.05-7.07 (m, 1 H), 6.99-7.01 (m, 1 H), 5.33-5.43 (m, 1 H), 3.44-3.89 (m, 4 H), 2.91 (s, 3 H), 2.86 (s, 2 H), 2.60 (s, 2 H), 1.50-1.80 (m, 4 H), 1.46 (d, J. 6.8 Hz, 6 H).

Example 21

5-[(1-isopropyl-7-oxo-1,4,6,7-tetrahydro-1′H-spiro[indazole-5,4′-piperidin]-1′-yl)carbonyl]-1H-benzimidazole-2-carboxamide

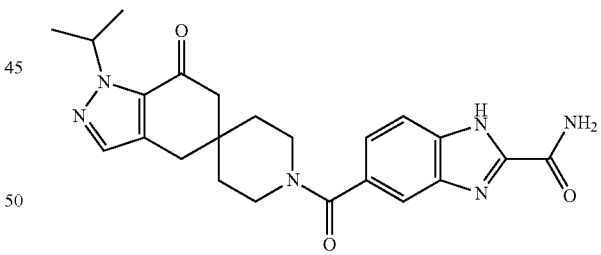

A mixture of 1′-(3,4-diaminobenzoyl)-1-isopropyl-4,6-dihydrospiro[indazole-5,4′-piperidin]-7(1H)-one (500 mg, 1.3 mmol), 2-chloroacetamide (200 mg, 2.1 mmol), sulfur (200 mg, 6.3 mmol), and triethylamine (1 mL, 7 mmol) in N,N-dimethylformamide (5 mL) was stirred at 65° C. overnight. The reaction mixture was cooled to 0° C., diluted with water (10 mL), and extracted with ethyl acetate (2×20 mL). The combined organics were dried over sodium sulfate, filtered, and concentrated. Purification by column chromatography gave the title compound (252 mg, 44%) as a yellow solid. $^1$H NMR (400 MHz, CD$_3$OD, δ): 7.60-7.90 (m, 2 H), 7.30-7.50 (m, 2 H), 5.37-5.40 (m, 1 H), 3.40-4.00 (m, 4 H), 2.89 (s, 2 H), 2.65 (s, 2 H), 1.50-1.80 (m, 4 H), 1.42 (d, J=6.4 Hz, 6 H).

Example 22

3-[(1-isopropyl-7-oxo-1,4,6,7-tetrahydro-1'H-spiro[indazole-5,4'-piperidin]-1'-yl)carbonyl]-6-methoxyquinoline-7-carboxamide

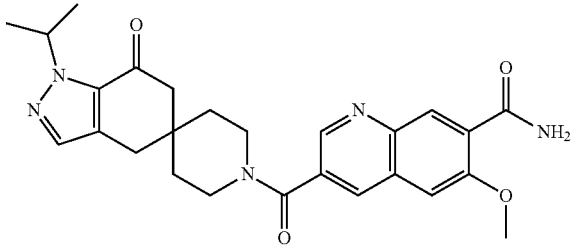 [SMILES: COc1cc2cc(C(=O)N3CCC4(CC3)CC(=O)c3c(cnn3C(C)C)C4)cnc2cc1C(N)=O]

Step 1: 1'-(7-bromo-6-methoxyquinoline-3-carbonyl)-1-isopropyl-4,6-dihydrospiro[indazole-5,4'-piperidin]-7(1H)-one

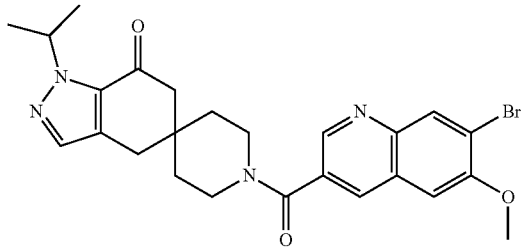 [SMILES: COc1cc2cc(C(=O)N3CCC4(CC3)CC(=O)c3c(cnn3C(C)C)C4)cnc2cc1Br]

The title compound was prepared by a method analogous to that described for Example 2, using 7-bromo-6-methoxyquinoline-3-carboxylic acid. +ESI (M+H+1) 513.2; $^1$H NMR (400 MHz, CDCl$_3$, δ): 8.71 (d, J=2.15 Hz, 1 H), 8.29 (s, 1 H), 8.05 (d, J=2.15 Hz, 1 H), 7.32 (s, 1 H), 7.05 (s, 1 H), 5.25-5.37 (m, 1 H), 3.96 (s, 3 H), 3.65-3.91 (m, 2 H), 3.37-3.58 (m, 2 H), 2.77 (s, 2 H), 2.55 (s, 2 H), 1.59-1.73 (m, 2 H), 1.46-1.59 (m, 2 H), 1.39 (d, J=6.44 Hz, 6 H).

Step 2: 3-(1-isopropyl-7-oxo-1,4,6,7-tetrahydrospiro[indazole-5,4'-piperidine]-1'-ylcarbonyl)-6-methoxyquinoline-7-carbonitrile

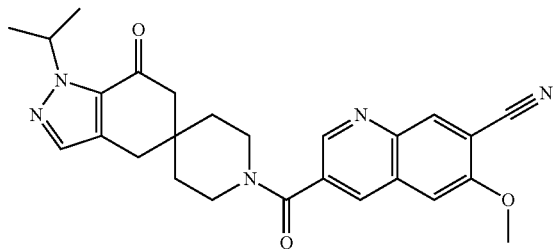 [SMILES: COc1cc2cc(C(=O)N3CCC4(CC3)CC(=O)c3c(cnn3C(C)C)C4)cnc2cc1C#N]

The title compound was prepared by a method analogous to that described for Intermediate 6, using 1'-(7-bromo-6-methoxyquinoline-3-carbonyl)-1-isopropyl-4,6-dihydrospiro[indazole-5,4'-piperidin]-7(1H)-one. +ESI (M+H) 458.4; $^1$H NMR (400 MHz, CDCl$_3$, δ): 8.82 (d, J=1.95 Hz, 1 H), 8.37 (s, 1 H), 8.10 (d, J=1.56 Hz, 1 H), 7.35 (s, 1 H), 7.14 (s, 1 H), 5.33 (m, 1 H), 4.02 (s, 3 H), 3.70-3.91 (m, 2 H), 3.36-3.54 (m, 2 H), 2.80 (s, 2 H), 2.58 (s, 2 H), 1.65-1.77 (m, 2 H), 1.51-1.62 (m, 2 H), 1.42 (d, J=4.49 Hz, 6 H).

Step 3: 3-[(1-isopropyl-7-oxo-1,4,6,7-tetrahydro-1'H-spiro[indazole-5,4'-piperidin]-1'-yl)carbonyl]-6-methoxyquinoline-7-carboxamide The title compound was prepared by a method analogous to that described in Step 4 of Intermediate 6, using 3-(1-isopropyl-7-oxo-1,4,6,7-tetrahydrospiro[indazole-5,4'-piperidine]-1'-ylcarbonyl)-6-methoxyquinoline-7-carbonitrile. +ESI (M+H) 476.4; $^1$H NMR (400 MHz, CD$_3$OD, δ): 8.77 (s, 1 H), 8.52 (s, 1 H), 8.36 (s, 1 H), 7.55 (s, 1 H), 7.42 (s, 1 H), 5.31-5.43 (m, 1 H), 4.08 (s, 3 H), 3.84-4.00 (m, 1 H), 3.69-3.83 (m, 1 H), 3.48-3.58 (m, 2 H), 2.90 (s, 2 H), 2.65 (br. s., 2 H), 1.53-1.78 (m, 4 H), 1.35-1.45 (m, 6 H).

Example 23

6-[(1-isopropyl-7-oxo-1,4,6,7-tetrahydro-1'H-spiro[indazole-5,4'-piperidin]-1'-yl)carbonyl]-1H-pyrrolo[3,2-b]pyridine-3-carbonitrile

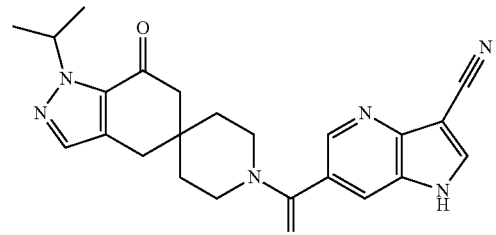

Step 1: 1'-(3-bromo-1H-pyrrolo[3,2-b]pyridine-6-carbonyl)-1-isopropyl-4,6-dihydrospiro[indazole-5,4'-piperidin]-7(1H)-one

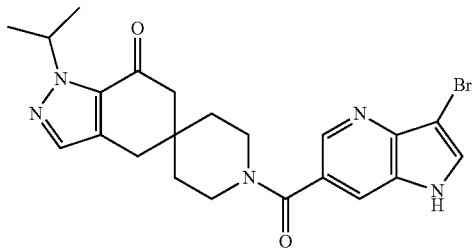 [SMILES: CC(C)n1ncc2c1C(=O)CC1(CCN(C(=O)c3cnc4c(Br)c[nH]c4c3)CC1)C2]

The title compound was prepared by a method analogous to that described for Example 3, using 3-bromo-1H-pyrrolo[3,2-b]pyridine-6-carboxylic acid. +ESI (M+H+1) 472.1; $^1$H NMR (400 MHz, DMSO-d$_6$, δ): 11.85 (br. s., 1 H), 8.39 (d, J=1.8 Hz, 1 H), 7.93 (s, 1 H), 7.81 (d, J=1.8 Hz, 1 H), 7.43 (s, 1 H), 5.24 (m, 1 H), 3.68 (m, 1 H), 3.40 (m, 3 H), 2.79 (s, 2 H), 2.60 (s, 2 H), 1.49 (m, 4 H), 1.33 (d, J=6.6 Hz, 6 H).

Step 2: 6-[(1-isopropyl-7-oxo-1,4,6,7-tetrahydro-1'H-spiro[indazole-5,4'-piperidin]-1'-yl)carbonyl]-1H-pyrrolo[3,2-b]pyridine-3-carbonitrile To a mixture of 1'-(3-bromo-1H-pyrrolo[3,2-b]pyridine-6-carbonyl)-1-isopropyl-4,6-dihydrospiro[indazole-5,4'-piperidin]-7(1H)-one (500 mg, 1.1 mmol), zinc dust (70 mg, 1.1 mmol), and zinc cyanide (187 mg, 1.60 mmol) was added N,N-dimethylacetamide (9 mL). The reaction vial was capped and nitrogen gas was bubbled through the mixture for 15 minutes. Meanwhile, a mixture of palladium(II) acetate (24 mg, 0.11 mmol), 4,5-bis(diphenylphosphino)-9,9-dimethylxanthene (68 mg, 0.12 mmol), and zinc powder (7 mg, 0.13 mmol) in N,N-dimethylacetamide (1.5 mL) was heated to 80° C. for 15 minutes to give a reddish brown solution. This palladium solution was then added via syringe to the substrate mixture. The reaction was heated to 100° C. and stirred for 3 days. The reaction was cooled to room temperature and diluted with ethyl acetate (100 mL). The solution was filtered through Celite and the filtrate was concentrated. 50 mg of the crude residue was subjected to purification by reversed-phase HPLC to give the title compound (25.8 mg). +ESI (M+H) 417.1; HPLC retention time 2.32 minutes (Method A).

Example 24

2-({3-[(1-isopropyl-7-oxo-1,4,6,7-tetrahydro-1'H-spiro[indazole-5,4'-piperidin]-1'-yl)carbonyl]quinolin-6-yl}oxy)acetamide

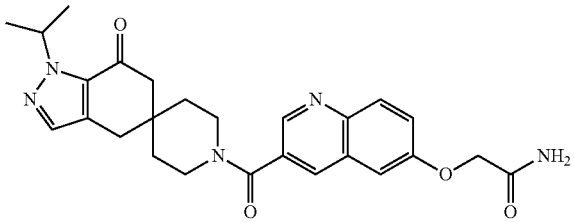 [SMILES: CC(C)n1ncc2c1C(=O)CC1(CCN(C(=O)c3cnc4ccc(OCC(N)=O)cc4c3)CC1)C2]

Step 1: 2-(2-chloro-3-(1-isopropyl-7-oxo-1,4,6,7-tetrahydrospiro[indazole-5,4'-piperidine]-1'-ylcarbonyl)quinolin-6-yloxy)acetamide

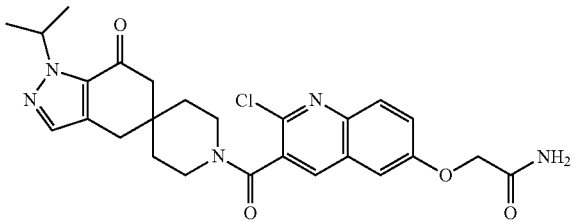 [SMILES: CC(C)n1ncc2c1C(=O)CC1(CCN(C(=O)c3cc4cc(OCC(N)=O)ccc4nc3Cl)CC1)C2]

6-(2-tert-butoxy-2-oxoethoxy)-2-chloroquinoline-3-carboxylic acid and 1-isopropyl-4,6-dihydrospiro[indazole-5,4'-piperidin]-7(1H)-one were coupled by a method analogous to that described for Example 1 to give tert-butyl 2-(2-chloro-3-(1-isopropyl-7-oxo-1,4,6,7-tetrahydrospiro[indazole-5,4'-piperidine]-1'-ylcarbonyl)quinolin-6-yloxy)acetate. This material (30 mg, 0.053 mmol) was suspended in ammonia (2 mL, 10 mmol, 7 M in methanol) and stirred at room temperature for 18 hours. The reaction was concentrated to give the title compound (27 mg, 100%). +ESI (M+H) 510.4.

Step 2: 2-({3-[(1-isopropyl-7-oxo-1,4,6,7-tetrahydro-1'H-spiro[indazole-5,4'-piperidin]-1'-yl)carbonyl]quinolin-6-yl}oxy)acetamide Methanol (1.5 mL) and ethyl acetate (1.5 mL) were added to 2-(2-chloro-3-(1-isopropyl-7-oxo-1,4,6,7-tetrahydrospiro[indazole-5,4'-piperidine]-1'-ylcarbonyl)quinolin-6-yloxy)acetamide (27 mg, 0.053 mmol). Palladium hydroxide (15 mg) was then added and the reaction was pressurized to 40 psi hydrogen and agitated at room temperature for 20 hours. The reaction mixture was filtered through Celite and concentrated. Purification via reversed-phase HPLC gave the title compound (2.1 mg, 8%). +ESI (M+H) 476.2; HPLC retention time 2.11 minutes (Method A).

Example 25

1'-[(2-aminoquinolin-7-yl)carbonyl]-1-isopropyl-1,4-dihydrospiro[indazole-5,4'-piperidin]-7(6H)-one

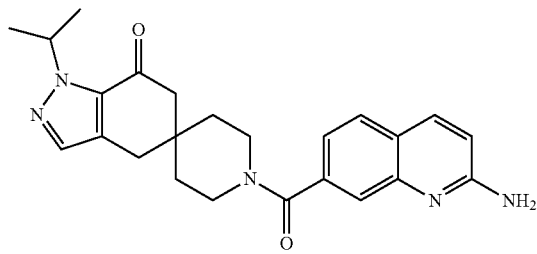 [SMILES: CC(C)n1ncc2c1C(=O)CC1(CCN(C(=O)c3ccc4ccc(N)nc4c3)CC1)C2]

Step 1: 1'-(2-(tert-butylamino)quinoline-7-carbonyl)-1-isopropyl-4,6-dihydrospiro[indazole-5,4'-piperidin]-7(1H)-one

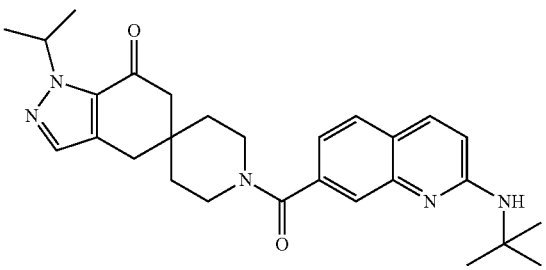 [SMILES: CC(C)n1ncc2c1C(=O)CC1(CCN(C(=O)c3ccc4ccc(NC(C)(C)C)nc4c3)CC1)C2]

The title compound was prepared by a method analogous to that described for Example 3, using 2-(tert-butylamino)quinoline-7-carboxylic acid. +APCI (M+H) 474.6; $^1$H NMR (400 MHz, CDCl$_3$, δ): 7.72 (d, J=8.8 Hz, 1 H), 7.64 (s, 1 H), 7.55 (d, J=8.2 Hz, 1 H), 7.36 (s, 1 H), 7.16 (dd, J=8.1, 1.3 Hz, 1H), 6.59 (d, J=9.2 Hz, 1 H), 5.36 (quin, J=6.6 Hz, 1 H), 3.31-3.96 (m, 4 H), 2.79 (s, 2 H), 2.58 (s, 2 H), 1.55-1.75 (m, 4 H), 1.52 (s, 9 H), 1.44 (d, J=6.4 Hz, 6 H).

Step 2: 1'-[(2-aminoquinolin-7-yl)carbonyl]-1-isopropyl-1,4-dihydrospiro[indazole-5,4'-piperidin]-7(6H)-one Trifluoroacetate Salt Trifluoroacetic acid (0.90 mL, 12 mmol) was added to 1'-(2-(tert-butylamino)quinoline-7-carbonyl)-1-isopropyl-4,6-dihydrospiro[indazole-5,4'-piperidin]-7(1H)-one (50 mg, 0.11 mmol). The reaction was heated to 70° C. for 3 hours, then cooled to room temperature and left stirring overnight. The reaction was concentrated to dryness and purification by reversed-phase HPLC gave the title compound (41 mg, 93%). +ESI (M+H) 418.2; HPLC retention time 2.11 minutes (Method A). $^1$H NMR (500 MHz, CD$_3$OD, δ) 8.36 (d, J=9.27 Hz, 1 H), 7.97 (d, J=8.05 Hz, 1 H), 7.66 (s, 1 H), 7.53 (dd, J=8.17, 1.34 Hz, 1 H), 7.44 (s, 1 H), 7.12 (d, J=9.27 Hz, 1 H), 5.39 (quint, J=13.23, 6.68 Hz, 1 H), 3.91 (br. s., 1 H), 3.76 (br. s., 1 H), 3.46 (br. s., 2 H), 2.92 (s, 2 H), 2.67 (d, J=7.81 Hz, 2 H), 1.74 (br. s., 2 H), 1.59 (br. s., 2 H), 1.43 (br. s., 6 H).

The compounds listed in Table 2 below were prepared using procedures analogous to those described above for the synthesis of the compounds of Examples 1-3 using the appro priate starting materials which are available commercially, prepared using preparations well-known to those skilled in the art, or prepared by a route described above. The compounds listed below were isolated initially as the free base and may be converted to a pharmaceutically acceptable salt for testing.

TABLE 2

| Example | —R² | Analytical Data |
|---|---|---|
| 26 | (5-indazolyl-3-carboxamide) | +APCI (M + H) 449.5; ¹H NMR (400 MHz, DMSO-d₆, δ): 13.66 (br. s., 1 H), 8.17 (s, 1 H), 7.77 (br. s., 1 H), 7.59-7.64 (m, 1 H), 7.35-7.43 (m, 3 H), 3.33-3.83 (m, 4 H), 2.82 (br. s., 2 H), 2.62 (s, 2 H), 1.56 (s, 9 H), 1.33-1.53 (m, 4 H). |
| 27 | (pyrazolopyridine-3-carboxamide) | +ESI (M + H) 449.2; retention time 2.31 minutes. (Method A) |

The compounds listed in Table 3 below were prepared using procedures analogous to those described above for the synthesis of the compounds of Examples 1-3 using the appropriate starting materials which are available commercially, prepared using preparations well-known to those skilled in the art, or prepared by a route described above. The compounds listed below were isolated initially as the free base and may be converted to a pharmaceutically acceptable salt for testing.

TABLE 3

| Example | —R2 | Analytical Data |
|---|---|---|
| 28 | (6-indazolyl-3-carboxamide) | +ESI (M + H) 448.2; ¹H NMR (400 MHz, DMSO-d₆, δ): 11.65 (br. s., 1 H), 8.13 (d, J = 8.0 Hz, 1 H), 8.08 (d, J = 2.2 Hz, 1 H), 7.81 (s, 1 H), 7.43 (s, 1 H), 7.36 (br. s., 1 H), 7.10 (d, J = 8.0 Hz, 1 H), 6.79 (br. s., 1 H), 3.34-3.67 (m, 4 H), 2.77 (s, 2 H), 2.55 (s, 2 H), 1.51 (s, 9 H), 1.42-1.50 (m, 4 H). |

TABLE 3-continued

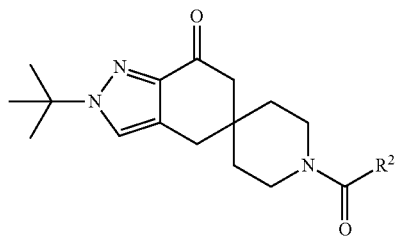

| Example | —R2 | Analytical Data |
|---|---|---|
| 29 | 1H-indazole-3-carboxamide (6-yl) | +ESI (M + H) 449.2; ¹H NMR (400 MHz, DMSO-$d_6$, δ): 13.63 (s, 1 H), 8.14 (d, J = 8.4 Hz, 1 H), 7.78 (s, 1 H), 7.73 (s, 1 H), 7.55 (s, 1 H), 7.34 (s, 1 H), 7.18 (dd, J = 8.3, 1.3 Hz, 1 H), 3.50-3.72 (m, 2 H), 3.21-3.39 (m, 2 H), 2.74 (s, 2 H), 2.53 (s, 2 H), 1.49 (s, 9 H), 1.22-1.61 (m, 4 H). |
| 30 | 1H-pyrrolo[2,3-b]pyridine-3-carboxamide (5-yl) | +ESI (M + H) 449.2; HPLC retention time 1.99 minutes. (Method A) |
| 31 | 1H-pyrazolo[3,4-b]pyridine-3-carboxamide (5-yl) | +ESI (M + H) 449.3; ¹H NMR (400 MHz, DMSO-$d_6$, δ): 13.67 (s, 1 H), 8.17 (s, 1 H), 7.81 (s, 1 H), 7.75-7.79 (m, 1 H), 7.62 (d, J = 8.6 Hz, 1 H), 7.41 (dd, J = 8.6, 1.6 Hz, 2 H), 3.31-3.71 (m, 4 H), 2.77 (br. s., 2 H), 2.55 (s, 2 H), 1.52 (s, 9 H), 1.39-1.50 (m, 4 H). |
| 32 | 1H-indole-2-carboxamide (5-yl) | +ESI (M + H) 448.2; ¹H NMR (400 MHz, DMSO-$d_6$, δ): 11.70 (d, J = 1.4 Hz, 1 H), 7.99 (br. s., 1 H), 7.82 (s, 1 H), 7.66 (s, 1 H), 7.42 (d, J = 8.6 Hz, 1 H), 7.39 (br. s., 1 H), 7.21 (dd, J = 8.4, 1.6 Hz, 1 H), 7.16 (d, J = 1.4 Hz, 1 H), 3.49 (br. s., 4 H), 2.78 (s, 2 H), 2.56 (s, 2 H), 1.50 (s, 9 H), 1.48 (br. s., 4 H). |
| 33 | 1H-indole-3-carboxamide (5-yl) | −ESI (M − H) 446.2; ¹H NMR (400 MHz, DMSO-$d_6$, δ): 11.68 (br. s., 1 H), 8.20 (d, J = 0.8 Hz, 1 H), 8.07 (d, J = 2.7 Hz, 1 H), 7.82 (s, 1 H), 7.46 (br. s., 1 H), 7.43 (d, J = 8.4 Hz, 1 H), 7.17 (dd, J = 8.3, 1.7 Hz, 1 H), 6.82 (br. s., 1 H), 3.50 (br. s., 4 H), 2.78 (s, 2 H), 2.55 (s, 2 H), 1.53 (s, 9 H), 1.48 (br. s., 4 H). |
| 34 | 1H-indole-2-carboxamide (6-yl) | +ESI (M + H) 448.4; ¹H NMR (400 MHz, DMSO-$d_6$, δ): 11.67 (d, J = 1.6 Hz, 1 H), 7.98 (br. s., 1 H), 7.79 (s, 1 H), 7.60 (d, J = 8.2 Hz, 1 H), 7.41 (s, 1 H), 7.36-7.40 (m, 1 H), 7.09-7.13 (m, 1 H), 7.02 (dd, J = 8.3, 1.5 Hz, 1 H), 3.43 (br. s., 4 H), 2.75 (s, 2 H), 2.52 (s, 2 H), 1.37-1.55 (m, 13 H). |
| 35 | 2-amino-1H-benzimidazole (6-yl) | ¹H NMR (400 MHz, CD$_3$OD, δ): 8.36 (br. s., 1 H), 7.75 (s, 1 H), 7.34-7.36 (m, 2 H), 7.24-7.26 (m, 1 H), 3.50-3.88 (m, 4 H), 2.91 (s, 2 H), 2.68 (s, 2 H), 1.62 (s, 9 H), 1.56-1.70 (m, 4 H). |

TABLE 3-continued

| Example | —R2 | Analytical Data |
|---|---|---|
| 36 | (5-substituted 1H-indazole-3-C(O)NH-ethyl) | $^1$H NMR (400 MHz, CD$_3$OD, δ): 8.42-8.45 (m, 1 H), 8.31 (s, 1 H), 7.74 (s, 1 H), 7.65 (d, J = 8.8 Hz, 1 H), 7.47 (d, J = 8.8 Hz, 1 H), 3.65-4.00 (m, 2 H), 3.44-3.60 (m, 4 H), 2.90 (s, 2 H), 2.66 (s, 2 H), 1.50-1.80 (m, 4 H), 1.60 (s, 9 H), 1.26 (t, J = 7.2 Hz, 3 H). |
| 37 | (5-substituted 1H-indazole-3-C(O)NH-methyl) | $^1$H NMR (400 MHz, DMSO-d$_6$, δ): 13.70 (s, 1 H), 8.40-8.41 (m, 1 H), 8.19 (s, 1 H), 7.83 (s, 1 H), 7.63 (d, J = 8.8 Hz, 1 H), 7.43 (d, J = 8.4 Hz, 1 H), 3.40-3.80 (m, 4 H), 2.81 (d, J = 4.4 Hz, 3 H), 2.80 (s, 2 H), 2.57 (s, 2 H), 1.40-1.60 (m, 13 H). |
| 38 | (5-substituted 1H-indazole-3-C(O)NH-CH$_2$CF$_3$) | $^1$H NMR (400 MHz, CD$_3$OD, δ): 8.31 (s, 1 H), 7.74 (s, 1 H), 7.68 (d, J = 8.8 Hz, 1 H), 7.50 (d, J = 8.8 Hz, 1 H), 4.10-4.17 (m, 2 H), 3.65-4.00 (m, 2 H), 3.40-3.65 (m, 2 H), 2.90 (s, 2 H), 2.67 (s, 2 H), 1.50-1.80 (m, 4 H), 1.60 (s, 9 H). |
| 39 | (5-substituted 2-methylamino-1H-benzimidazole) | $^1$H NMR (400 MHz, CD$_3$OD, δ): 8.30 (s, 1 H), 7.73 (s, 1 H), 7.31 (d, J = 9.6 Hz, 2 H), 7.18-7.20 (m, 1 H), 3.40-3.95 (m, 4 H), 3.04 (s, 3 H), 2.88 (s, 2 H), 2.65 (s, 2 H), 1.60 (s, 9 H), 1.45-1.80 (m, 4 H). |
| 40 | (7-substituted 2-methylamino-quinoline) | +ESI (M + H) 446.3; HPLC retention time 2.07 minutes (Method A). |
| 41 | (6-substituted 3-cyano-1H-indazole) | +ESI (M + H) 431.2; $^1$H NMR (400 MHz, CD$_3$OD, δ): 7.93 (d, 1 H), 7.74 (d, 2 H), 7.40 (dd, 1 H), 3.70-4.00 (m, 2 H), 3.40-3.50 (m, 2 H), 2.89 (s, 2 H), 2.66 (s, 2 H), 1.65-1.80 (m, 2 H), 1.60 (s, 9 H), 1.50-1.65 (m, 2 H). |

TABLE 3-continued

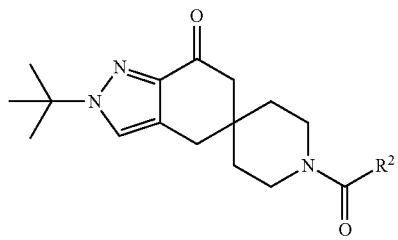

| Example | —R2 | Analytical Data |
|---|---|---|
| 42 | [3-chloro-1H-pyrrolo[3,2-b]pyridin-6-yl] | +ESI (M + H) 440.1; HPLC retention time 2.06 minutes (Method A). |
| 43 | [3-cyano-1H-indazol-5-yl] | +ESI (M + H) 431.3; ¹H NMR (400 MHz, DMSO-$d_6$, δ): 7.89-7.92 (m, 1 H), 7.83 (s, 1 H), 7.81 (dd, J = 8.61, 0.78 Hz, 1 H), 7.54 (dd, J = 8.71, 1.47 Hz, 1 H), 3.36-3.78 (m, 4 H), 2.79 (s, 2 H), 2.58 (s, 2 H), 1.53 (s, 9 H), 1.41-1.52 (m, 4 H). |
| 44 | [6-carbamoylquinolin-3-yl] | +ESI (M + H) 460.2; ¹H NMR (400 MHz, DMSO-$d_6$, δ): 8.94 (d, J = 2.1 Hz, 1 H), 8.56 (d, J = 2.0 Hz, 1 H), 8.47 (d, J = 2.1 Hz, 1 H), 8.18-8.24 (m, 2 H), 8.07 (d, J = 8.78 Hz), 7.81 (s, 1 H), 7.57 (s, 1 H), 3.57-3.77 (m, 2 H), 3.33-3.44 (m, 2 H), 2.77 (s, 2 H), 2.56 (s, 2 H), 1.53-1.61 (m, 2 H), 1.50 (s, 9 H), 1.45-1.50 (m, 2 H). |

Example 45

6-[(2-tert-butyl-7-oxo-2,4,6,7-tetrahydro-1'H-spiro[indazole-5,4'-piperidin]-1'-yl) carbonyl]-1H-pyrrolo[3,2-b]pyridine-3-carboxamide

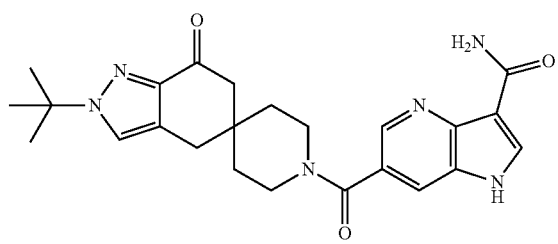 [SMILES: CC(C)(C)n1cc2c(n1)C(=O)CC1(CCN(C(=O)c3cnc4c(C(N)=O)c[nH]c4c3)CC1)C2]

Step 1. methyl 3-bromo-1H-pyrrolo[3,2-b]pyridine-6-carboxylate

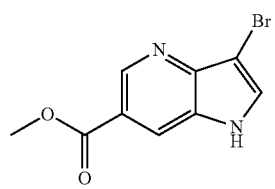

The title compound was prepared by a method analogous to that described in Step 2 for Intermediate 9, using methyl 1H-pyrrolo[3,2-b]pyridine-6-carboxylate. +ESI (M+H)

257.1; ¹H NMR (DMSO-d₆, δ): 12.08 (br. s., 1 H), 8.92 (d, J=1.8 Hz, 1 H), 8.30 (d, J=2.0 Hz, 1 H), 8.10 (d, J=2.9 Hz, 1 H), 3.88 (s, 3 H).

Step 2.
3-bromo-1H-pyrrolo[3,2-b]pyridine-6-carboxylic acid hydrochloride

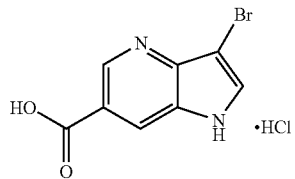 [SMILES: O=C(O)c1cnc2c(Br)c[nH]c2c1 ; Cl]

To a solution of methyl 3-bromo-1H-pyrrolo[3,2-b]pyridine-6-carboxylate (2.90 g, 11.4 mmol) in 1,4-dioxane (30 mL) was added 6 N aqueous hydrochloric acid (18.9 mL, 114 mmol). The reaction was heated to 90° C. and stirred overnight. The reaction was cooled to room temperature and concentrated to dryness to afford the title compound (2.76 g, quantitative). ¹H NMR (400 MHz, DMSO-d₆, δ): 12.31 (br. s., 1 H), 8.91 (d, J=1.8 Hz, 1 H), 8.37 (s, 1 H), 8.14 (d, J=1.6 Hz, 1 H).

Step 3. 1'-(3-bromo-1H-pyrrolo[3,2-b]pyridine-6-carbonyl)-2-tert-butyl-4,6-dihydrospiro[indazole-5,4'-piperidin]-7(2H)-one

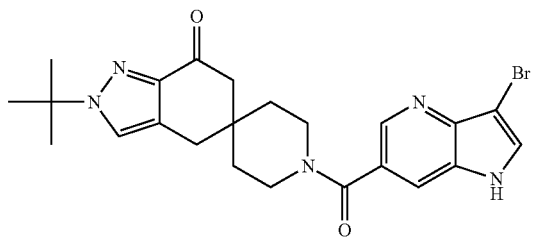 [SMILES: CC(C)(C)n1cc2c(n1)C(=O)CC1(CCN(C(=O)c3cnc4c(Br)c[nH]c4c3)CC1)C2]

To a suspension of 3-bromo-1H-pyrrolo[3,2-b]pyridine-6-carboxylic acid hydrochloride (2.75 g, 9.91 mmol) and 2-tert-butyl-4,6-dihydrospiro[indazole-5,4'-piperidin]-7(2H)-one hydrochloride salt (2.95 g, 9.91 mmol) in dichloromethane (30 mL) was added triethylamine (5.52 mL, 39.6 mmol). N,N-dimethylformamide (5 mL) was then added, followed by 1-hydroxybenzotriazole (1.61 g, 11.9 mmol) and 1, (3-dimethylaminopropyl)-3-ethyl carbodiimide hydrochloride (2.28 g, 11.9 mmol). The reaction was allowed to stir at room temperature for 60 hours. The reaction was diluted with ethyl acetate and washed with saturated aqueous sodium bicarbonate and brine. The organics were dried over magnesium sulfate, filtered, and concentrated. Purification by flash column chromatography (0-10% methanol/ethyl acetate) gave the title compound (3.39 g, 71%) as a pale brown solid. +ESI (M+1+H) 486.2; ¹H NMR (400 MHz, CDCl₃, δ): 10.05 (br. s., 1 H), 8.57 (d, J=1.8 Hz, 1 H), 7.87 (d, J=1.8 Hz, 1 H), 7.61 (d, J=2.7 Hz, 1 H), 7.44 (s, 1 H), 3.78 (br. s., 2 H), 3.51 (br. s., 2 H), 2.81 (s, 2 H), 2.65 (s, 2 H), 1.63 (s, 13 H).

Step 4. 6-[(2-tert-butyl-7-oxo-2,4,6,7-tetrahydro-1'H-spiro[indazole-5,4'-piperidin]-1'-yl)carbonyl]-1H-pyrrolo[3,2-b]pyridine-3-carboxamide A round bottom flask was charged with 1'-(3-bromo-1H-pyrrolo[3,2-b]pyridine-6-carbonyl)-2-tert-butyl-4,6-dihydrospiro[indazole-5,4'-piperidin]-7(2H)-one (1.25 g, 2.58 mmol), zinc cyanide (454 mg, 3.87 mmol), zinc dust (169 mg, 2.58 mmol), and lastly dimethylacetamide (22 mL). Nitrogen was bubbled through the mixture for 5 minutes. Copper (I) iodide (494 mg, 2.58 mmol) and [1,1'-bis(diphenylphosphino)ferrocene]dichloropalladium(II), complex with dichloromethane (189 mg, 0.258 mmol) were added and the reaction was heated to 120° C. overnight. The reaction mixture was diluted with ethyl acetate and filtered through Celite. The filtrate was washed with sodium bicarbonate (7% aqueous) and brine. The organics were dried over magnesium sulfate, filtered, and concentrated. The crude residue was triturated with methyl tert-butyl ether and the resulting orange powder was filtered off and dried.

The powder (550 mg) was suspended in dichloromethane (20 mL) and concentrated sulfuric acid (1 mL) was added. The reaction was stirred vigorously for 3 hours, then the upper dichloromethane layer was decanted and set aside. To the remaining brown syrup was added 50 g ice and the pH was adjusted to 7 using 5 N aqueous sodium hydroxide. The mixture was combined with the previously separated dichloromethane layer and transferred to a separatory funnel. The phases were separated and the aqueous layer was extracted twice with dichloromethane. The combined organics were washed with brine, dried over magnesium sulfate, filtered, and concentrated. Purification by flash column chromatography (0-10% methanol/dichloromethane) gave the title compound (420 mg, 73%) as an off-white solid. +ESI (M+H) 449.3; ¹H NMR (400 MHz, DMSO-d₆, δ): 12.09 (br. s., 1 H), 8.49 (d, J=1.8 Hz, 1 H), 8.24 (s, 1 H), 8.12 (br. s., 1 H), 7.93 (d, J=1.8 Hz, 1 H), 7.83 (s, 1 H), 7.39 (d, J=2.7 Hz, 1 H), 3.62 (br. s., 2 H), 3.43 (br. s., 2 H), 2.79 (s, 2 H), 2.58 (s, 2 H), 1.53 (s, 13 H).

Example 46

2-({3-[(2-tert-butyl-7-oxo-2,4,6,7-tetrahydro-1'H-spiro[indazole-5,4'-piperidin]-1'-yl)carbonyl]quinolin-6-yl}oxy)acetamide

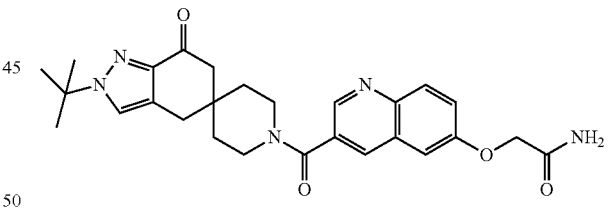

Step 1: tert-butyl 2-(3-(2-tert-butyl-7-oxo-2,4,6,7-tetrahydrospiro[indazole-5,4'-piperidine]-1'-ylcarbonyl)quinolin-6-yloxy)acetate

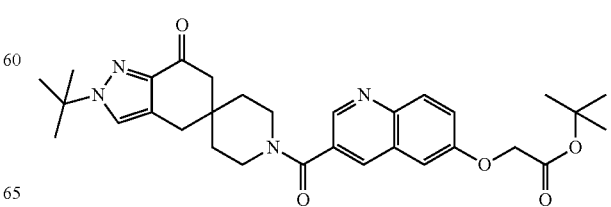

The title compound was prepared by a method analogous to that described for Example 3, using 6-(2-tert-butoxy-2-oxo-ethoxy)quinoline-3-carboxylic acid and 2-tert-butyl-4,6-dihydrospiro[indazole-5,4'-piperidin]-7(2H)-one hydrochloride salt. +ESI (M+H) 547.3; $^1$H NMR (400 MHz, CDCl$_3$, δ): 8.77 (d, J=2.0 Hz, 1 H), 8.10 (d, J=1.6 Hz, 1 H), 8.06 (d, J=9.2 Hz, 1 H), 7.50 (dd, J=9.3, 2.8 Hz, 1 H), 7.41 (s, 1 H), 7.02 (d, J=2.7 Hz, 1 H), 4.64 (s, 2 H), 3.68-3.93 (m, 2 H), 3.41-3.51 (m, 2 H), 2.78 (s, 2 H), 2.65 (s, 2 H), 1.53-1.76 (m, 4 H), 1.61 (s, 9 H), 1.49 (s, 9 H).

Step 2: 2-(3-(2-tert-butyl-7-oxo-2,4,6,7-tetrahydrospiro[indazole-5,4'-piperidine]-1'-ylcarbonyl)quinolin-6-yloxy)acetic acid

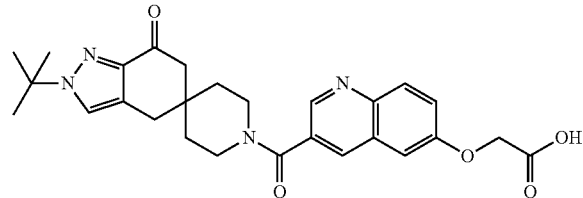 [SMILES: CC(C)(C)n1cc2c(n1)C(=O)CC1(CCN(C(=O)c3cnc4ccc(OCC(=O)O)cc4c3)CC1)C2]

Hydrochloric acid (10 mL, 40 mmol, 4 M in 1,4-dioxane) was added to tert-butyl 2-(3-(2-tert-butyl-7-oxo-2,4,6,7-tetrahydrospiro[indazole-5,4'-piperidine]-1'-ylcarbonyl)quinolin-6-yloxy)acetate (470 mg, 0.860 mmol). The reaction was stirred vigorously at room temperature for 1 hour. The reaction was concentrated. The residue was coevaporated with ethyl acetate and heptanes several times, and then dried under vacuum to provide the title compound (422 mg, 100%). +ESI (M+H) 491.4; $^1$H NMR (400 MHz, DMSO-d$_6$, δ): 8.76 (d, J=2.0 Hz, 1 H), 8.35 (d, J=1.4 Hz, 1 H), 7.98 (d, J=9.2 Hz, 1 H), 7.81 (s, 1 H), 7.52 (dd, J=9.3, 2.8 Hz, 1 H), 7.42 (d, J=2.9 Hz, 1 H), 4.82 (s, 2 H), 3.57-3.73 (m, 2H), 3.34-3.50 (m, 2 H), 2.77 (s, 2 H), 2.56 (s, 2 H), 1.50 (s, 9 H), 1.44-1.58 (m, 4 H).

Step 3: 2-({3-[(2-tert-butyl-7-oxo-2,4,6,7-tetrahydro-1'H-spiro[indazole-5,4'-piperidin]-1'-yl)carbonyl]quinolin-6-yl}oxy)acetamide To a suspension of 2-(3-(2-tert-butyl-7-oxo-2,4,6,7-tetrahydrospiro[indazole-5,4'-piperidine]-1'-ylcarbonyl)quinolin-6-yloxy)acetic acid (290 mg, 0.59 mmol) in dichloromethane (6 mL) was added ammonia (2.36 mL, 1.18 mmol, 0.5 M in 1,4-dioxane) and (1H-7-azabenzotriazol-1-yl)-1,1,3,3-tetramethyl uronium hexafluorophosphate (225 mg, 0.591 mmol). The reaction was stirred at room temperature overnight. The reaction was concentrated and purified by flash column chromatography (0-10% methanol/dichloromethane). The resulting material was dissolved in ethyl acetate, washed with water and brine, dried over magnesium sulfate, filtered, and concentrated to give the title compound (280 mg, 97%). +ESI (M+H) 490.4; $^1$H NMR (400 MHz, CDCl$_3$, δ): 8.81 (d, J=2.1 Hz, 1 H), 8.11 (d, J=2.1 Hz, 1 H), 8.06 (d, J=9.2 Hz, 1 H), 7.46 (dd, J=9.3, 2.8 Hz, 1 H), 7.41 (s, 1 H), 7.11 (d, J=2.7 Hz, 1 H), 6.54 (br. s., 1 H), 5.66 (br. s., 1 H), 4.63 (s, 2 H), 3.68-3.96 (m, 2 H), 3.41-3.51 (m, 2 H), 2.78 (s, 2 H), 2.65 (s, 2 H), 1.66-1.76 (m, 2 H), 1.61 (s, 9 H), 1.50-1.60 (m, 2 H).

Example 47

1'-[(2-aminoquinolin-7-yl)carbonyl]-2-tert-butyl-2,4-dihydrospiro[indazole-5,4'-piperidin]-7(6H)-one

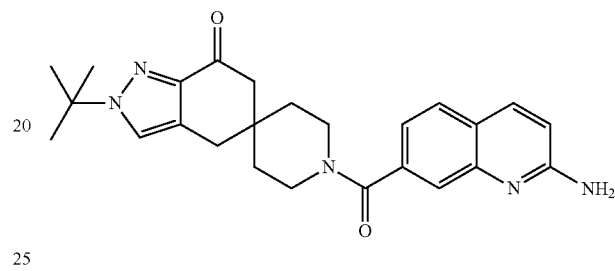

The title compound was prepared by a method analogous to that described for Example 25, using 2-tert-butyl-4,6-dihydrospiro[indazole-5,4'-piperidin]-7(2H)-one hydrochloride salt. +ESI (M+H) 432.3; $^1$H NMR (400 MHz, CDCl$_3$, δ): 8.10 (d, J=9.21 Hz, 1 H), 7.82 (s, 1 H), 7.76 (dd, J=7.95 Hz, 1 H), 7.49 (dd, 1 H), 7.43 (s, 1 H), 6.87 (d, J=9.33 Hz, 1 H), 3.95 (m, 1 H), 3.64 (m, 1 H), 3.26-3.46 (m, 2 H), 2.79 (s, 2 H), 2.66 (s, 2 H), 1.57-1.80 (m, 4 H), 1.61 (s, 9 H).

Example 48

2-bicyclo[1.1.1]pent-1-yl-1'-(1H-indazol-5-ylcarbonyl)-2,4-dihydrospiro[indazole-5,4'-piperidin]-7(6H)-one

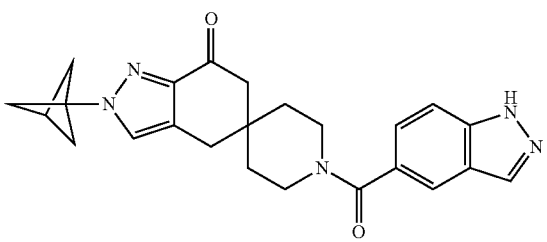 [SMILES: O=C1CC2(CCN(C(=O)c3ccc4[nH]ncc4c3)CC2)Cc2cn(C34CC(C3)C4)nc21]

The title compound was prepared by a method analogous to that described in Example 1, using 2-(bicyclo[1.1.1]pentan-1-yl)-4,6-dihydrospiro[indazole-5,4'-piperidin]-7(2H)-one and 1H-indazole-5-carboxylic acid. +ESI (M+H) 416.2; HPLC retention time 2.32 minutes (Method A).

Example 49

5-[(1-bicyclo[1.1.1]pent-1-yl-7-oxo-1,4,6,7-tetrahydro-1'H-spiro[indazole-5,4'-piperidin]-1'-yl)carbonyl]-1H-indazole-3-carboxamide

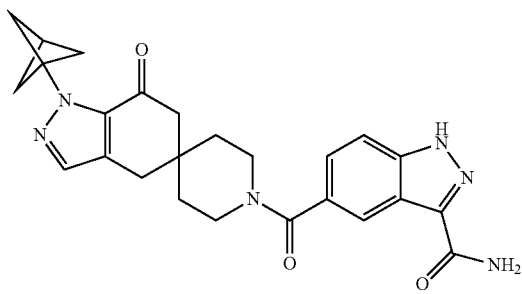 [SMILES: NC(=O)c1n[nH]c2ccc(C(=O)N3CCC4(CC3)CC(=O)c3c(cnn3C35CC(C3)C5)C4)cc12]

The title compound was prepared by a method analogous to that described for Example 2, using 1-(bicyclo[1.1.1]pentan-1-yl)-4,6-dihydrospiro[indazole-5,4'-piperidin]-7(1H)-one hydrochloride and 3-carbamoyl-1H-indazole-5-carboxylic acid. +APCI (M+H) 459.5; $^1$H NMR (400 MHz, CDCl$_3$, δ): 8.42 (s, 1 H), 7.50 (s, 2 H), 7.35 (s, 1 H), 6.93 (br. s., 1 H), 5.47 (br. s., 1 H), 3.32-3.93 (m, 4 H), 2.79 (s, 2 H), 2.58 (s, 2 H), 2.56 (s, 1 H), 2.39 (s, 6 H), 1.45-1.76 (m, 4 H).

The following compounds shown in Table 4 can be prepared in a manner analogous to the foregoing examples.

TABLE 4

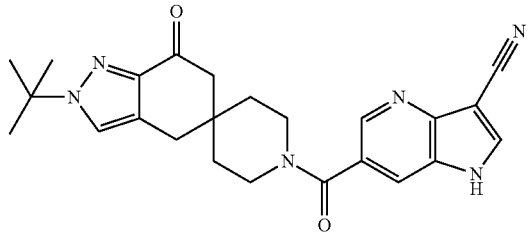 [SMILES: CC(C)(C)n1cc2c(n1)C(=O)CC1(CCN(C(=O)c3cnc4c(C#N)c[nH]c4c3)CC1)C2]

Example 50: 6-[(2-tert-butyl-7-oxo-2,4,6,7-tetrahydro-1'H-spiro[indazole-5,4'-piperidin]-1'-yl)carbonyl]-1H-pyrrolo[3,2-b]pyridine-3-carbonitrile

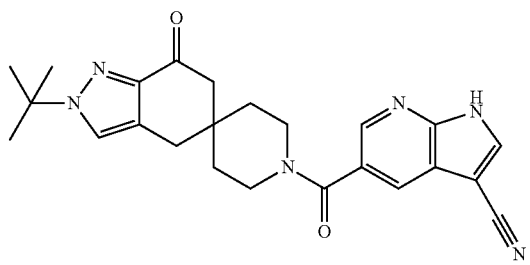 [SMILES: CC(C)(C)n1cc2c(n1)C(=O)CC1(CCN(C(=O)c3cnc4[nH]cc(C#N)c4c3)CC1)C2]

Example 51: 5-[(2-tert-butyl-7-oxo-2,4,6,7-tetrahydro-1'H-spiro[indazole-5,4'-piperidin]-1'-yl)carbonyl]-1H-pyrrolo[2,3-b]pyridine-3-carbonitrile

TABLE 4-continued

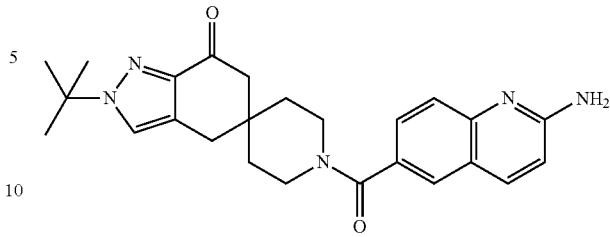

Example 52: 1'-[(2-aminoquinolin-6-yl)carbonyl]-2-tert-butyl-2,4-dihydrospiro[indazole-5,4'-piperidin]-7(6H)-one

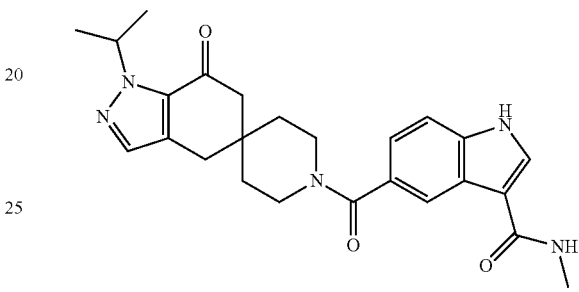

Example 53: 5-[(1-isopropyl-7-oxo-1,4,6,7-tetrahydro-1'H-spiro[indazole-5,4'-piperidin]-1'-yl)carbonyl]-N-methyl-1H-indole-3-carboxamide

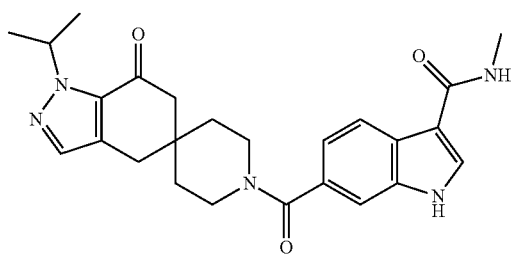 [SMILES: CNC(=O)c1c[nH]c2cc(C(=O)N3CCC4(CC3)CC(=O)c3c(cnn3C(C)C)C4)ccc12]

Example 54: 6-[(1-isopropyl-7-oxo-1,4,6,7-tetrahydro-1'H-spiro[indazole-5,4'-piperidin]-1'-yl)carbonyl]-N-methyl-1H-indole-3-carboxamide

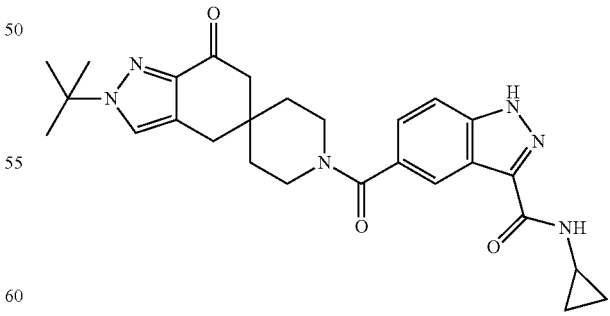

Example 55: 5-[(2-tert-butyl-7-oxo-2,4,6,7-tetrahydro-1'H-spiro[indazole-5,4'-piperidin]-1'-yl)carbonyl]-N-cyclopropyl-1H-indazole-3-carboxamide TABLE 4-continued

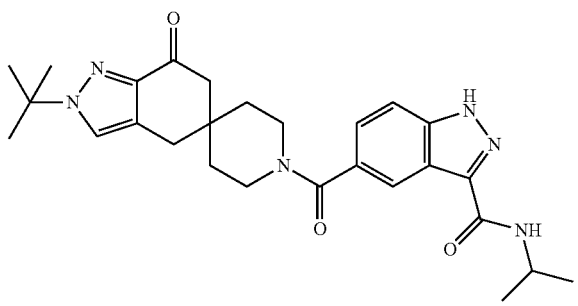 [SMILES: CC(C)NC(=O)c1n[nH]c2ccc(C(=O)N3CCC4(CC3)CC(=O)c3nn(C(C)(C)C)cc3C4)cc12]

Example 56: 5-[(2-tert-butyl-7-oxo-2,4,6,7-tetrahydro-1'H-spiro[indazole-5,4'-piperidin]-1'-yl)carbonyl]-N-isopropyl-1H-indazole-3-carboxamide

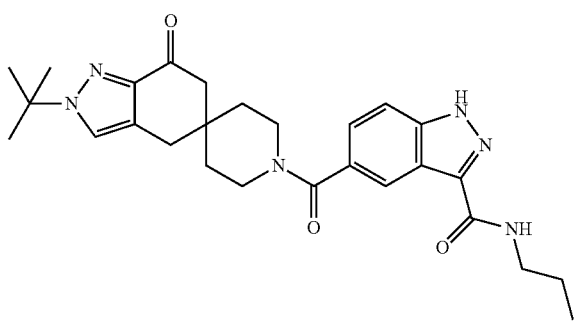 [SMILES: CCCNC(=O)c1n[nH]c2ccc(C(=O)N3CCC4(CC3)CC(=O)c3nn(C(C)(C)C)cc3C4)cc12]

Example 57: 5-[(2-tert-butyl-7-oxo-2,4,6,7-tetrahydro-1'H-spiro[indazole-5,4'-piperidin]-1'-yl)carbonyl]-N-propyl-1H-indazole-3-carboxamide

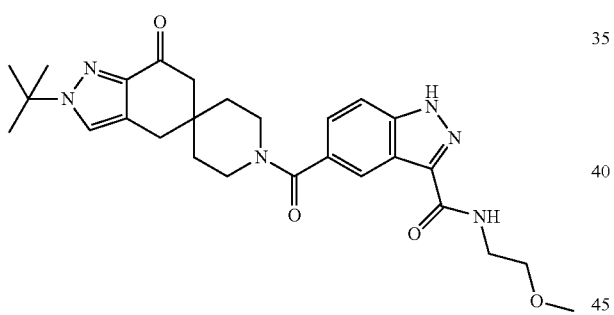

Example 58: 5-[(2-tert-butyl-7-oxo-2,4,6,7-tetrahydro-1'H-spiro[indazole-5,4'-piperidin]-1'-yl)carbonyl]-N-(2-methoxyethyl)-1H-indazole-3-carboxamide

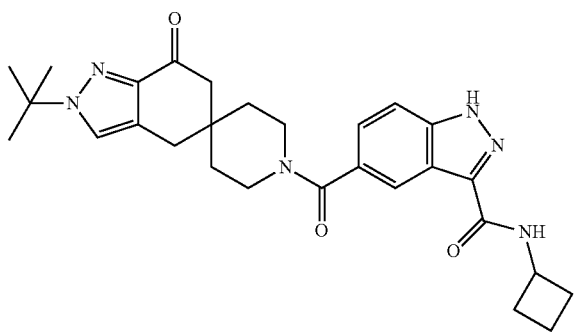 [SMILES: CC(C)(C)n1cc2c(n1)C(=O)CC1(CCN(C(=O)c3ccc4[nH]nc(C(=O)NC5CCC5)c4c3)CC1)C2]

Example 59: 5-[(2-tert-butyl-7-oxo-2,4,6,7-tetrahydro-1'H-spiro[indazole-5,4'-piperidin]-1'-yl)carbonyl]-N-cyclobutyl-1H-indazole-3-carboxamide TABLE 4-continued

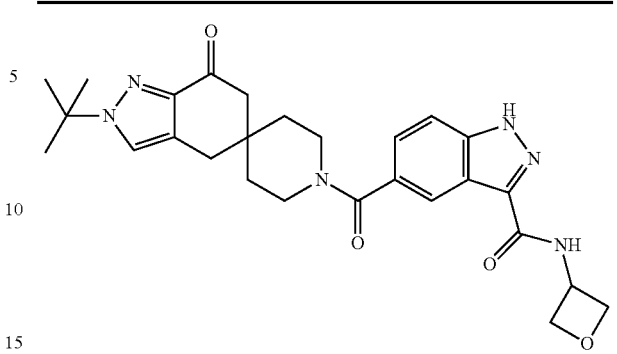

Example 60: 5-[(2-tert-butyl-7-oxo-2,4,6,7-tetrahydro-1'H-spiro[indazole-5,4'-piperidin]-1'-yl)carbonyl]-N-oxetan-3-yl-1H-indazole-3-carboxamide

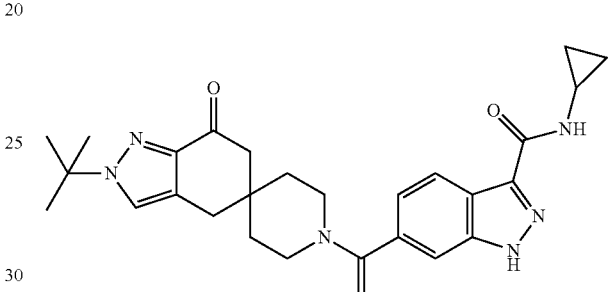

Example 61: 6-[(2-tert-butyl-7-oxo-2,4,6,7-tetrahydro-1'H-spiro[indazole-5,4'-piperidin]-1'-yl)carbonyl]-N-cyclopropyl-1H-indazole-3-carboxamide

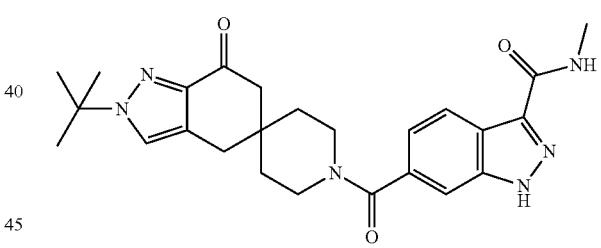

Example 62: 6-[(2-tert-butyl-7-oxo-2,4,6,7-tetrahydro-1'H-spiro[indazole-5,4'-piperidin]-1'-yl)carbonyl]-N-methyl-1H-indazole-3-carboxamide

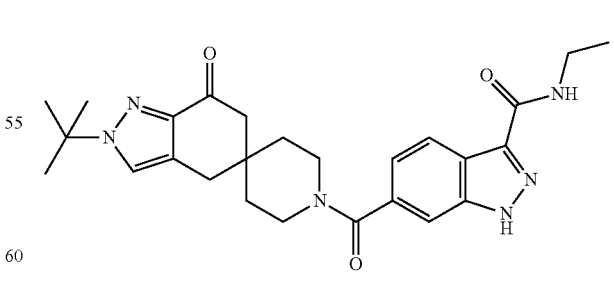

Example 63: 6-[(2-tert-butyl-7-oxo-2,4,6,7-tetrahydro-1'H-spiro[indazole-5,4'-piperidin]-1'-yl)carbonyl]-N-ethyl-1H-indazole-3-carboxamide TABLE 4-continued

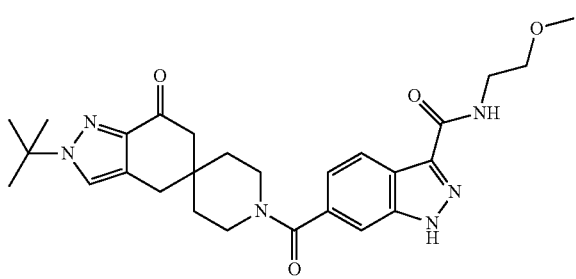 [SMILES: COCCNC(=O)c1n[nH]c2cc(C(=O)N3CCC4(CC3)CC(=O)c3nn(C(C)(C)C)cc3C4)ccc12]

Example 64: 6-[(2-tert-butyl-7-oxo-2,4,6,7-tetrahydro-1'H-spiro[indazole-5,4'-piperidin]-1'-yl)carbonyl]-N-(2-methoxyethyl)-1H-indazole-3-carboxamide

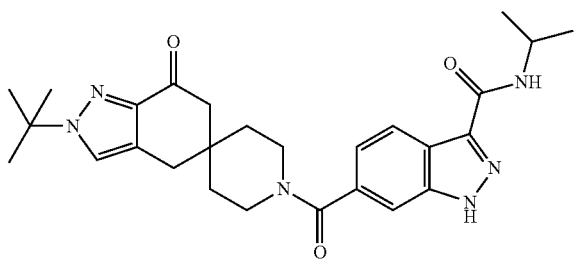 [SMILES: CC(C)NC(=O)c1n[nH]c2cc(C(=O)N3CCC4(CC3)CC(=O)c3nn(C(C)(C)C)cc3C4)ccc12]

Example 65: 6-[(2-tert-butyl-7-oxo-2,4,6,7-tetrahydro-1'H-spiro[indazole-5,4'-piperidin]-1'-yl)carbonyl]-N-isopropyl-1H-indazole-3-carboxamide

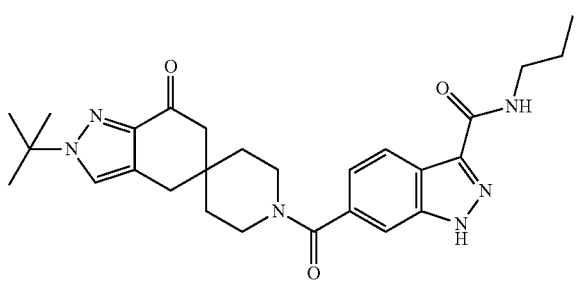 [SMILES: CCCNC(=O)c1n[nH]c2cc(C(=O)N3CCC4(CC3)CC(=O)c3nn(C(C)(C)C)cc3C4)ccc12]

Example 66: 6-[(2-tert-butyl-7-oxo-2,4,6,7-tetrahydro-1'H-spiro[indazole-5,4'-piperidin]-1'-yl)carbonyl]-N-propyl-1H-indazole-3-carboxamide

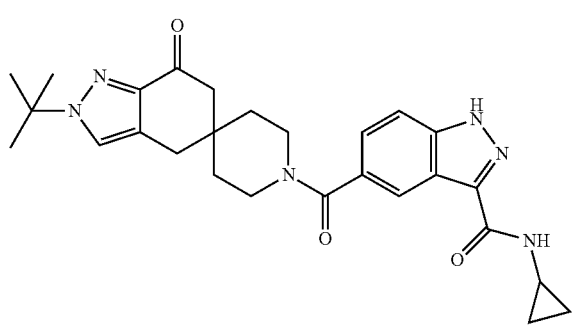 [SMILES: CC(C)(C)n1cc2c(n1)C(=O)CC1(CCN(C(=O)c3ccc4[nH]nc(C(=O)NC5CC5)c4c3)CC1)C2]

Example 67: 5-[(2-tert-butyl-7-oxo-2,4,6,7-tetrahydro-1'H-spiro[indazole-5,4'-piperidin]-1'-yl)carbonyl]-N-cyclopropyl-1H-indole-3-carboxamide TABLE 4-continued

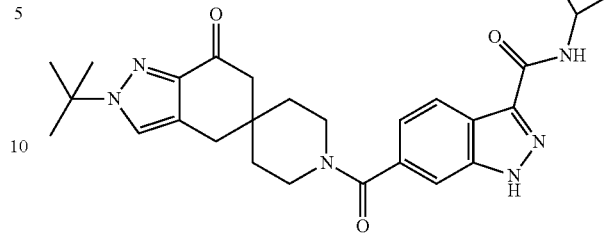

Example 68: 6-[(2-tert-butyl-7-oxo-2,4,6,7-tetrahydro-1'H-spiro[indazole-5,4'-piperidin]-1'-yl)carbonyl]-N-cyclobutyl-1H-indazole-3-carboxamide

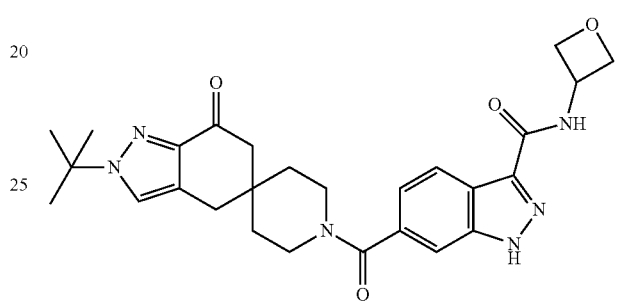

Example 69: 6-[(2-tert-butyl-7-oxo-2,4,6,7-tetrahydro-1'H-spiro[indazole-5,4'-piperidin]-1'-yl)carbonyl]-N-oxetan-3-yl-1H-indazole-3-carboxamide

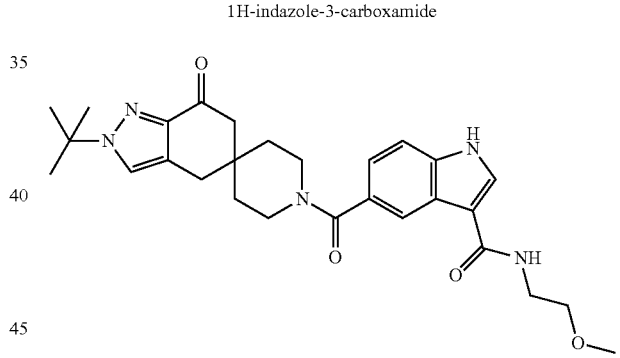

Example 70: 5-[(2-tert-butyl-7-oxo-2,4,6,7-tetrahydro-1'H-spiro[indazole-5,4'-piperidin]-1'-yl)carbonyl]-N-(2-methoxyethyl)-1H-indole-3-carboxamide

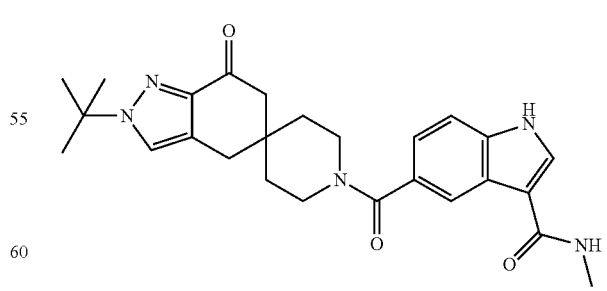

Example 71: 5-[(2-tert-butyl-7-oxo-2,4,6,7-tetrahydro-1'H-spiro[indazole-5,4'-piperidin]-1'-yl)carbonyl]-N-methyl-1H-indole-3-carboxamide

TABLE 4-continued

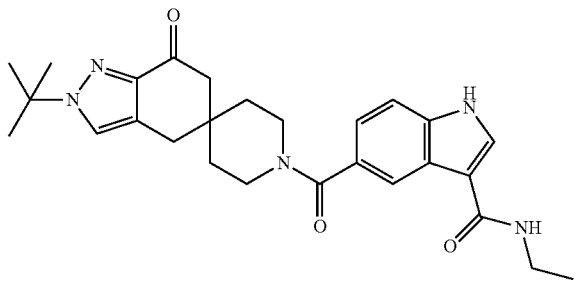 [SMILES: CCNC(=O)c1c[nH]c2ccc(C(=O)N3CCC4(CC3)CC(=O)c3nn(C(C)(C)C)cc3C4)cc12]

Example 72: 5-[(2-tert-butyl-7-oxo-2,4,6,7-tetrahydro-1'H-spiro[indazole-5,4'-piperidin]-1'-yl)carbonyl]-N-ethyl-1H-indole-3-carboxamide

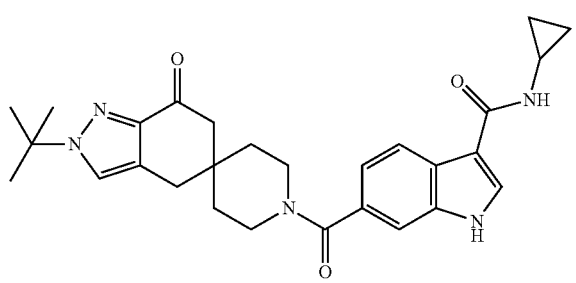 [SMILES: CC(C)(C)n1cc2c(n1)C(=O)CC1(CCN(C(=O)c3ccc4c(C(=O)NC5CC5)c[nH]c4c3)CC1)C2]

Example 73: 6-[(2-tert-butyl-7-oxo-2,4,6,7-tetrahydro-1'H-spiro[indazole-5,4'-piperidin]-1'-yl)carbonyl]-N-cyclopropyl-1H-indole-3-carboxamide Pharmacological Data Biological Protocols The utility of the compounds of present invention, in the treatment of diseases (such as are detailed herein) in animals, particularly mammals (e.g., humans) may be demonstrated by the activity thereof in conventional assays known to one of ordinary skill in the art, including the in vitro and in vivo assays described below. Such assays also provide a means whereby the activities of the compound of the present invention can be compared with the activities of other known compounds.

Direct Inhibition of the Activities of ACC1 and ACC2

The ACC inhibitory activity of the compound of the present invention was demonstrated by methods based on standard procedures. For example direct inhibition of ACC activity, for the compound of Formula (I) was determined using preparations of recombinant human ACC1 (rhACC1) and recombinant human ACC2 (rhACC2). Representative sequences of the recombinant human ACC1 and ACC2 that can be used in the assay are provided herein as SEQ ID NO. 1 and SEQ. ID NO. 2, respectively.

[1] Preparation of rhACC1. Two liters of SF9 cells, infected with recombinant baculovirus containing full length human ACC1 cDNA, were suspended in ice-cold lysis buffer (25 mM Tris, pH 7.5; 150 mM NaCl; 10% glycerol; 5 mM imidazole (EMD Bioscience; Gibbstown, N.J.); 2 mM TCEP (BioVectra; Charlottetown, Canada); Benzonase nuclease (10000 U/100 g cell paste; Novagen; Madison, Wis.); EDTA-free protease inhibitor cocktail (1 tab/50 mL; Roche Diagnostics; Mannheim, Germany). Cells were lysed by 3 cycles of freeze-thaw and centrifuged at 40,000×g for 40 minutes (4° C.). Supernatant was directly loaded onto a HisTrap FF crude column (GE Healthcare; Piscataway, N.J.) and eluted with an imidazole gradient up to 0.5 M over 20 column volumes (CV). ACC1-containing fractions were pooled and diluted 1:5 with 25 mM Tris, pH 7.5, 2 mM TCEP, 10% glycerol and direct loaded onto a CaptoQ (GE Healthcare) column and eluted with an NaCl gradient up to 1 M over 20 CV's. Phosphate groups were removed from purified ACC1 by incubation with lambda phosphatase (100 U/10 µM target protein; New England Biolabs; Beverly, Mass.) for 14 hours at 4° C.; okadaic acid was added (1 µM final concentration; Roche Diagnostics) to inhibit the phosphatase. Purified ACC1 was exchanged into 25 mM Tris, pH 7.5, 2 mM TCEP, 10% glycerol, 0.5 M NaCl by 6 hour dialysis at 4° C. Aliquots were prepared and frozen at −80° C.

[2] Measurement of rhACC1 inhibition. hACC1 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 µM ATP reaction. The final conditions for the assay were 50 mM HEPES, pH 7.2, 10 mM $MgCl_2$, 7.5 mM tripotassium citrate, 2 mM DTT, 0.1 mg/mL BSA, 30 µM acetyl-CoA, 50 µM ATP, and 10 mM $KHCO_3$ Typically, a 10 µl reaction was run for 120 min at 25° C., and 10 µl of Transcreener stop and detect buffer was added and the combination incubated at room temp for an additional 1 hour. The data was acquired on a Envision Fluorescence reader (Perkinelmer) using a 620 excitation Cy5 FP general dual mirror, 620 excitation Cy5 FP filter, 688 emission (S) and a 688 (P) emission filter.

[3] Preparation of rhACC2. Human ACC2 inhibition was measured using purified recombinant human ACC2 (hrACC2). Briefly, a full length Cytomax clone of ACC2 was purchased from Cambridge Bioscience Limited and was sequenced and subcloned into PcDNA5 FRT TO-TOPO (Invitrogen, Carlsbad, Calif.). The ACC2 was expressed in CHO cells by tetracycline induction and harvested in 5 liters of DMEM/F12 with glutamine, biotin, hygromycin and blasticidin with 1 µg/mL tetracycline (Invitrogen, Carlsbad, Calif.). The conditioned medium containing ACC2 was then applied to a Softlink Soft Release Avidin column (Promega, Madison, Wis.) and eluted with 5 mM biotin. 4 mgs of ACC2 were eluted at a concentration of 0.05 mg/mL (determined by A280) with an estimated purity of 95% (determined by A280). The purified ACC2 was dialyzed in 50 mM Tris, 200 mM NaCl, 4 mM DTT, 2 mM EDTA, and 5% glycerol. The pooled protein was frozen and stored at −80° C., with no loss of activity upon thawing. For measurement of ACC2 activity and assessment of ACC2 inhibition, test compounds were dissolved in DMSO and added to the rhACC2 enzyme as a 5× stock with a final DMSO concentration of 1%.

[4] Measurement of human ACC2 inhibition. hACC2 was assayed in a Costar #3676 (Costar, Cambridge, Mass.) 384-well plate using the Transcreener ADP detection FP assay kit (Bellbrook Labs, Madison, Wis.) using the manufacturer's recommended conditions for a 50 uM ATP reaction. The final conditions for the assay were 50 mM HEPES, pH 7.2, 5 mM $MgCl_2$, 5 mM tripotassium citrate, 2 mM DTT, 0.1 mg/mL BSA, 30 µM acetyl-CoA, 50 µM ATP, and 8 mM $KHCO_3$. Typically, a 10 µl reaction was run for 50 min at 25° C., and 10 µl of Transcreener stop and detect buffer was added and the combination incubated at room temp for an additional 1 hour. The data was acquired on an Envision Fluorescence reader (Perkinelmer) using a 620 excitation Cy5 FP general dual mirror, 620 excitation Cy5 FP filter, 688 emission (S) and a 688 (P) emission filter.

The results using the recombinant hACC1 and recombinant hACC2 Transcreener assays described above are summarized in the table below for the Compounds of Formula (I) exemplified in the Examples above.

| Example | hACC1 IC50 (nM) | n | hACC2 IC50 (nM) | n |
|---|---|---|---|---|
| 1 | 6.0 | 6 | 1.4 | 6 |
| 2 | 7.9 | 12 | 3.1 | 12 |
| 3 | 32 | 6 | 13 | 6 |
| 4 | 6.5 | 7 | 2.9 | 7 |
| 5 | 17 | 4 | 5.8 | 4 |
| 6 | 11 | 4 | 2.9 | 4 |
| 7 | 5.6 | 4 | 1.6 | 4 |
| 8 | 17 | 3 | 3.3 | 3 |
| 9 | 8.4 | 3 | 2.9 | 3 |
| 10 | 6.1 | 3 | 2.7 | 3 |
| 11 | 14 | 3 | 5.5 | 3 |
| 12 | 13 | 5 | 3.0 | 5 |
| 13 | 2.4 | 3 | 1.5 | 3 |
| 14 | 5.0 | 5 | 2.1 | 5 |
| 15 | 14 | 3 | 2.6 | 3 |
| 16 | 6.7 | 3 | 3.1 | 3 |
| 17 | 19 | 3 | 11 | 3 |
| 18 | 33 | 3 | 22 | 3 |
| 19 | 63 | 3 | 15 | 3 |
| 20 | 13 | 4 | 3.0 | 4 |
| 21 | 47 | 4 | 6.7 | 4 |
| 22 | 30 | 3 | 6.9 | 3 |
| 23 | 32 | 3 | 15 | 3 |
| 24 | 43 | 1 | 20 | 1 |
| 25 | 12 | 2 | 10 | 1 |
| 26 | 7.4 | 3 | 2.1 | 3 |
| 27 | 5.5 | 3 | 3.5 | 3 |
| 28 | 6.5 | 5 | 1.3 | 5 |
| 29 | 8.6 | 6 | 1.7 | 7 |
| 30 | 9.4 | 4 | 2.6 | 4 |
| 31 | 3.8 | 4 | 1.3 | 4 |
| 32 | 8.1 | 4 | 1.5 | 4 |
| 33 | 3.1 | 4 | 1.0 | 4 |
| 34 | 8.1 | 3 | 2.8 | 3 |
| 35 | 12 | 4 | 1.4 | 4 |
| 36 | 4.0 | 5 | 1.7 | 5 |
| 37 | 2.9 | 7 | 1.3 | 7 |
| 38 | 4.3 | 3 | 1.1 | 3 |
| 39 | 9.8 | 3 | 1.5 | 3 |
| 40 | 2.2 | 3 | 1.3 | 3 |
| 41 | 18 | 7 | 3.7 | 7 |
| 42 | 6.6 | 3 | 1.8 | 3 |
| 43 | 6.4 | 4 | 2.8 | 4 |
| 44 | 31 | 3 | 5.4 | 3 |
| 45 | 23 | 4 | 2.8 | 4 |
| 46 | 14 | 3 | 3.8 | 3 |
| 47 | 5.3 | 4 | 1.3 | 4 |
| 48 | 32 | 3 | 5.6 | 3 |
| 49 | 12 | 3 | 8.4 | 3 |

SEQ. ID NO. 1 provides a sequence of recombinant human ACC1 (SEQ. ID NO. 1) that can be employed in the Transcreener in vitro assay.

```
Sequence of hACC1
SEQ. ID NO. 1:
MAHHHHHHDEVDDEPSPLAQPLELNQHSRFIIGSVSEDNSEDEISNLVKLDLLEKEGSLSP

ASVGSDTLSDLGISSLQDGLALHIRSSMSGLHLVKQGRDRKKIDSQRDFTVASPAEFVTRF

GGNKVIEKVLIANNGIAAVKCMRSIRRWSYEMFRNERAIRFVVMVTPEDLKANAEYIKMAD

HYVPVPGGPNNNNYANVELILDIAKRIPVQAVWAGWGHASENPKLPELLLKNGIAFMGPP

SQAMWALGDKIASSIVAQTAGIPTLPWSGSGLRVDWQENDFSKRILNVPQELYEKGYVKD

VDDGLQAAEEVGYPVMIKASEGGGGKGIRKVNNADDFPNLFRQVQAEVPGSPIFVMRLA

KQSRHLEVQILADQYGNAISLFGRDCSVQRRHQKIIEEAPATIATPAVFEHMEQCAVKLAK

MVGYVSAGTVEYLYSQDGSFYFLELNPRLQVEHPCTEMVADVNLPAAQLQIAMGIPLYRIK

DIRMMYGVSPWGDSPIDFEDSAHVPCPRGHVIAARITSENPDEGFKPSSGTVQELNFRSN

KNVWGYFSVAAAGGLHEFADSQFGH

CFSWGENREEAISNMVVALKELSIRGDFRTTVEYLIKLLETESFQMNRIDTGWLDRLIAEKV

QAERPDTMLGVVCGALHVADVSLRNSVSNFLHSLERGQVLPAHTLLNTVDVELIYEGVKY

VLKVTRQSPNSYVVIMNGSCVEVDVHRLSDGGLLLSYDGSSYTTYMKEEVDRYRITIGNK

TCVFEKENDPSVMRSPSAGKLIQYIVEDGGHVFAGQCYAEIEVMKMVMTLTAVESGCIHY

VKRPGAALDPGCVLAKMQLDNPSKVQQAELHTGSLPRIQSTALRGEKLHRVFHYVLDNLV

NVMNGYCLPDPFFSSKVKDWVERLMKTLRDPSLPLLELQDIMTSVSGRIPPNVEKSIKKE

MAQYASNITSVLCQFPSQQIANILDSHAATLNRKSEREVFFMNTQSIVQLVQRYRSGIRGH

MKAVVMDLLRQYLRVETQFQNGHYDKCVFALREENKSDMNTVLNYIFSHAQVTKKNLLVT

MLIDQLCGRDPTLTDELLNILTELTQLSKTTNAKVALRARQVLIASHLPSYELRHNQVESIFL

SAIDMYGHQFCIENLQKLILSETSIFDVLPNFFYHSNQVVRMAALEVYVRRAYIAYELNSVQ

HRQLKDNTCVVEFQFMLPTSHPNRGNIPTLNRMSFSSNLNHYGMTHVASVSDVLLDNSF
```

-continued

```
TPPCQRMGGMVSFRTFEDFVRIFDEVMGCFSDSPPQSPTFPEAGHTSLYDEDKVPRDEP

IHILNVAIKTDCDIEDDRLAAMFREFTQQNKATLVDHGIRRLTFLVAQKDFRKQVNYEVDRR

FHREFPKFFTFRARDKFEEDRIYRHLEPALAFQLELNRMRNFDLTAIPCANHKMHLYLGAA

KVEVGTEVTDYRFFVRAIIRHSDLVTKEASFEYLQNEGERLLLEAMDELEVAFNNTNVRTD

CNHIFLNFVPTVIMDPSKIEESVRSMVMRYGSRLWKLRVLQAELKINIRLTPTGKAIPIRLFL

TNESGYYLDISLYKEVTDSRTAQIMFQAYGDKQGPLHGMLINTPYVTKDLLQSKRFQAQSL

GTTYIYDIPEMFRQSLIKLWESMSTQAFLPSPPLPSDMLTYTELVLDDQGQLVHMNRLPG

GNEIGMVAWKMTFKSPEYPEGRDIIVIGNDITYRIGSFGPQEDLLFLRASELARAEGIPRIYV

SANSGARIGLAEEIRHMFHVAWVDPEDPYKGYRYLYLTPQDYKRVSALNSVHCEHVEDE

GESRYKITDIIGKEEGIGPENLRGSGMIAGESSLAYNEIITISLVTCRAIGIGAYLVRLGQRTIQ

VENSHLILTGAGALNKVLGREVYTSNNQLGGIQIMHNNGVTHCTVCDDFEGVFTVLHWLS

YMPKSVHSSVPLLNSKDPIDRIIEFVPTKTPYDPRWMLAGRPHPTQKGQWLSGFFDYGSF

SEIMQPWAQTVVVGRARLGGIPVGVVAVETRTVELSIPADPANLDSEAKIIQQAGQVWFP

DSAFKTYQAIKDFNREGLPLMVFANWRGFSGGMKDMYDQVLKFGAYIVDGLRECCQPVL

VYIPPQAELRGGSWVVIDSSINPRHMEMYADRESRGSVLEPEGTVEIKFRRKDLVKTMRR

VDPVYIHLAERLGTPELSTAERKELENKLKEREEFLIPIYHQVAVQFADLHDTPGRMQEKG

VISDILDWKTSRTFFYWRLRRLLLEDLVKKKIHNANPELTDGQIQAMLRRWFVEVEGTVKA

YVWDNNKDLAEWLEKQLTEEDGVHSVIEENIKCISRDYVLKQIRSLVQANPEVAMDSIIHM

TQHISPTQRAEVIRILSTMDSPST
```

SEQ. ID NO. 2 provides a sequence of recombinant human ACC2 (SEQ. ID NO. 2) that can be employed in the Transcreener in vitro assay.

```
Sequence of hACC2
SEQ. ID NO. 2:
MVLLLCLSCLIFSCLTFSWLKIWGKMTDSKPITKSKSEANLIPSQEPFPASDNSGETPQRN

GEGHTLPKTPSQAEPASHKGPKDAGRRRNSLPPSHQKPPRNPLSSSDAAPSPELQANGT

GTQGLEATDTNGLSSSARPQGQQAGSPSKEDKKQANIKRQLMTNFILGSFDDYSSDEDS

VAGSSRESTRKGSRASLGALSLEAYLTTGEAETRVPTMRPSMSGLHLVKRGREHKKLDL

HRDFTVASPAEFVTRFGGDRVIEKVLIANNGIAAVKCMRSIRRWAYEMFRNERAIRFVVMV

TPEDLKANAEYIKMADHYVPVPGGPNNNNYANVELIVDIAKRIPVQAVWAGWGHASENPK

LPELLCKNGVAFLGPPSEAMWALGDKIASTVVAQTLQVPTLPWSGSGLTVEWTEDDLQQ

GKRISVPEDVYDKGCVKDVDEGLEAAERIGFPPLMIKASEGGGGKGIRKAESAEDFPILFRQ

VQSEIPGSPIFLMKLAQHARHLEVQILADQYGNAVSLFGRDCSIQRRHQKIVEEAPATIAPL

AIFEFMEQCAIRLAKTVGYVSAGTVEYLYSQDGSFHFLELNPRLQVEHPCTEMIADVNLPA

AQLQIAMGVPLHRLKDIRLLYGESPWGVTPISFETPSNPPLARGHVIAARITSENPDEGFKP

SSGTVQELNFRSSKNVWGYFSVAATGGLHEFADSQFGHCFSWGENREEAISNMVVALK

ELSIRGDFRTTVEYLINLLETESFQNNDIDTGWLDYLIAEKVQAEKPDIMLGVVCGALNVAD

AMFRTCMTDFLHSLERGQVLPADSLLNLVDVELIYGGVKYILKVARQSLTMFVLIMNGCHIE

IDAHRLNDGGLLLSYNGNSYTTYMKEEVDSYRITIGNKTCVFEKENDPTVLRSPSAGKLTQ

YTVEDGGHVEAGSSYAEMEVMKMIMTLNVQERGRVKYIKRPGAVLEAGCVVARLELDDP

SKVHPAEPFTGELPAQQTLPILGEKLHQVFHSVLENLTNVMSGFCLPEPVFSIKLKEWVQK
```

-continued

```
LMMTLRHPSLPLLELQEIMTSVAGRIPAPVEKSVRRVMAQYASNITSVLCQFPSQQIATILD

CHAATLQRKADREVFFINTQSIVQLVQRYRSGIRGYMKTVVLDLLRRYLRVEHHFQQAHY

DKCVINLREQFKPDMSQVLDCIFSHAQVAKKNQLVIMLIDELCGPDPSLSDELISILNELTQL

SKSEHCKVALRARQILIASHLPSYELRHNQVESIFLSAIDMYGHQFCPENLKKLILSETTIFD

VLPTFFYHANKVVCMASLEVYVRRGYIAYELNSLQHRQLPDGTCVVEFQFMLPSSHPNR

MTVPISITNPDLLRHSTELFMDSGFSPLCQRMGAMVAFRRFEDFTRNFDEVISCFANVPKD

TPLFSEARTSLYSEDDCKSLREEPIHILNVSIQCADHLEDEALVPILRTFVQSKKNILVDYGL

RRITFLIAQEKEFPKFFTFRARDEFAEDRIYRHLEPALAFQLELNRMRNFDLTAVPCANHK

MHLYLGAAKVKEGVEVTDHRFFIRAIIRHSDLITKEASFEYLQNEGERLLLEAMDELEVAFN

NTSVRTDCNHIFLNFVPTVIMDPFKIEESVRYMVMRYGSRLWKLRVLQAEVKINIRQTTTG

SAVPIRLFITNESGYYLDISLYKEVTDSRSGNIMFHSFGNKQGPQHGMLINTPYVTKDLLQA

KRFQAQTLGTTYIYDFPEMFRQALFKLWGSPDKYPKDILTYTELVLDSQGQLVEMNRLPG

GNEVGMVAFKMRFKTQEYPEGRDVIVIGNDITFRIGSFGPGEDLLYLRASEMARAEGIPKI

YVAANSGARIGMAEEIKHMFHVAWVDPEDPHKGFKYLYLTPQDYTRISSLNSVHCKHIEE

GGESRYMITDIIGKDDGLGVENLRGSGMIAGESSLAYEEIVTISLVTCRAIGIGAYLVRLGQR

VIQVENSHIILTGASALNKVLGREVYTSNNQLGGVQIMHYNGVSHITVPDDFEGVYTILEWL

SYMPKDNHSPVPIITPTDPIDREIEFLPSRAPYDPRWMLAGRPHPTLKGTWQSGFFDHGS

FKEIMAPWAQTVVTGRARLGGIPVGVIAVETRTVEVAVPADPANLDSEAKIIQQAGQVWFP

DSAYKTAQAIKDFNREKLPLMIFANWRGFSGGMKDMYDQVLKFGAYIVDGLRQYKQPILIY

IPPYAELRGGSWVVIDATINPLCIEMYADKESRGGVLEPEGTVEIKFRKKDLIKSMRRIDPA

YKKLMEQLGEPDLSDKDRKDLEGRLKAREDLLLPIYHQVAVQFADFHDTPGRMLEKGVIS

DILEWKTARTFLYWRLRRLLLEDQVKQEILQASGELSHVHIQSMLRRWFVETEGAVKAYL

WDNNQVVVQWLEQHWQAGDGPRSTIRENITYLKHDSVLKTIRGLVEENPEVAVDCVIYLS

QHISPAERAQVVHLLSTMDSPAST
```

Acute in vivo Assessment of ACC inhibition in Experimental Animals

The ACC inhibitory activity of the compounds of the present invention can be confirmed in vivo by evaluation of their ability to reduce malonyl-CoA levels in liver and muscle tissue from treated animals.

Measurement of malonyl-CoA production inhibition in experimental animals can be determined using the following methodology.

In this method, male Sprague-Dawley Rats, maintained on standard chow and water ad libitum (225-275 g), were randomized prior to the study. Animals were either fed, or fasted for 18 hours prior to the beginning of the experiment. Two hours into the light cycle the animals were orally dosed with a volume of 5 mL/kg, (0.5% methyl cellulose; vehicle) or with the appropriate compound (prepared in vehicle). Fed vehicle controls were included to determine baseline tissue malonyl-CoA levels while fasted animals were included to determine the effect fasting had on malonyl-CoA levels. One hour after compound administration the animals were asphyxiated with $CO_2$ and the tissues were removed. Specifically, blood was collected by cardiac puncture and placed into BD Microtainer tubes containing EDTA (BD Biosciences, N.J.), mixed, and placed on ice. Plasma was used to determine drug exposure. Liver and quadriceps were removed, immediately freeze-clamped, wrapped in foil and stored in liquid nitrogen.

Tissues were pulverized under liquid $N_2$ to ensure uniformity in sampling. Malonyl-CoA was extracted from the tissue (150-200 mg) with 5 volumes 10% tricarboxylic acid in Lysing Matrix A (MP Biomedicals, PN 6910) in a FastPrep FP120 (Thermo Scientific, speed=5.5; for 45 seconds). The supernatant containing malonyl-CoA was removed from the cell debris after centrifugation at 15000×g for 30 minutes (Eppendorf Centrifuge 5402). Samples were stably frozen at −80 C until analysis was completed.

Analysis of malonyl CoA levels in liver and muscle tissue can be evaluated using the following methodology.

The method utilized the following materials: Malonyl-CoA tetralithium salt and malonyl-$^{13}C_3$-CoA trilithium salt which were purchased from Isotec (Miamisburg, Ohio, USA), sodium perchlorate (Sigma, cat no. 410241), trichloroacetic acid (ACROS, cat no. 42145), phosphoric acid (J. T. Baker, cat no. 0260-01), ammonium formate (Fluka, cat no. 17843), methanol (HPLC grade, J.T. Baker, cat no. 9093-33), and water (HPLC grade, J.T. Baker, 4218-03) were used to make the necessary mobile phases. Strata-X on-line solid phase extraction columns, 25 µm, 20 mm×2.0 mm I.D (cat no. 00M-S033-B0-CB) were obtained from Phenomenex (Torrance, Calif., USA). SunFire C18 reversed-phase columns, 3.5 µm, 100 mm×3.0 mm I.D. (cat no. 186002543) were purchased from Waters Corporation (Milford, Mass., USA).

This method may be performed utilizing the following equipment. Two-dimensional chromatography using an Agilent 1100 binary pump, an Agilent 1100 quaternary pump and two Valco Cheminert 6-port two position valves. Samples were introduced via a LEAP HTC PAL auto sampler with Peltier cooled stack maintained at 10° C. and a 20 µL sampling loop. The needle wash solutions for the autosampler were 10% trichloroacetic acid in water (w/v) for Wash 1 and 90:10 methanol:water for Wash 2. The analytical column (Sunfire) was maintained at 35° C. using a MicroTech Scientific Micro-LC Column Oven. The eluent was analyzed on an ABI Sciex API3000 triple quadrupole mass spectrometer with Turbo Ion Spray.

Two-dimensional chromatography was performed in parallel using distinct gradient elution conditions for on-line solid phase extraction and reversed-phase chromatography. The general design of the method was such that the first dimension was utilized for sample clean-up and capture of the analyte of interest followed by a brief coupling of both dimensions for elution from the first dimension onto the second dimension. The dimensions were subsequently uncoupled allowing for gradient elution of the analyte from the second dimension for quantification while simultaneously preparing the first dimension for the next sample in the sequence. When both dimensions were briefly coupled together, the flow of the mobile phase in the first dimension was reversed for analyte elution on to the second dimension, allowing for optimal peak width, peak shape, and elution time.

The first dimension of the HPLC system utilized the Phenomenex strata-X on-line solid phase extraction column and the mobile phase consisted of 100 mM sodium perchlorate/ 0.1% (v/v) phosphoric acid for solvent A and methanol for solvent B.

The second dimension of the HPLC system utilized the Waters SunFire C18 reversed-phase column and the mobile phase consisted of 100 mM ammonium formate for solvent A and methanol for solvent B. The initial condition of the gradient was maintained for 2 minutes and during this time the analyte was transferred to the analytical column. It was important that the initial condition was at a sufficient strength to elute the analyte from the on-line SPE column while retaining it on the analytical. Afterwards, the gradient rose linearly to 74.5% A in 4.5 minutes before a wash and re-equilibration step.

Mass spectrometry when coupled with HPLC can be a highly selective and sensitive method for quantitatively measuring analytes in complex matrices but is still subject to interferences and suppression. By coupling a two dimensional HPLC to the mass spectrometer, these interferences were significantly reduced. Additionally, by utilizing the Multiple Reaction Monitoring (MRM) feature of the triple quadrupole mass spectrometer, the signal-to-noise ratio was significantly improved.

For this assay, the mass spectrometer was operated in positive ion mode with a TurboIonSpray voltage of 2250V. The nebulizing gas was heated to 450° C. The Declustering Potential (DP), Focusing Potential (FP), and Collision Energy (CE) were set to 60, 340, and 42 V, respectively. Quadrupole 1 (Q1) resolution was set to unit resolution with Quadrupole 3 (Q3) set to low. The CAD gas was set to 8. The MRM transitions monitored were for malonyl CoA: 854.1→347.0 m/z (L. Gao et al. (2007) *J. Chromatogr. B* 853, 303-313); and for malonyl-$^{13}C_3$-CoA: 857.1→350.0 m/z with dwell times of 200 ms. The eluent was diverted to the mass spectrometer near the expected elution time for the analyte, otherwise it was diverted to waste to help preserve the source and improve robustness of the instrumentation. The resulting chromatograms were integrated using Analyst software (Applied Biosystems). Tissue concentrations for malonyl CoA were calculated from a standard curve prepared in a 10% solution of trichloroacetic acid in water.

Samples comprising the standard curve for the quantification of malonyl-CoA in tissue extracts were prepared in 10% (w/v) trichloroacetic acid (TCA) and ranged from 0.01 to 1 pmol/µL. Malonyl-$^{13}C_3$-CoA (final concentration of 0.4 pmol/µL) was added to each standard curve component and sample as an internal standard.

Six intra-assay quality controls were prepared; three from a pooled extract prepared from fasted animals and three from a pool made from fed animals. These were run as independent samples spiked with 0, 0.1 or 0.3 pmol/µL $^{12}$C-malonyl-CoA as well as malonyl-$^{13}C_3$-CoA (0.4 pmol/µL). Each intra-assay quality control contained 85% of aqueous tissue extract with the remaining portion contributed by internal standard (0.4 pmol/µL) and $^{12}$C-malonyl-CoA. Inter assay controls were included in each run; they consist of one fasted and one fed pooled sample of quadriceps and/or one fasted and one fed pooled sample of liver. All such controls are spiked with malonyl-$^{13}C_3$-CoA (0.4 pmol/µL).

All publications, including but not limited to issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A compound selected from the group consisting of
6-[(1-isopropyl-7-oxo-1,4,6,7-tetrahydro-1'H-spiro[indazole-5,4'-piperidin]-1'-yl)carbonyl]-1H-indole-3-carboxamide;
5-[(1-isopropyl-7-oxo-1,4,6,7-tetrahydro-1'H-spiro[indazole-5,4'-piperidin]-1'-yl)carbonyl]-1H-indazole-3-carboxamide;
6-[(1-isopropyl-7-oxo-1,4,6,7-tetrahydro-1'H-spiro[indazole-5,4'-piperidin]-1'-yl)carbonyl]-1H-pyrrolo[3,2-b]pyridine-3-carboxamide;
6-[(1-isopropyl-7-oxo-1,4,6,7-tetrahydro-1'H-spiro[indazole-5,4'-piperidin]-1'-yl)carbonyl]-1H-indazole-3-carboxamide;
5-[(1-isopropyl-7-oxo-1,4,6,7-tetrahydro-1'H-spiro[indazole-5,4'-piperidin]-1'-yl)carbonyl]-1H-pyrrolo[2,3-b]pyridine-3-carboxamide;
5-[(1-isopropyl-7-oxo-1,4,6,7-tetrahydro-1'H-spiro[indazole-5,4'-piperidin]-1'-yl)carbonyl]-1H-indole-2-carboxamide;
5-[(1-isopropyl-7-oxo-1,4,6,7-tetrahydro-1'H-spiro[indazole-5,4'-piperidin]-1'-yl)carbonyl]-1H-indole-3-carboxamide;
1'-[(2-amino-1H-benzimidazol-5-yl)carbonyl]-1-isopropyl-1,4-dihydrospiro[indazole-5,4'-piperidin]-7(6H)-one;
5-[(1-isopropyl-7-oxo-1,4,6,7-tetrahydro-1'H-spiro[indazole-5,4'-piperidin]-1'-yl)carbonyl]-N-methyl-1H-indazole-3-carboxamide;
N-ethyl-5-[(1-isopropyl-7-oxo-1,4,6,7-tetrahydro-1'H-spiro[indazole-5,4'-piperidin]-1'-yl)carbonyl]-1H-indazole-3-carboxamide;
5-[(1-isopropyl-7-oxo-1,4,6,7-tetrahydro-1'H-spiro[indazole-5,4'-piperidin]-1'-yl)carbonyl]-N-(2,2,2-trifluoroethyl)-1H-indazole-3-carboxamide;
6-[(1-isopropyl-7-oxo-1,4,6,7-tetrahydro-1'H-spiro[indazole-5,4'-piperidin]-1'-yl)carbonyl]-1H-indole-2-carboxamide;
5-[(1-isopropyl-7-oxo-1,4,6,7-tetrahydro-1'H-spiro[indazole-5,4'-piperidin]-1'-yl)carbonyl]-1H-pyrazolo[3,4-b]pyridine-3-carboxamide;
5-[(1-isopropyl-7-oxo-1,4,6,7-tetrahydro-1'H-spiro[indazole-5,4'-piperidin]-1'-yl)carbonyl]-1H-pyrrolo[2,3-b]pyridine-2-carboxamide;
1-isopropyl-1'-{[2-(methylamino)-1H-benzimidazol-5-yl]carbonyl}-1,4-dihydrospiro[indazole-5,4'-piperidin]-7(6H)-one;
5-[(1-isopropyl-7-oxo-1,4,6,7-tetrahydro-1'H-spiro[indazole-5,4'-piperidin]-1'-yl)carbonyl]-1H-benzimidazole-2-carboxamide;
5-[(1-tert-butyl-7-oxo-1,4,6,7-tetrahydro-1'H-spiro[indazole-5,4'-piperidin]-1'-yl)carbonyl]-1H-indazole-3-carboxamide;
5-[(1-tert-butyl-7-oxo-1,4,6,7-tetrahydro-1'H-spiro[indazole-5,4'-piperidin]-1'-yl)carbonyl]-1H-pyrrolo[2,3-b]pyridine-3-carboxamide;
6-[(2-tert-butyl-7-oxo-2,4,6,7-tetrahydro-1'H-spiro[indazole-5,4'-piperidin]-1'-yl)carbonyl]-1H-indole-3-carboxamide;
6-[(2-tert-butyl-7-oxo-2,4,6,7-tetrahydro-1'H-spiro[indazole-5,4'-piperidin]-1'-yl)carbonyl]-1H-indazole-3-carboxamide;
5-[(2-tert-butyl-7-oxo-2,4,6,7-tetrahydro-1'H-spiro[indazole-5,4'-piperidin]-1'-yl)carbonyl]-1H-pyrrolo[2,3-b]pyridine-3-carboxamide;
5-[(2-tert-butyl-7-oxo-2,4,6,7-tetrahydro-1'H-spiro[indazole-5,4'-piperidin]-1'-yl)carbonyl]-1H-indazole-3-carboxamide;
5-[(2-tert-butyl-7-oxo-2,4,6,7-tetrahydro-1'H-spiro[indazole-5,4'-piperidin]-1'-yl)carbonyl]-1H-indole-2-carboxamide;
5-[(2-tert-butyl-7-oxo-2,4,6,7-tetrahydro-1'H-spiro[indazole-5,4'-piperidin]-1'-yl)carbonyl]-1H-indole-3-carboxamide;
6-[(2-tert-butyl-7-oxo-2,4,6,7-tetrahydro-1'H-spiro[indazole-5,4'-piperidin]-1'-yl)carbonyl]-1H-indole-2-carboxamide;
1'-[(2-amino-1H-benzimidazol-5-yl)carbonyl]-2-tert-butyl-2,4-dihydrospiro[indazole-5,4'-piperidin]-7(6H)-one;
5-[(2-tert-butyl-7-oxo-2,4,6,7-tetrahydro-1'H-spiro[indazole-5,4'-piperidin]-1'-yl)carbonyl]-N-ethyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-methyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-(2,2,2-trifluoroethyl)-1H-indazole-3-carboxamide;
2-tert-butyl-1'-{[2-(methylamino)-1H-benzimidazol-5-yl]carbonyl}-2,4-dihydrospiro[indazole-5,4'-piperidin]-7(6H)-one;
6-[(2-tert-butyl-7-oxo-2,4,6,7-tetrahydro-1'H-spiro[indazole-5,4'-piperidin]-1'-yl)carbonyl]-1H-pyrrolo[3,2-b]pyridine-3-carboxamide;
6-[(2'-tert-butyl-7'-oxo-6',7'-dihydro-1H,2'H-spiro[piperidine-4,5'-pyrano[3,2-c]pyrazol]-1-yl)carbonyl]-1H-indazole-3-carboxamide;
6-[(2'-tert-butyl-7'-oxo-6',7'-dihydro-1H,2'H-spiro[piperidine-4,5'-pyrano[3,2-c]pyrazol]-1-yl)carbonyl]-1H-indole-2-carboxamide;
6-[(2'-tert-butyl-7'-oxo-6',7'-dihydro-1H,2'H-spiro[piperidine-4,5'-pyrano[3,2-c]pyrazol]-1-yl)carbonyl]-1H-indole-3-carboxamide;
5-[(2'-tert-butyl-7'-oxo-6',7'-dihydro-1H,2'H-spiro[piperidine-4,5'-pyrano[3,2-c]pyrazol]-1-yl)carbonyl]-1H-indazole-3-carboxamide;
5-[(2'-tert-butyl-7'-oxo-6',7'-dihydro-1H,2'H-spiro[piperidine-4,5'-pyrano[3,2-c]pyrazol]-1-yl)carbonyl]-1H-indole-2-carboxamide;
5-[(2'-tert-butyl-7'-oxo-6',7'-dihydro-1H,2'H-spiro[piperidine-4,5'-pyrano[3,2-c]pyrazol]-1-yl)carbonyl]-1H-indole-3-carboxamide;
5-[(2'-tert-butyl-7'-oxo-6',7'-dihydro-1H,2'H-spiro[piperidine-4,5'-pyrano[3,2-c]pyrazol]-1-yl)carbonyl]-1H-pyrrolo[2,3-b]pyridine-3-carboxamide;
1-[(2-amino-1H-benzimidazol-5-yl)carbonyl]-2'-tert-butyl-2'H-spiro[piperidine-4,5'-pyrano[3,2-c]pyrazol]-7'(6'H)-one;
2'-tea-butyl-1-{[2-(methylamino)-1H-benzimidazol-5-yl]carbonyl}-2'H-spiro[piperidine-4,5'-pyrano[3,2-c]pyrazol]-7'(6'H)-one;
6-[(2'-tert-butyl-7'-oxo-6',7'-dihydro-1H,2'H-spiro[piperidine-4,5'-pyrano[3,2-c]pyrazol]-1-yl)carbonyl]-1H-pyrrolo[3,2-b]pyridine-3-carboxamide; and
5-[(2'-tert-butyl-7'-oxo-6',7'-dihydro-1H,2'H-spiro[piperidine-4,5'-pyrano[3,2-c]pyrazol]-1-yl)carbonyl]-1H-benzimidazole-2-carboxamide;

or a pharmaceutically acceptable salt thereof.

2. A compound selected from the group consisting of
1'-[(2-aminoquinolin-6-yl)carbonyl]-2-tert-butyl-2,4-dihydrospiro[indazole-5,4'-piperidin]-7(6H)-one;

5-[(1-isopropyl-7-oxo-1,4,6,7-tetrahydro-1'H-spiro[indazole-5,4'-piperidin]-1'-yl)carbonyl]-N-methyl-1H-indole-3-carboxamide;
6-[(1-isopropyl-7-oxo-1,4,6,7-tetrahydro-1'H-spiro[indazole-5,4'-piperidin]-1'-yl)carbonyl]-N-methyl-1H-indole-3-carboxamide;
5-[(2-tert-butyl-7-oxo-2,4,6,7-tetrahydro-1'H-spiro[indazole-5,4'-piperidin]-1'-yl)carbonyl]-N-cyclopropyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-isopropyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-propyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-(2-methoxyethyl)-1H-indazole-3-carboxamide;
5-[(2-tert-butyl-7-oxo-2,4,6,7-tetrahydro-1'H-spiro[indazole-5,4'-piperidin]-1'-yl)carbonyl]-N-cyclobutyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-oxetan-3-yl-1H-indazole-3-carboxamide;
6-[(2-tert-butyl-7-oxo-2,4,6,7-tetrahydro-1'H-spiro[indazole-5,4'-piperidin]-1'-yl)carbonyl]-Ncyclopropyl-1H-indazole-3-carboxamide;
6-[(2-tert-butyl-7-oxo-2,4,6,7-tetrahydro-1'H-spiro[indazole-5,4'-piperidin]-1'-yl)carbonyl]-N-methyl-1H-indazole-3-carboxamide;
6-[(2-tert-butyl-7-oxo-2,4,6,7-tetrahydro-1'H-spiro[indazole-5,4'-piperidin]-1'-yl)carbonyl]-N-ethyl-1H-indazole-3-carboxamide;
6-[(2-tert-butyl-7-oxo-2,4,6,7-tetrahydro-1'H-spiro[indazole-5,4'-piperidin]-1'-yl)carbonyl]-N-(2-methoxyethyl)-1H-indazole-3-carboxamide;
6-[(2-tert-butyl-7-oxo-2,4,6,7-tetrahydro-1'H-spiro[indazole-5,4'-piperidin]-1'-yl)carbonyl]-N-isopropyl-1H-indazole-3-carboxamide;
6-[(2-tert-butyl-7-oxo-2,4,6,7-tetrahydro-1'H-spiro[indazole-5,4'-piperidin]-1'-yl)carbonyl]-N-propyl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-cyclopropyl-1H-indole-3-carboxamide;
6-[(2-tert-butyl-7-oxo-2,4,6,7-tetrahydro-1'H-spiro[indazole-5,4'-piperidin]-1'-yl)carbonyl]-N-cyclobutyl-1H-indazole-3-carboxamide;
6-[(2-tert-butyl-7-oxo-2,4,6,7-tetrahydro-1'H-spiro[indazole-5,4'-piperidin]-1'-yl)carbonyl]-N-oxetan-3-yl-1H-indazole-3-carboxamide;
5-[(2-tert-butyl-7-oxo-2,4,6,7-tetrahydro-1'H-spiro[indazole-5,4'-piperidin]-1'-yl)carbonyl]-N-(2-methoxyethyl)-1H-indole-3-carboxamide;
5-[(2-tert-butyl-7-oxo-2,4,6,7-tetrahydro-1'H-spiro[indazole-5,4'-piperidin]-1'-yl)carbonyl]-N-methyl-1H-indole-3-carboxamide;
5-[(2-tert-butyl-7-oxo-2,4,6,7-tetrahydro-1'H-spiro[indazole-5,4'-piperidin]-1'-yl)carbonyl]-N-ethyl-1H-indole-3-carboxamide; and
6-[(2-tert-butyl-7-oxo-2,4,6,7-tetrahydro-1'H-spiro[indazole-5,4'-piperidin]-1'-yl)carbonyl]-N-cyclopropyl-1H-indole-3-carboxamide;
or a pharmaceutically acceptable salt thereof.

3. A pharmaceutical composition comprising a therapeutically effective amount of a compound of claim 1, or a pharmaceutically acceptable salt thereof, and a pharmaceutically acceptable excipient, diluent, or carrier.

4. A method for treating Type 2 diabetes, diabetes or hepatic insulin resistance in a human comprising the step of administering to the human in need of such treatment a therapeutically effective amount of a compound of claim 1 or a pharmaceutically acceptable salt thereof.

5. A method for treating Type 2 diabetes or hepatic insulin resistance in a human comprising the step of administering to the human in need of such treatment the pharmaceutical composition of claim 3.

6. A compound of structure

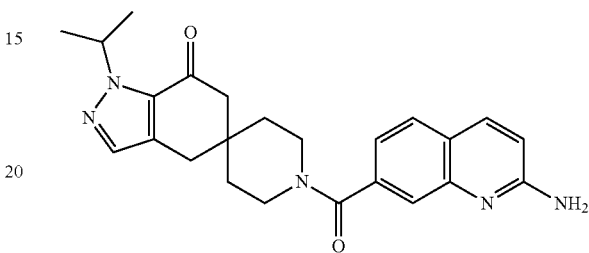

or a pharmaceutically acceptable salt thereof.

7. A compound of structure

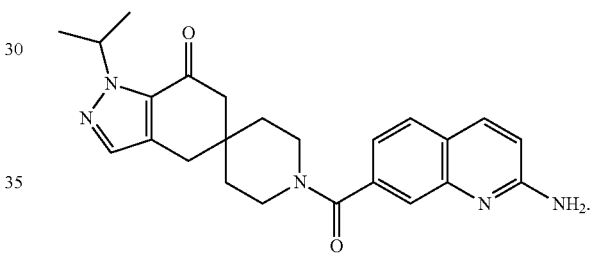

8. A compound of structure

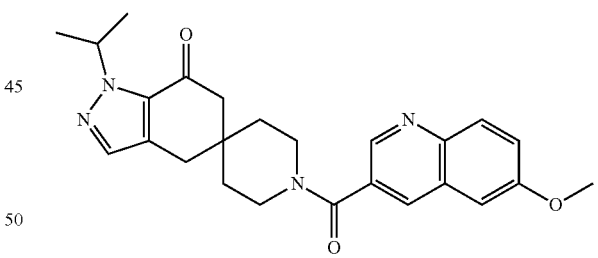

or a pharmaceutically acceptable salt thereof.

9. A compound of structure

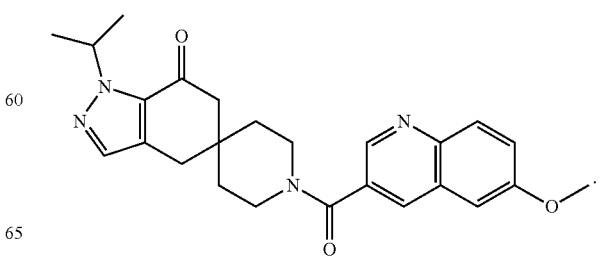

10. A compound of structure

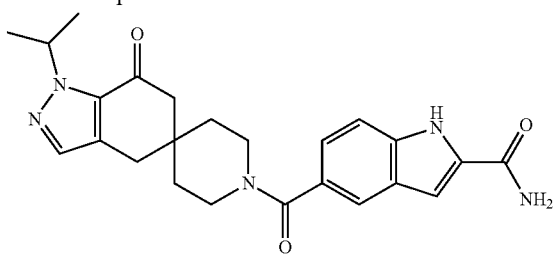

or a pharmaceutically acceptable salt thereof.

11. A compound of structure

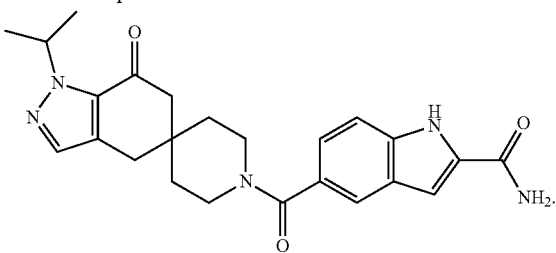

12. A compound structure

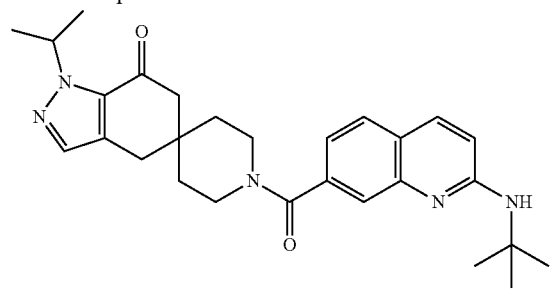

or a pharmaceutically acceptable salt thereof.

13. A compound of structure

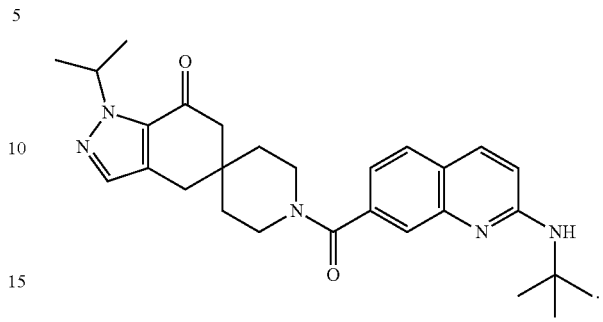

14. A pharmaceutical composition comprising a therapeutically effective amount of a compound of claim 6, or a pharmaceutically acceptable salt thereof, and a pharmaceutically acceptable excipient, diluent, or carrier.

15. A method for treating Type 2 diabetes or hepatic insulin resistance in a human comprising the step of administering to the human in need of such treatment a therapeutically effective amount of the compound of claim 6 or a pharmaceutically acceptable salt thereof.

16. A method for treating Type 2 diabetes or hepatic insulin resistance in a human comprising the step of administering to the human in need of such treatment the pharmaceutical composition of claim 14.

* * * * *

UNITED STATES PATENT AND TRADEMARK OFFICE
CERTIFICATE OF CORRECTION

PATENT NO.        : 8,802,688 B2                                Page 1 of 1
APPLICATION NO.   : 13/452839
DATED             : August 12, 2014
INVENTOR(S)       : Robert Lee Dow et al.

It is certified that error appears in the above-identified patent and that said Letters Patent is hereby corrected as shown below:

In the specification

At column 69, line 10, please delete the structure below as listed in the patent as Example 14:

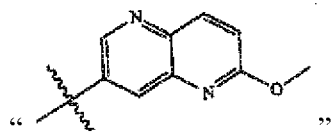

and replace it with the correct structure listed below:

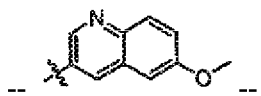

Signed and Sealed this
Thirteenth Day of October, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 2356
<212> TYPE: PRT
<213> ORGANISM: Homo sapiens

<400> SEQUENCE: 1

Met Ala His His His His His His Asp Glu Val Asp Asp Glu Pro Ser
1               5                   10                  15

Pro Leu Ala Gln Pro Leu Glu Leu Asn Gln His Ser Arg Phe Ile Ile
            20                  25                  30

Gly Ser Val Ser Glu Asp Asn Ser Glu Asp Glu Ile Ser Asn Leu Val
```

```
                35                  40                  45
Lys Leu Asp Leu Leu Glu Lys Glu Gly Ser Leu Ser Pro Ala Ser Val
    50                  55                  60

Gly Ser Asp Thr Leu Ser Asp Leu Gly Ile Ser Ser Leu Gln Asp Gly
65                  70                  75                  80

Leu Ala Leu His Ile Arg Ser Ser Met Ser Gly Leu His Leu Val Lys
                85                  90                  95

Gln Gly Arg Asp Arg Lys Lys Ile Asp Ser Gln Arg Asp Phe Thr Val
            100                 105                 110

Ala Ser Pro Ala Glu Phe Val Thr Arg Phe Gly Gly Asn Lys Val Ile
        115                 120                 125

Glu Lys Val Leu Ile Ala Asn Asn Gly Ile Ala Ala Val Lys Cys Met
    130                 135                 140

Arg Ser Ile Arg Arg Trp Ser Tyr Glu Met Phe Arg Asn Glu Arg Ala
145                 150                 155                 160

Ile Arg Phe Val Val Met Val Thr Pro Glu Asp Leu Lys Ala Asn Ala
                165                 170                 175

Glu Tyr Ile Lys Met Ala Asp His Tyr Val Pro Val Pro Gly Gly Pro
            180                 185                 190

Asn Asn Asn Asn Tyr Ala Asn Val Glu Leu Ile Leu Asp Ile Ala Lys
        195                 200                 205

Arg Ile Pro Val Gln Ala Val Trp Ala Gly Trp Gly His Ala Ser Glu
    210                 215                 220

Asn Pro Lys Leu Pro Glu Leu Leu Leu Lys Asn Gly Ile Ala Phe Met
225                 230                 235                 240

Gly Pro Pro Ser Gln Ala Met Trp Ala Leu Gly Asp Lys Ile Ala Ser
                245                 250                 255

Ser Ile Val Ala Gln Thr Ala Gly Ile Pro Thr Leu Pro Trp Ser Gly
            260                 265                 270

Ser Gly Leu Arg Val Asp Trp Gln Glu Asn Asp Phe Ser Lys Arg Ile
        275                 280                 285

Leu Asn Val Pro Gln Glu Leu Tyr Glu Lys Gly Tyr Val Lys Asp Val
    290                 295                 300

Asp Asp Gly Leu Gln Ala Ala Glu Glu Val Gly Tyr Pro Val Met Ile
305                 310                 315                 320

Lys Ala Ser Glu Gly Gly Gly Gly Lys Gly Ile Arg Lys Val Asn Asn
                325                 330                 335

Ala Asp Asp Phe Pro Asn Leu Phe Arg Gln Val Gln Ala Glu Val Pro
            340                 345                 350

Gly Ser Pro Ile Phe Val Met Arg Leu Ala Lys Gln Ser Arg His Leu
        355                 360                 365

Glu Val Gln Ile Leu Ala Asp Gln Tyr Gly Asn Ala Ile Ser Leu Phe
    370                 375                 380

Gly Arg Asp Cys Ser Val Gln Arg Arg His Gln Lys Ile Ile Glu Glu
385                 390                 395                 400

Ala Pro Ala Thr Ile Ala Thr Pro Ala Val Phe Glu His Met Glu Gln
                405                 410                 415

Cys Ala Val Lys Leu Ala Lys Met Val Gly Tyr Val Ser Ala Gly Thr
            420                 425                 430

Val Glu Tyr Leu Tyr Ser Gln Asp Gly Ser Phe Tyr Phe Leu Glu Leu
        435                 440                 445

Asn Pro Arg Leu Gln Val Glu His Pro Cys Thr Glu Met Val Ala Asp
    450                 455                 460
```

```
Val Asn Leu Pro Ala Ala Gln Leu Gln Ile Ala Met Gly Ile Pro Leu
465                 470                 475                 480

Tyr Arg Ile Lys Asp Ile Arg Met Met Tyr Gly Val Ser Pro Trp Gly
            485                 490                 495

Asp Ser Pro Ile Asp Phe Glu Asp Ser Ala His Val Pro Cys Pro Arg
                500                 505                 510

Gly His Val Ile Ala Ala Arg Ile Thr Ser Glu Asn Pro Asp Glu Gly
                515                 520                 525

Phe Lys Pro Ser Ser Gly Thr Val Gln Glu Leu Asn Phe Arg Ser Asn
            530                 535                 540

Lys Asn Val Trp Gly Tyr Phe Ser Val Ala Ala Gly Gly Leu His
545                 550                 555                 560

Glu Phe Ala Asp Ser Gln Phe Gly His Cys Phe Ser Trp Gly Glu Asn
                565                 570                 575

Arg Glu Glu Ala Ile Ser Asn Met Val Val Ala Leu Lys Glu Leu Ser
            580                 585                 590

Ile Arg Gly Asp Phe Arg Thr Thr Val Glu Tyr Leu Ile Lys Leu Leu
            595                 600                 605

Glu Thr Glu Ser Phe Gln Met Asn Arg Ile Asp Thr Gly Trp Leu Asp
610                 615                 620

Arg Leu Ile Ala Glu Lys Val Gln Ala Glu Arg Pro Asp Thr Met Leu
625                 630                 635                 640

Gly Val Val Cys Gly Ala Leu His Val Ala Asp Val Ser Leu Arg Asn
                645                 650                 655

Ser Val Ser Asn Phe Leu His Ser Leu Glu Arg Gly Gln Val Leu Pro
                660                 665                 670

Ala His Thr Leu Leu Asn Thr Val Asp Val Glu Leu Ile Tyr Glu Gly
            675                 680                 685

Val Lys Tyr Val Leu Lys Val Thr Arg Gln Ser Pro Asn Ser Tyr Val
    690                 695                 700

Val Ile Met Asn Gly Ser Cys Val Glu Val Asp Val His Arg Leu Ser
705                 710                 715                 720

Asp Gly Gly Leu Leu Ser Tyr Asp Gly Ser Ser Tyr Thr Thr Tyr
                725                 730                 735

Met Lys Glu Glu Val Asp Arg Tyr Arg Ile Thr Ile Gly Asn Lys Thr
            740                 745                 750

Cys Val Phe Glu Lys Glu Asn Asp Pro Ser Val Met Arg Ser Pro Ser
    755                 760                 765

Ala Gly Lys Leu Ile Gln Tyr Ile Val Glu Asp Gly His Val Phe
770                 775                 780

Ala Gly Gln Cys Tyr Ala Glu Ile Glu Val Met Lys Met Val Met Thr
785                 790                 795                 800

Leu Thr Ala Val Glu Ser Gly Cys Ile His Tyr Val Lys Arg Pro Gly
                805                 810                 815

Ala Ala Leu Asp Pro Gly Cys Val Leu Ala Lys Met Gln Leu Asp Asn
            820                 825                 830

Pro Ser Lys Val Gln Gln Ala Glu Leu His Thr Gly Ser Leu Pro Arg
            835                 840                 845

Ile Gln Ser Thr Ala Leu Arg Gly Glu Lys Leu His Arg Val Phe His
        850                 855                 860

Tyr Val Leu Asp Asn Leu Val Asn Val Met Asn Gly Tyr Cys Leu Pro
865                 870                 875                 880
```

-continued

Asp Pro Phe Phe Ser Ser Lys Val Lys Asp Trp Val Glu Arg Leu Met
                885                 890                 895

Lys Thr Leu Arg Asp Pro Ser Leu Pro Leu Leu Glu Leu Gln Asp Ile
        900                 905                 910

Met Thr Ser Val Ser Gly Arg Ile Pro Pro Asn Val Glu Lys Ser Ile
        915                 920                 925

Lys Lys Glu Met Ala Gln Tyr Ala Ser Asn Ile Thr Ser Val Leu Cys
        930                 935                 940

Gln Phe Pro Ser Gln Gln Ile Ala Asn Ile Leu Asp Ser His Ala Ala
945                 950                 955                 960

Thr Leu Asn Arg Lys Ser Glu Arg Glu Val Phe Phe Met Asn Thr Gln
        965                 970                 975

Ser Ile Val Gln Leu Val Gln Arg Tyr Arg Ser Gly Ile Arg Gly His
        980                 985                 990

Met Lys Ala Val Val Met Asp Leu Leu Arg Gln Tyr Leu Arg Val Glu
        995                 1000                1005

Thr Gln Phe Gln Asn Gly His Tyr Asp Lys Cys Val Phe Ala Leu
    1010                1015                1020

Arg Glu Glu Asn Lys Ser Asp Met Asn Thr Val Leu Asn Tyr Ile
    1025                1030                1035

Phe Ser His Ala Gln Val Thr Lys Lys Asn Leu Leu Val Thr Met
    1040                1045                1050

Leu Ile Asp Gln Leu Cys Gly Arg Asp Pro Thr Leu Thr Asp Glu
    1055                1060                1065

Leu Leu Asn Ile Leu Thr Glu Leu Thr Gln Leu Ser Lys Thr Thr
    1070                1075                1080

Asn Ala Lys Val Ala Leu Arg Ala Arg Gln Val Leu Ile Ala Ser
    1085                1090                1095

His Leu Pro Ser Tyr Glu Leu Arg His Asn Gln Val Glu Ser Ile
    1100                1105                1110

Phe Leu Ser Ala Ile Asp Met Tyr Gly His Gln Phe Cys Ile Glu
    1115                1120                1125

Asn Leu Gln Lys Leu Ile Leu Ser Glu Thr Ser Ile Phe Asp Val
    1130                1135                1140

Leu Pro Asn Phe Phe Tyr His Ser Asn Gln Val Val Arg Met Ala
    1145                1150                1155

Ala Leu Glu Val Tyr Val Arg Arg Ala Tyr Ile Ala Tyr Glu Leu
    1160                1165                1170

Asn Ser Val Gln His Arg Gln Leu Lys Asp Asn Thr Cys Val Val
    1175                1180                1185

Glu Phe Gln Phe Met Leu Pro Thr Ser His Pro Asn Arg Gly Asn
    1190                1195                1200

Ile Pro Thr Leu Asn Arg Met Ser Phe Ser Ser Asn Leu Asn His
    1205                1210                1215

Tyr Gly Met Thr His Val Ala Ser Val Ser Asp Val Leu Leu Asp
    1220                1225                1230

Asn Ser Phe Thr Pro Pro Cys Gln Arg Met Gly Gly Met Val Ser
    1235                1240                1245

Phe Arg Thr Phe Glu Asp Phe Val Arg Ile Phe Asp Glu Val Met
    1250                1255                1260

Gly Cys Phe Ser Asp Ser Pro Gln Ser Pro Thr Phe Pro Glu
    1265                1270                1275

Ala Gly His Thr Ser Leu Tyr Asp Glu Asp Lys Val Pro Arg Asp

-continued

```
          1280                1285                1290
Glu Pro Ile His Ile Leu Asn Val Ala Ile Lys Thr Asp Cys Asp
    1295                1300                1305
Ile Glu Asp Asp Arg Leu Ala Ala Met Phe Arg Glu Phe Thr Gln
    1310                1315                1320
Gln Asn Lys Ala Thr Leu Val Asp His Gly Ile Arg Arg Leu Thr
    1325                1330                1335
Phe Leu Val Ala Gln Lys Asp Phe Arg Lys Gln Val Asn Tyr Glu
    1340                1345                1350
Val Asp Arg Arg Phe His Arg Glu Phe Pro Lys Phe Phe Thr Phe
    1355                1360                1365
Arg Ala Arg Asp Lys Phe Glu Glu Asp Arg Ile Tyr Arg His Leu
    1370                1375                1380
Glu Pro Ala Leu Ala Phe Gln Leu Glu Leu Asn Arg Met Arg Asn
    1385                1390                1395
Phe Asp Leu Thr Ala Ile Pro Cys Ala Asn His Lys Met His Leu
    1400                1405                1410
Tyr Leu Gly Ala Ala Lys Val Glu Val Gly Thr Glu Val Thr Asp
    1415                1420                1425
Tyr Arg Phe Phe Val Arg Ala Ile Ile Arg His Ser Asp Leu Val
    1430                1435                1440
Thr Lys Glu Ala Ser Phe Glu Tyr Leu Gln Asn Glu Gly Glu Arg
    1445                1450                1455
Leu Leu Leu Glu Ala Met Asp Glu Leu Glu Val Ala Phe Asn Asn
    1460                1465                1470
Thr Asn Val Arg Thr Asp Cys Asn His Ile Phe Leu Asn Phe Val
    1475                1480                1485
Pro Thr Val Ile Met Asp Pro Ser Lys Ile Glu Glu Ser Val Arg
    1490                1495                1500
Ser Met Val Met Arg Tyr Gly Ser Arg Leu Trp Lys Leu Arg Val
    1505                1510                1515
Leu Gln Ala Glu Leu Lys Ile Asn Ile Arg Leu Thr Pro Thr Gly
    1520                1525                1530
Lys Ala Ile Pro Ile Arg Leu Phe Leu Thr Asn Glu Ser Gly Tyr
    1535                1540                1545
Tyr Leu Asp Ile Ser Leu Tyr Lys Glu Val Thr Asp Ser Arg Thr
    1550                1555                1560
Ala Gln Ile Met Phe Gln Tyr Gly Asp Lys Gln Gly Pro Leu
    1565                1570                1575
His Gly Met Leu Ile Asn Thr Pro Tyr Val Thr Lys Asp Leu Leu
    1580                1585                1590
Gln Ser Lys Arg Phe Gln Ala Gln Ser Leu Gly Thr Thr Tyr Ile
    1595                1600                1605
Tyr Asp Ile Pro Glu Met Phe Arg Gln Ser Leu Ile Lys Leu Trp
    1610                1615                1620
Glu Ser Met Ser Thr Gln Ala Phe Leu Pro Ser Pro Leu Pro
    1625                1630                1635
Ser Asp Met Leu Thr Tyr Thr Glu Leu Val Leu Asp Asp Gln Gly
    1640                1645                1650
Gln Leu Val His Met Asn Arg Leu Pro Gly Gly Asn Glu Ile Gly
    1655                1660                1665
Met Val Ala Trp Lys Met Thr Phe Lys Ser Pro Glu Tyr Pro Glu
    1670                1675                1680
```

-continued

```
Gly Arg Asp Ile Ile Val Ile Gly Asn Asp Ile Thr Tyr Arg Ile
1685                1690                1695

Gly Ser Phe Gly Pro Gln Glu Asp Leu Leu Phe Leu Arg Ala Ser
1700                1705                1710

Glu Leu Ala Arg Ala Glu Gly Ile Pro Arg Ile Tyr Val Ser Ala
1715                1720                1725

Asn Ser Gly Ala Arg Ile Gly Leu Ala Glu Glu Ile Arg His Met
1730                1735                1740

Phe His Val Ala Trp Val Asp Pro Glu Asp Pro Tyr Lys Gly Tyr
1745                1750                1755

Arg Tyr Leu Tyr Leu Thr Pro Gln Asp Tyr Lys Arg Val Ser Ala
1760                1765                1770

Leu Asn Ser Val His Cys Glu His Val Glu Asp Glu Gly Glu Ser
1775                1780                1785

Arg Tyr Lys Ile Thr Asp Ile Ile Gly Lys Glu Glu Gly Ile Gly
1790                1795                1800

Pro Glu Asn Leu Arg Gly Ser Gly Met Ile Ala Gly Glu Ser Ser
1805                1810                1815

Leu Ala Tyr Asn Glu Ile Ile Thr Ile Ser Leu Val Thr Cys Arg
1820                1825                1830

Ala Ile Gly Ile Gly Ala Tyr Leu Val Arg Leu Gly Gln Arg Thr
1835                1840                1845

Ile Gln Val Glu Asn Ser His Leu Ile Leu Thr Gly Ala Gly Ala
1850                1855                1860

Leu Asn Lys Val Leu Gly Arg Glu Val Tyr Thr Ser Asn Asn Gln
1865                1870                1875

Leu Gly Gly Ile Gln Ile Met His Asn Asn Gly Val Thr His Cys
1880                1885                1890

Thr Val Cys Asp Asp Phe Glu Gly Val Phe Thr Val Leu His Trp
1895                1900                1905

Leu Ser Tyr Met Pro Lys Ser Val His Ser Ser Val Pro Leu Leu
1910                1915                1920

Asn Ser Lys Asp Pro Ile Asp Arg Ile Ile Glu Phe Val Pro Thr
1925                1930                1935

Lys Thr Pro Tyr Asp Pro Arg Trp Met Leu Ala Gly Arg Pro His
1940                1945                1950

Pro Thr Gln Lys Gly Gln Trp Leu Ser Gly Phe Phe Asp Tyr Gly
1955                1960                1965

Ser Phe Ser Glu Ile Met Gln Pro Trp Ala Gln Thr Val Val Val
1970                1975                1980

Gly Arg Ala Arg Leu Gly Gly Ile Pro Val Gly Val Val Ala Val
1985                1990                1995

Glu Thr Arg Thr Val Glu Leu Ser Ile Pro Ala Asp Pro Ala Asn
2000                2005                2010

Leu Asp Ser Glu Ala Lys Ile Ile Gln Gln Ala Gly Gln Val Trp
2015                2020                2025

Phe Pro Asp Ser Ala Phe Lys Thr Tyr Gln Ala Ile Lys Asp Phe
2030                2035                2040

Asn Arg Glu Gly Leu Pro Leu Met Val Phe Ala Asn Trp Arg Gly
2045                2050                2055

Phe Ser Gly Gly Met Lys Asp Met Tyr Asp Gln Val Leu Lys Phe
2060                2065                2070
```

```
Gly Ala Tyr Ile Val Asp Gly Leu Arg Glu Cys Cys Gln Pro Val
    2075                2080                2085

Leu Val Tyr Ile Pro Pro Gln Ala Glu Leu Arg Gly Gly Ser Trp
    2090                2095                2100

Val Val Ile Asp Ser Ser Ile Asn Pro Arg His Met Glu Met Tyr
    2105                2110                2115

Ala Asp Arg Glu Ser Arg Gly Ser Val Leu Glu Pro Glu Gly Thr
    2120                2125                2130

Val Glu Ile Lys Phe Arg Arg Lys Asp Leu Val Lys Thr Met Arg
    2135                2140                2145

Arg Val Asp Pro Val Tyr Ile His Leu Ala Glu Arg Leu Gly Thr
    2150                2155                2160

Pro Glu Leu Ser Thr Ala Glu Arg Lys Glu Leu Glu Asn Lys Leu
    2165                2170                2175

Lys Glu Arg Glu Glu Phe Leu Ile Pro Ile Tyr His Gln Val Ala
    2180                2185                2190

Val Gln Phe Ala Asp Leu His Asp Thr Pro Gly Arg Met Gln Glu
    2195                2200                2205

Lys Gly Val Ile Ser Asp Ile Leu Asp Trp Lys Thr Ser Arg Thr
    2210                2215                2220

Phe Phe Tyr Trp Arg Leu Arg Arg Leu Leu Glu Asp Leu Val
    2225                2230                2235

Lys Lys Lys Ile His Asn Ala Asn Pro Glu Leu Thr Asp Gly Gln
    2240                2245                2250

Ile Gln Ala Met Leu Arg Arg Trp Phe Val Glu Val Glu Gly Thr
    2255                2260                2265

Val Lys Ala Tyr Val Trp Asp Asn Asn Lys Asp Leu Ala Glu Trp
    2270                2275                2280

Leu Glu Lys Gln Leu Thr Glu Glu Asp Gly Val His Ser Val Ile
    2285                2290                2295

Glu Glu Asn Ile Lys Cys Ile Ser Arg Asp Tyr Val Leu Lys Gln
    2300                2305                2310

Ile Arg Ser Leu Val Gln Ala Asn Pro Glu Val Ala Met Asp Ser
    2315                2320                2325

Ile Ile His Met Thr Gln His Ile Ser Pro Thr Gln Arg Ala Glu
    2330                2335                2340

Val Ile Arg Ile Leu Ser Thr Met Asp Ser Pro Ser Thr
    2345                2350                2355

<210> SEQ ID NO 2
<211> LENGTH: 2458
<212> TYPE: PRT
<213> ORGANISM: Homo sapiens

<400> SEQUENCE: 2

Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
                20                  25                  30

Thr Lys Ser Lys Ser Glu Ala Asn Leu Ile Pro Ser Gln Glu Pro Phe
            35                  40                  45

Pro Ala Ser Asp Asn Ser Gly Glu Thr Pro Gln Arg Asn Gly Glu Gly
        50                  55                  60

His Thr Leu Pro Lys Thr Pro Ser Gln Ala Glu Pro Ala Ser His Lys
65                  70                  75                  80
```

```
Gly Pro Lys Asp Ala Gly Arg Arg Asn Ser Leu Pro Ser His
            85                  90                  95

Gln Lys Pro Pro Arg Asn Pro Leu Ser Ser Asp Ala Ala Pro Ser
           100                 105                 110

Pro Glu Leu Gln Ala Asn Gly Thr Gly Thr Gln Gly Leu Glu Ala Thr
           115                 120                 125

Asp Thr Asn Gly Leu Ser Ser Ser Ala Arg Pro Gln Gly Gln Gln Ala
130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Tyr Ser Ser Asp
                165                 170                 175

Glu Asp Ser Val Ala Gly Ser Ser Arg Glu Ser Thr Arg Lys Gly Ser
                180                 185                 190

Arg Ala Ser Leu Gly Ala Leu Ser Leu Glu Ala Tyr Leu Thr Thr Gly
                195                 200                 205

Glu Ala Glu Thr Arg Val Pro Thr Met Arg Pro Ser Met Ser Gly Leu
210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
                260                 265                 270

Val Lys Cys Met Arg Ser Ile Arg Arg Trp Ala Tyr Glu Met Phe Arg
                275                 280                 285

Asn Glu Arg Ala Ile Arg Phe Val Val Met Val Thr Pro Glu Asp Leu
290                 295                 300

Lys Ala Asn Ala Glu Tyr Ile Lys Met Ala Asp His Tyr Val Pro Val
305                 310                 315                 320

Pro Gly Gly Pro Asn Asn Asn Asn Tyr Ala Asn Val Glu Leu Ile Val
                325                 330                 335

Asp Ile Ala Lys Arg Ile Pro Val Gln Ala Val Trp Ala Gly Trp Gly
                340                 345                 350

His Ala Ser Glu Asn Pro Lys Leu Pro Glu Leu Leu Cys Lys Asn Gly
                355                 360                 365

Val Ala Phe Leu Gly Pro Pro Ser Glu Ala Met Trp Ala Leu Gly Asp
                370                 375                 380

Lys Ile Ala Ser Thr Val Val Ala Gln Thr Leu Gln Val Pro Thr Leu
385                 390                 395                 400

Pro Trp Ser Gly Ser Gly Leu Thr Val Glu Trp Thr Glu Asp Asp Leu
                405                 410                 415

Gln Gln Gly Lys Arg Ile Ser Val Pro Glu Asp Val Tyr Asp Lys Gly
                420                 425                 430

Cys Val Lys Asp Val Asp Glu Gly Leu Glu Ala Ala Glu Arg Ile Gly
                435                 440                 445

Phe Pro Leu Met Ile Lys Ala Ser Glu Gly Gly Gly Gly Lys Gly Ile
450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                485                 490                 495
```

-continued

His Ala Arg His Leu Glu Val Gln Ile Leu Ala Asp Gln Tyr Gly Asn
            500                 505                 510

Ala Val Ser Leu Phe Gly Arg Asp Cys Ser Ile Gln Arg Arg His Gln
            515                 520                 525

Lys Ile Val Glu Glu Ala Pro Ala Thr Ile Ala Pro Leu Ala Ile Phe
        530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
                565                 570                 575

His Phe Leu Glu Leu Asn Pro Arg Leu Gln Val Glu His Pro Cys Thr
            580                 585                 590

Glu Met Ile Ala Asp Val Asn Leu Pro Ala Ala Gln Leu Gln Ile Ala
            595                 600                 605

Met Gly Val Pro Leu His Arg Leu Lys Asp Ile Arg Leu Leu Tyr Gly
        610                 615                 620

Glu Ser Pro Trp Gly Val Thr Pro Ile Ser Phe Glu Thr Pro Ser Asn
625                 630                 635                 640

Pro Pro Leu Ala Arg Gly His Val Ile Ala Ala Arg Ile Thr Ser Glu
                645                 650                 655

Asn Pro Asp Glu Gly Phe Lys Pro Ser Ser Gly Thr Val Gln Glu Leu
            660                 665                 670

Asn Phe Arg Ser Ser Lys Asn Val Trp Gly Tyr Phe Ser Val Ala Ala
        675                 680                 685

Thr Gly Gly Leu His Glu Phe Ala Asp Ser Gln Phe Gly His Cys Phe
690                 695                 700

Ser Trp Gly Glu Asn Arg Glu Glu Ala Ile Ser Asn Met Val Val Ala
705                 710                 715                 720

Leu Lys Glu Leu Ser Ile Arg Gly Asp Phe Arg Thr Thr Val Glu Tyr
                725                 730                 735

Leu Ile Asn Leu Leu Glu Thr Glu Ser Phe Gln Asn Asn Asp Ile Asp
            740                 745                 750

Thr Gly Trp Leu Asp Tyr Leu Ile Ala Glu Lys Val Gln Ala Glu Lys
        755                 760                 765

Pro Asp Ile Met Leu Gly Val Val Cys Gly Ala Leu Asn Val Ala Asp
770                 775                 780

Ala Met Phe Arg Thr Cys Met Thr Asp Phe Leu His Ser Leu Glu Arg
785                 790                 795                 800

Gly Gln Val Leu Pro Ala Asp Ser Leu Leu Asn Leu Val Asp Val Glu
                805                 810                 815

Leu Ile Tyr Gly Gly Val Lys Tyr Ile Leu Lys Val Ala Arg Gln Ser
            820                 825                 830

Leu Thr Met Phe Val Leu Ile Met Asn Gly Cys His Ile Glu Ile Asp
        835                 840                 845

Ala His Arg Leu Asn Asp Gly Gly Leu Leu Ser Tyr Asn Gly Asn
850                 855                 860

Ser Tyr Thr Thr Tyr Met Lys Glu Glu Val Asp Ser Tyr Arg Ile Thr
865                 870                 875                 880

Ile Gly Asn Lys Thr Cys Val Phe Glu Lys Glu Asn Asp Pro Thr Val
                885                 890                 895

Leu Arg Ser Pro Ser Ala Gly Lys Leu Thr Gln Tyr Thr Val Glu Asp
            900                 905                 910

Gly Gly His Val Glu Ala Gly Ser Ser Tyr Ala Glu Met Glu Val Met

-continued

```
            915                 920                 925
Lys Met Ile Met Thr Leu Asn Val Gln Glu Arg Gly Arg Val Lys Tyr
    930                 935                 940
Ile Lys Arg Pro Gly Ala Val Leu Glu Ala Gly Cys Val Val Ala Arg
945                 950                 955                 960
Leu Glu Leu Asp Asp Pro Ser Lys Val His Pro Ala Glu Pro Phe Thr
                965                 970                 975
Gly Glu Leu Pro Ala Gln Gln Thr Leu Pro Ile Leu Gly Glu Lys Leu
            980                 985                 990
His Gln Val Phe His Ser Val Leu Glu Asn Leu Thr Asn Val Met Ser
            995                 1000                1005
Gly Phe Cys Leu Pro Glu Pro Val Phe Ser Ile Lys Leu Lys Glu
    1010                1015                1020
Trp Val Gln Lys Leu Met Met Thr Leu Arg His Pro Ser Leu Pro
    1025                1030                1035
Leu Leu Glu Leu Gln Glu Ile Met Thr Ser Val Ala Gly Arg Ile
    1040                1045                1050
Pro Ala Pro Val Glu Lys Ser Val Arg Arg Val Met Ala Gln Tyr
    1055                1060                1065
Ala Ser Asn Ile Thr Ser Val Leu Cys Gln Phe Pro Ser Gln Gln
    1070                1075                1080
Ile Ala Thr Ile Leu Asp Cys His Ala Ala Thr Leu Gln Arg Lys
    1085                1090                1095
Ala Asp Arg Glu Val Phe Phe Ile Asn Thr Gln Ser Ile Val Gln
    1100                1105                1110
Leu Val Gln Arg Tyr Arg Ser Gly Ile Arg Gly Tyr Met Lys Thr
    1115                1120                1125
Val Val Leu Asp Leu Leu Arg Arg Tyr Leu Arg Val Glu His His
    1130                1135                1140
Phe Gln Gln Ala His Tyr Asp Lys Cys Val Ile Asn Leu Arg Glu
    1145                1150                1155
Gln Phe Lys Pro Asp Met Ser Gln Val Leu Asp Cys Ile Phe Ser
    1160                1165                1170
His Ala Gln Val Ala Lys Lys Asn Gln Leu Val Ile Met Leu Ile
    1175                1180                1185
Asp Glu Leu Cys Gly Pro Asp Pro Ser Leu Ser Asp Glu Leu Ile
    1190                1195                1200
Ser Ile Leu Asn Glu Leu Thr Gln Leu Ser Lys Ser Glu His Cys
    1205                1210                1215
Lys Val Ala Leu Arg Ala Arg Gln Ile Leu Ile Ala Ser His Leu
    1220                1225                1230
Pro Ser Tyr Glu Leu Arg His Asn Gln Val Glu Ser Ile Phe Leu
    1235                1240                1245
Ser Ala Ile Asp Met Tyr Gly His Gln Phe Cys Pro Glu Asn Leu
    1250                1255                1260
Lys Lys Leu Ile Leu Ser Glu Thr Thr Ile Phe Asp Val Leu Pro
    1265                1270                1275
Thr Phe Phe Tyr His Ala Asn Lys Val Val Cys Met Ala Ser Leu
    1280                1285                1290
Glu Val Tyr Val Arg Arg Gly Tyr Ile Ala Tyr Glu Leu Asn Ser
    1295                1300                1305
Leu Gln His Arg Gln Leu Pro Asp Gly Thr Cys Val Val Glu Phe
    1310                1315                1320
```

```
Gln Phe Met Leu Pro Ser Ser His Pro Asn Arg Met Thr Val Pro
    1325                1330                1335

Ile Ser Ile Thr Asn Pro Asp Leu Leu Arg His Ser Thr Glu Leu
    1340                1345                1350

Phe Met Asp Ser Gly Phe Ser Pro Leu Cys Gln Arg Met Gly Ala
    1355                1360                1365

Met Val Ala Phe Arg Arg Phe Glu Asp Phe Thr Arg Asn Phe Asp
    1370                1375                1380

Glu Val Ile Ser Cys Phe Ala Asn Val Pro Lys Asp Thr Pro Leu
    1385                1390                1395

Phe Ser Glu Ala Arg Thr Ser Leu Tyr Ser Glu Asp Asp Cys Lys
    1400                1405                1410

Ser Leu Arg Glu Glu Pro Ile His Ile Leu Asn Val Ser Ile Gln
    1415                1420                1425

Cys Ala Asp His Leu Glu Asp Glu Ala Leu Val Pro Ile Leu Arg
    1430                1435                1440

Thr Phe Val Gln Ser Lys Lys Asn Ile Leu Val Asp Tyr Gly Leu
    1445                1450                1455

Arg Arg Ile Thr Phe Leu Ile Ala Gln Glu Lys Glu Phe Pro Lys
    1460                1465                1470

Phe Phe Thr Phe Arg Ala Arg Asp Glu Phe Ala Glu Asp Arg Ile
    1475                1480                1485

Tyr Arg His Leu Glu Pro Ala Leu Ala Phe Gln Leu Glu Leu Asn
    1490                1495                1500

Arg Met Arg Asn Phe Asp Leu Thr Ala Val Pro Cys Ala Asn His
    1505                1510                1515

Lys Met His Leu Tyr Leu Gly Ala Ala Lys Val Lys Glu Gly Val
    1520                1525                1530

Glu Val Thr Asp His Arg Phe Phe Ile Arg Ala Ile Ile Arg His
    1535                1540                1545

Ser Asp Leu Ile Thr Lys Glu Ala Ser Phe Glu Tyr Leu Gln Asn
    1550                1555                1560

Glu Gly Glu Arg Leu Leu Leu Glu Ala Met Asp Glu Leu Glu Val
    1565                1570                1575

Ala Phe Asn Asn Thr Ser Val Arg Thr Asp Cys Asn His Ile Phe
    1580                1585                1590

Leu Asn Phe Val Pro Thr Val Ile Met Asp Pro Phe Lys Ile Glu
    1595                1600                1605

Glu Ser Val Arg Tyr Met Val Met Arg Tyr Gly Ser Arg Leu Trp
    1610                1615                1620

Lys Leu Arg Val Leu Gln Ala Glu Val Lys Ile Asn Ile Arg Gln
    1625                1630                1635

Thr Thr Thr Gly Ser Ala Val Pro Ile Arg Leu Phe Ile Thr Asn
    1640                1645                1650

Glu Ser Gly Tyr Tyr Leu Asp Ile Ser Leu Tyr Lys Glu Val Thr
    1655                1660                1665

Asp Ser Arg Ser Gly Asn Ile Met Phe His Ser Phe Gly Asn Lys
    1670                1675                1680

Gln Gly Pro Gln His Gly Met Leu Ile Asn Thr Pro Tyr Val Thr
    1685                1690                1695

Lys Asp Leu Leu Gln Ala Lys Arg Phe Gln Ala Gln Thr Leu Gly
    1700                1705                1710
```

-continued

Thr Thr Tyr Ile Tyr Asp Phe Pro Glu Met Phe Arg Gln Ala Leu
1715                1720                1725

Phe Lys Leu Trp Gly Ser Pro Asp Lys Tyr Pro Lys Asp Ile Leu
1730                1735                1740

Thr Tyr Thr Glu Leu Val Leu Asp Ser Gln Gly Gln Leu Val Glu
1745                1750                1755

Met Asn Arg Leu Pro Gly Gly Asn Glu Val Gly Met Val Ala Phe
1760                1765                1770

Lys Met Arg Phe Lys Thr Gln Glu Tyr Pro Glu Gly Arg Asp Val
1775                1780                1785

Ile Val Ile Gly Asn Asp Ile Thr Phe Arg Ile Gly Ser Phe Gly
1790                1795                1800

Pro Gly Glu Asp Leu Leu Tyr Leu Arg Ala Ser Glu Met Ala Arg
1805                1810                1815

Ala Glu Gly Ile Pro Lys Ile Tyr Val Ala Ala Asn Ser Gly Ala
1820                1825                1830

Arg Ile Gly Met Ala Glu Glu Ile Lys His Met Phe His Val Ala
1835                1840                1845

Trp Val Asp Pro Glu Asp Pro His Lys Gly Phe Lys Tyr Leu Tyr
1850                1855                1860

Leu Thr Pro Gln Asp Tyr Thr Arg Ile Ser Ser Leu Asn Ser Val
1865                1870                1875

His Cys Lys His Ile Glu Glu Gly Gly Glu Ser Arg Tyr Met Ile
1880                1885                1890

Thr Asp Ile Ile Gly Lys Asp Asp Gly Leu Gly Val Glu Asn Leu
1895                1900                1905

Arg Gly Ser Gly Met Ile Ala Gly Glu Ser Ser Leu Ala Tyr Glu
1910                1915                1920

Glu Ile Val Thr Ile Ser Leu Val Thr Cys Arg Ala Ile Gly Ile
1925                1930                1935

Gly Ala Tyr Leu Val Arg Leu Gly Gln Arg Val Ile Gln Val Glu
1940                1945                1950

Asn Ser His Ile Ile Leu Thr Gly Ala Ser Ala Leu Asn Lys Val
1955                1960                1965

Leu Gly Arg Glu Val Tyr Thr Ser Asn Asn Gln Leu Gly Gly Val
1970                1975                1980

Gln Ile Met His Tyr Asn Gly Val Ser His Ile Thr Val Pro Asp
1985                1990                1995

Asp Phe Glu Gly Val Tyr Thr Ile Leu Glu Trp Leu Ser Tyr Met
2000                2005                2010

Pro Lys Asp Asn His Ser Pro Val Pro Ile Ile Thr Pro Thr Asp
2015                2020                2025

Pro Ile Asp Arg Glu Ile Glu Phe Leu Pro Ser Arg Ala Pro Tyr
2030                2035                2040

Asp Pro Arg Trp Met Leu Ala Gly Arg Pro His Pro Thr Leu Lys
2045                2050                2055

Gly Thr Trp Gln Ser Gly Phe Phe Asp His Gly Ser Phe Lys Glu
2060                2065                2070

Ile Met Ala Pro Trp Ala Gln Thr Val Val Thr Gly Arg Ala Arg
2075                2080                2085

Leu Gly Gly Ile Pro Val Gly Val Ile Ala Val Glu Thr Arg Thr
2090                2095                2100

Val Glu Val Ala Val Pro Ala Asp Pro Ala Asn Leu Asp Ser Glu

```
                    2105                2110                2115
Ala Lys Ile Ile Gln Gln Ala Gly Gln Val Trp Phe Pro Asp Ser
         2120                2125                2130

Ala Tyr Lys Thr Ala Gln Ala Ile Lys Asp Phe Asn Arg Glu Lys
         2135                2140                2145

Leu Pro Leu Met Ile Phe Ala Asn Trp Arg Gly Phe Ser Gly Gly
         2150                2155                2160

Met Lys Asp Met Tyr Asp Gln Val Leu Lys Phe Gly Ala Tyr Ile
         2165                2170                2175

Val Asp Gly Leu Arg Gln Tyr Lys Gln Pro Ile Leu Ile Tyr Ile
         2180                2185                2190

Pro Pro Tyr Ala Glu Leu Arg Gly Gly Ser Trp Val Val Ile Asp
         2195                2200                2205

Ala Thr Ile Asn Pro Leu Cys Ile Glu Met Tyr Ala Asp Lys Glu
         2210                2215                2220

Ser Arg Gly Gly Val Leu Glu Pro Glu Gly Thr Val Glu Ile Lys
         2225                2230                2235

Phe Arg Lys Lys Asp Leu Ile Lys Ser Met Arg Arg Ile Asp Pro
         2240                2245                2250

Ala Tyr Lys Lys Leu Met Glu Gln Leu Gly Glu Pro Asp Leu Ser
         2255                2260                2265

Asp Lys Asp Arg Lys Asp Leu Glu Gly Arg Leu Lys Ala Arg Glu
         2270                2275                2280

Asp Leu Leu Leu Pro Ile Tyr His Gln Val Ala Val Gln Phe Ala
         2285                2290                2295

Asp Phe His Asp Thr Pro Gly Arg Met Leu Glu Lys Gly Val Ile
         2300                2305                2310

Ser Asp Ile Leu Glu Trp Lys Thr Ala Arg Thr Phe Leu Tyr Trp
         2315                2320                2325

Arg Leu Arg Arg Leu Leu Leu Glu Asp Gln Val Lys Gln Glu Ile
         2330                2335                2340

Leu Gln Ala Ser Gly Glu Leu Ser His Val His Ile Gln Ser Met
         2345                2350                2355

Leu Arg Arg Trp Phe Val Glu Thr Glu Gly Ala Val Lys Ala Tyr
         2360                2365                2370

Leu Trp Asp Asn Asn Gln Val Val Val Gln Trp Leu Glu Gln His
         2375                2380                2385

Trp Gln Ala Gly Asp Gly Pro Arg Ser Thr Ile Arg Glu Asn Ile
         2390                2395                2400

Thr Tyr Leu Lys His Asp Ser Val Leu Lys Thr Ile Arg Gly Leu
         2405                2410                2415

Val Glu Glu Asn Pro Glu Val Ala Val Asp Cys Val Ile Tyr Leu
         2420                2425                2430

Ser Gln His Ile Ser Pro Ala Glu Arg Ala Gln Val Val His Leu
         2435                2440                2445

Leu Ser Thr Met Asp Ser Pro Ala Ser Thr
         2450                2455
```